(12) United States Patent
Soula et al.

(10) Patent No.: US 10,792,335 B2
(45) Date of Patent: Oct. 6, 2020

(54) RAPID-ACTING INSULIN COMPOSITION COMPRISING A SUBSTITUTED CITRATE

(71) Applicant: ADOCIA, Lyons (FR)

(72) Inventors: Olivier Soula, Meyzieu (FR); Richard Charvet, Rillieux la Pape (FR); Bertrand Alluis, Genas (FR)

(73) Assignee: ADOCIA, Lyons (FR)

( * ) Notice: Subject to any disclaimer, the term of this patent is extended or adjusted under 35 U.S.C. 154(b) by 0 days.

(21) Appl. No.: 15/353,522

(22) Filed: Nov. 16, 2016

(65) Prior Publication Data
US 2017/0136097 A1 May 18, 2017

(30) Foreign Application Priority Data
Nov. 16, 2015 (FR) .................... 15 61017

(51) Int. Cl.
A61K 38/28 (2006.01)
A61K 9/08 (2006.01)
A61K 47/12 (2006.01)

(52) U.S. Cl.
CPC .............. A61K 38/28 (2013.01); A61K 9/08 (2013.01); A61K 47/12 (2013.01)

(58) Field of Classification Search
None
See application file for complete search history.

(56) References Cited

U.S. PATENT DOCUMENTS

| | | | |
|---|---|---|---|
| 2,387,201 A | 10/1945 | Weiner | |
| 2,847,385 A | 8/1958 | Hiler | |
| 4,006,059 A | 2/1977 | Butler | |
| 4,011,137 A | 3/1977 | Thompson et al. | |
| 4,126,628 A | 11/1978 | Paquet | |
| 4,438,029 A | 3/1984 | Erickson et al. | |
| 4,472,385 A | 9/1984 | Brange et al. | |
| 4,826,818 A | 5/1989 | Mori et al. | |
| 5,204,366 A | 4/1993 | Lavanish et al. | |
| 5,310,937 A | 5/1994 | Lavanish et al. | |
| 5,929,027 A | 7/1999 | Takama et al. | |
| 6,991,798 B1 | 1/2006 | Gschneidner et al. | |
| 8,241,620 B2 | 8/2012 | Dahri-Correia et al. | |
| 9,089,476 B2 | 7/2015 | Soula et al. | |
| 2004/0131583 A1 | 7/2004 | Barritault et al. | |
| 2004/0234616 A1 | 11/2004 | Sabetsky | |
| 2005/0175611 A1 | 8/2005 | Mahler et al. | |
| 2007/0191757 A1 | 8/2007 | Steiner et al. | |
| 2007/0235365 A1 | 10/2007 | Pohl et al. | |
| 2008/0014250 A1 | 1/2008 | Soula et al. | |
| 2008/0039365 A1 | 2/2008 | Steiner et al. | |
| 2008/0039368 A1 | 2/2008 | Steiner et al. | |
| 2008/0096800 A1 | 4/2008 | Pohl et al. | |
| 2008/0234227 A1 | 9/2008 | Soula et al. | |
| 2009/0048412 A1 | 2/2009 | Soula et al. | |
| 2009/0221805 A1 | 9/2009 | Dahri-Correia et al. | |
| 2009/0291114 A1 | 11/2009 | Soula et al. | |
| 2010/0137456 A1 | 6/2010 | Soula et al. | |
| 2010/0166867 A1 | 7/2010 | Soula et al. | |
| 2010/0167991 A1 | 7/2010 | Soula et al. | |
| 2010/0184965 A1 | 7/2010 | Soula et al. | |
| 2010/0227795 A1 | 9/2010 | Steiner et al. | |
| 2010/0249020 A1 | 9/2010 | Soula et al. | |
| 2011/0014189 A1 | 1/2011 | Soula et al. | |
| 2011/0159068 A1 | 6/2011 | Soula et al. | |
| 2011/0172166 A1 | 7/2011 | Charvet et al. | |
| 2011/0195025 A1 | 8/2011 | Kett et al. | |
| 2011/0195913 A1 | 8/2011 | Charvet et al. | |
| 2011/0212901 A1 | 9/2011 | Akiyoshi et al. | |
| 2011/0244530 A1 | 10/2011 | Toda et al. | |

(Continued)

FOREIGN PATENT DOCUMENTS

| CN | 1613862 A | 5/2005 |
|---|---|---|
| CN | 101835493 A | 9/2010 |

(Continued)

OTHER PUBLICATIONS

Milewska et al. ('Synthesis of symmetric and asymmetric diamides of citric acid and amino acids' Amino Acids v7 1994 pp. 89-96). (Year: 1994).*
Pohl et al. ('Ultra-rapid absorption of recombinant human insulin induced by zinc chelation and surface charge masking' Journal of Diabetes Science and Technology v6(4) Jul. 2012 pp. 755-763) (Year: 2012).*
PubChem disodium EDTA entry (retrieved from https://pubchem.ncbi.nlm.nih.gov/compound/139-33-3 on Apr. 9, 2019, 2 pages). (Year: 2019).*
Menzenski et al, "Self-assembly of supramolecular nanostructures from phenylalanine derived bolaamphiphiles", New Journal of Chemistry, 2007, vol. 31, pp. 1674-1680.

(Continued)

*Primary Examiner* — Ronald T Niebauer
(74) *Attorney, Agent, or Firm* — Oliff PLC

(57) ABSTRACT

A composition, in the form of an aqueous solution, including an insulin in hexameric form and at least one substituted citrate of formula I:

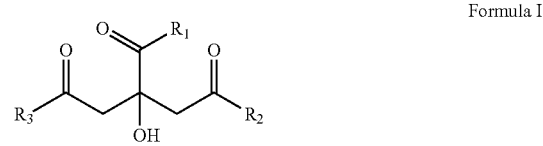

Formula I in which: $R_1$, $R_2$, $R_3$, identical or different, represent OH or AA, at least one of the $R_1$, $R_2$, $R_3$ is an AA radical, AA is a radical resulting from a natural or synthetic aromatic amino acid comprising at least one phenyl group or indole group, substituted or not substituted, said AA radical having at least one free carboxylic acid function, and the carboxylic acid functions are in the form of a salt of an alkali metal selected from $Na^+$ and $K^+$.

21 Claims, 8 Drawing Sheets

(56) References Cited

U.S. PATENT DOCUMENTS

| | | |
|---|---|---|
| 2011/0250653 A1 | 10/2011 | Toda et al. |
| 2011/0318429 A1 | 12/2011 | Ko |
| 2012/0041079 A1 | 2/2012 | Soula et al. |
| 2012/0094902 A1 | 4/2012 | Soula et al. |
| 2012/0178675 A1 | 7/2012 | Pohl et al. |
| 2012/0295833 A1 | 11/2012 | Charvet et al. |
| 2012/0309680 A1 | 12/2012 | Charvet et al. |
| 2013/0231281 A1 | 9/2013 | Soula et al. |
| 2014/0142034 A1 | 5/2014 | Soula et al. |
| 2014/0378373 A2 | 12/2014 | Soula et al. |

FOREIGN PATENT DOCUMENTS

| | | |
|---|---|---|
| CN | 101920019 A | 12/2010 |
| CN | 102300586 A | 12/2011 |
| DE | 103 55 251 A1 | 6/2005 |
| EP | 0 093 551 A2 | 11/1983 |
| EP | 0 190 041 A2 | 8/1986 |
| EP | 0 214 826 A2 | 3/1987 |
| EP | 0 441 563 A2 | 8/1991 |
| EP | 0608445 A1 | 8/1994 |
| EP | 0 648 495 A2 | 4/1995 |
| EP | 0 681 833 A2 | 11/1995 |
| EP | 0 700 683 A1 | 3/1996 |
| EP | 0 787 497 A2 | 8/1997 |
| EP | 1 623 979 A1 | 2/2006 |
| EP | 2 319 500 A1 | 5/2011 |
| EP | 2711077 A1 | 3/2014 |
| FR | 2 224 164 A1 | 10/1974 |
| FR | 2 914 305 A1 | 10/2008 |
| FR | 2 936 800 A1 | 4/2010 |
| FR | 2 943 538 A1 | 10/2010 |
| FR | 2 980 796 A1 | 4/2013 |
| JP | S47-22571 B | 6/1972 |
| JP | S61-12899 B2 | 4/1986 |
| JP | H03-153653 A | 7/1991 |
| JP | H07-82225 A | 3/1995 |
| JP | 2007-177182 A | 7/2007 |
| JP | 2007/177185 A | 7/2007 |
| JP | 2015-010075 A | 1/2015 |
| PL | 149145 B1 | 1/1990 |
| PT | 103003 A | 2/2005 |
| RU | 94026279 A | 6/1996 |
| WO | 88/06599 A1 | 9/1988 |
| WO | 90/10645 A1 | 9/1990 |
| WO | 91/009617 A1 | 7/1991 |
| WO | 96/33699 A1 | 10/1996 |
| WO | 97/49386 A1 | 12/1997 |
| WO | 99/34821 A1 | 7/1999 |
| WO | 00/064845 A1 | 11/2000 |
| WO | 02/20466 A1 | 3/2002 |
| WO | 02/053190 A2 | 7/2002 |
| WO | 03/000202 A2 | 1/2003 |
| WO | 03/014371 A1 | 2/2003 |
| WO | 03/057650 A2 | 7/2003 |
| WO | 2004/050620 A2 | 6/2004 |
| WO | 2004/093833 A2 | 11/2004 |
| WO | 2005/072803 A1 | 8/2005 |
| WO | 2005/089722 A1 | 9/2005 |
| WO | 2007/038773 A1 | 4/2007 |
| WO | 2007/041481 A1 | 4/2007 |
| WO | 2007/074456 A2 | 7/2007 |
| WO | 2007/116143 A1 | 10/2007 |
| WO | 2007/121256 A2 | 10/2007 |
| WO | 2008/038111 A1 | 4/2008 |
| WO | 2008/062466 A2 | 5/2008 |
| WO | 2008/084237 A2 | 7/2008 |
| WO | 2008/124522 A2 | 10/2008 |
| WO | 2008/152106 A1 | 12/2008 |
| WO | 2009/048945 A1 | 4/2009 |
| WO | 2009/048959 A1 | 4/2009 |
| WO | 2009/106386 A1 | 9/2009 |
| WO | 2009/127940 A1 | 10/2009 |
| WO | 2009/136500 A1 | 11/2009 |
| WO | 2010/018324 A1 | 2/2010 |
| WO | 2010/028055 A1 | 3/2010 |
| WO | 2010/041119 A1 | 4/2010 |
| WO | 2010/041138 A2 | 4/2010 |
| WO | 2010/053140 A1 | 5/2010 |
| WO | 2010/058106 A1 | 5/2010 |
| WO | 2010/067613 A1 | 6/2010 |
| WO | 2010/102020 A1 | 9/2010 |
| WO | 2010/122385 A1 | 10/2010 |
| WO | 2010/149772 A1 | 12/2010 |
| WO | 2011/077405 A1 | 6/2011 |
| WO | 2011/098962 A2 | 8/2011 |
| WO | 2012/002450 A1 | 1/2012 |
| WO | 2012/078760 A1 | 6/2012 |
| WO | 2012/124513 A1 | 9/2012 |
| WO | 2012/153070 A1 | 11/2012 |
| WO | 2012/153071 A1 | 11/2012 |
| WO | 2012/157656 A1 | 11/2012 |
| WO | 2013/021143 A1 | 2/2013 |
| WO | 2013/064787 A1 | 5/2013 |
| WO | 2014/076423 A1 | 5/2014 |
| WO | 2015/173427 A2 | 11/2015 |

OTHER PUBLICATIONS

Jul. 22, 2016 Office Action Issued in U.S Appl. No. 14/712,696.

Nov. 15, 2016 International Preliminary Report on Patentability issued in PCT Patent Application No. PCT/EP2015/060820.

Adediran, S.A. et al., "Deacylation Transition States of a Bacterial DD-Peptidase" Biochemistry, 45, 13074-13082 (2006).

Nov. 15, 2016 International Preliminary Report on Patentability issued in PCT Patent Application No. PCT/EP2015/060732.

Wu et al.; "Reactive Impurities in Excipients: Profiling, Identification and Mitigation of Drug-Excipient Incompatibility; AAPS PharmSciTech;" Dec. 2011; pp. 1248-1263; vol. 12, No. 4.

Gildersleeve et al.; "Improved Procedure for Direct Coupling of Carbohydrates to Proteins via Reductive Amination;" Bioconjug Chem.; Jul. 2008; pp. 1485-1490; vol. 19, No. 7.

U.S. Appl. No. 15/410,524, filed Jan. 19, 2017 in the name of Soula et al.

U.S. Appl. No. 14/711,378, filed May 13, 2015 in the name of Soula et al.

U.S. Appl. No. 14/712,696, filed May 14, 2015 in the name of Soula et al.

U.S. Appl. No. 14/712,328, filed May 14, 2015 in the name of Soula.

U.S. Appl. No. 15/353,522, filed Nov. 16, 2016 in the name of Soula et al.

Siddique & Duhamel, Supporting Information for "Effect of Polypeptide Sequence on Polypeptide Self-Assembly", Langmuir, 2011, 27(11), pp. 1-77.

Apr. 27, 2016 Office Action issued in Chinese Application No. 201380059092.4.

"Chemical Book" Sodium N-acetyl-DL-tryptophanate; (downloaded online on Jan. 17, 2017 from URL: <http://www.chemicalbook.com/ProductChemicalPropertiesCB7932982_EN.htm>).

ChEBI-70976-N-acetyltryptophan (downloaded online on Jan. 17, 2017 from URL: <http://www.ebi.ac.uk/chebi/searchId.do;jsessionid=0C30621862A25C54A3A6EFBB1CFB84D0?chebild=CHEBI:70976>).

"Sigma-Aldrich L-tryptophan" (downloaded online on Jan. 18, 2017 from URL: <http:///www.sigmaaldrich.com/catalog/substance/ltrytophan204237322311?lang=en® ion =US#>).

"Sigma-Aldrich L-tyrosine" (downloaded online on Jan. 18, 2017 from URL: <http://www.sigmaaldrich.com/catalog/substance/ltyrosine181196018411?lang=en&region=US>).

Mar. 7, 2017 Office Action issued in U.S. Appl. No. 14/711,378.

Mar. 1, 2017 Office Action issued in U.S. Appl. No. 14/712,328.

Feb. 8, 2017 Office Action issued in Chinese Application No. 201380059092.4.

Feb. 15, 2016 Search Report issued in PCT Patent Application No. PCT/EP2015/060820.

Jul. 14, 2015 Search Report issued in PCT Patent Application No. PCT/EP2015/060732.

(56) References Cited

OTHER PUBLICATIONS

Ramesh & Chandrasekaran, "But-2-ynylbisoxycarbonyl Chloride: A Novel C2-Symmetric Reagent for the Protection of Amines and Amino Acids," Organic Letters, 2005, 7(22), with Supporting Information pp. 1-54.
Tse et al, "Translation of DNA into a Library of 13,000 Synthetic Small-Molecule Macrocycles Suitable for in Vitro Selection", Journal of the American Chemical Society, 2008, 130(46), with Supporting Information pp. 1-9.
Mar. 20, 2017 Search Report issued in International Application No. PCT/EP2016/077912.
Baudys, Miroslav et al., "Extending Insulin Action in Vivo by Conjugation to Carboxymethyl Dextran," Bioconjugate Chem. 1998, vol. 9, pp. 176-183.
Brange, Jens et al., "Insulin analogs with improved pharmacokinetic profiles," Advanced Drug Delivery Reviews, 1999, vol. 35, pp. 307-335.
Giger, Katie et al., "Suppression of Insulin Aggregation by Heparin," Biomacromolecules, 2008, vol. 9, pp. 2338-2344.
Lou, Xianwen et al., "Simulation of size exclusion chromatography for characterization of supramolecular complex: a theoretical study," Journal of Chromatography A, 2004, vol. 1029, pp. 67-75.
Tschantz, William R. et al., "Substrate Binding is Required for Release of Product from Mammalian Protein Farnesyltransferase," The Journal of Biological Chemistry, 1997, vol. 272, No. 15, pp. 9989-9993.
Oct. 14, 2009 Search Report issued in French Patent Application No. 0901478.
Jul. 12, 2010 Written Opinion issued in International Patent Application No. PCT/IB2010/000711.
Jul. 12, 2010 Search Report issued in International Patent Application No. PCT/IB2010/000711.
Sep. 19, 2012 Office Action issued in U.S. Appl. No. 12/662,036.
Arranz et al., "Water-insoluble dextrans by grafting, 3a) Reaction of dextran with butyl isocyanate. Chemical hydrolysis," Makromol. Chem., vol. 188, pp. 2831-2838, 1987.
Carpino et al., "Efficiency in Peptide Coupling: 1-Hydroxy-7-azabenzotriazole vs 3,4-Dihydro-3-hydroxy-4-oxo-1,2,3-benzotriazine," Journal of Organic Chemistry, vol. 60, pp. 3561-3564, 1995.
Caulfield et al., "The Permeability of Glomerular Capillaries to Graded Dextrans," The Journal of Cell Biology, vol. 63, pp. 883-903, 1974.
Chang et al., "Permselectivity of the glomerular capillary wall: III. Restricted transport of polyanions," Kidney International, vol. 8, pp. 212-218, 1975.
Demitras et al, Inorganic Chemistry, Prentice-Hall International Inc., 1972, enclosed pp. 292-295.
Engelmann et al., "Preparation of Starch Carbamates in Homogeneous Phase using Different Mixing Conditions," Starch/Stärke, 2001, pp. 560-569, vol. 53, Wiley-VCH Verlag GmbH.
Larsen, "Dextran prodrugs—structure and stability in relation to therapeutic activity," Advanced Drug Delivery Reviews, 1989, pp. 103-154, vol. 3, Elsevier.
Ouari et al., "Synthesis of a Glycolipidic Amphiphilic Nitrone as a New Spin Trap," J. Org. Chem., 1999, pp. 3554-3556, vol. 64, American Chemical Society (with 10 pages of supporting information).
Shen et al., "Synthesis and Characterization of Cellulose Carbamates Having alpha-Amino Acid Moieties," Polymer Bulletin, 2005, pp. 317-322, vol. 55.
Tsai et al., "Synthesis of Amino Acid Ester Isocyanates: Methyl (S)-2-Isocyanato-3-Phenylpropanoate [Benzenepropanoic acid, alpha-isocyanato-, methyl ester, (S)]," Organic Syntheses Coll., vol. 10, p. 544, 2004; vol. 78, p. 220, 2002.
Won, "Synthesis of heterobifunctional poly(ethylene glycol) containing an acryloyl group at one end and an isocyanate group at the other end," Polymer Bulletin, 2004, pp. 109-115, vol. 52.
Definition of Phenylalanine, from Croatian-English Chemistry Dictionary & Glossary (http://glossary.periodni.com/glossary.php?en=phenylalanine, enclosed, pp. 1-2, Accessed Jan. 17, 2013.
May 3, 2012 French Search Report issued in French Patent Application No. 1158885.
Feb. 22, 2013 Office Action issued in U.S. Appl. No. 12/662,036.
Feb. 28, 2013 Office Action issued in U.S. Appl. No. 13/468,799.
U.S. Appl. No. 12/662,036 to Soula et al., filed Mar. 29, 2010.
U.S. Appl. No. 13/287,793 to Soula et al., filed Nov. 2, 2011.
U.S. Appl. No. 13/468,799 to Charvet et al., filed May 10, 2012.
U.S. Appl. No. 13/468,849 to Charvet et al., filed Jul. 11, 2012.
Heinze et al.; "Functional Polymers Based on Dextran;" Adv. Polym. Sci.; 2006; pp. 199-291; vol. 205; Springer-Verlag Berlin Heidelberg
May 28, 2014 Office Action issued in U.S. Appl. No. 13/468,849.
Jul. 24, 2013 Office Action issued in U.S. Appl. No. 12/662,036.
R. Janowski, et al., "Two Polymorphs of a Covalent Complex Between Papain and a Diazomethylketone Inhibitor," J. Peptide Res. 64, 2004, pp. 141-150.
Apr. 2, 2013 International Search Report issued in PCT/FR2012/052543.
Jun. 25, 2014 Office Action issued in U.S. Appl. No. 13/668,000.
Definition of derivative, analog, and analogue, from http://cancerweb.ncl.ac.uk/omd/about.html, pp. 1-5, accessed Jul. 7, 2005.
"Polymer Molecular Weight Distribution and Definitions of MW Averages," from www.agilent.com/chem, pp. 1-4, Jun. 10, 2011.
Dec. 12, 2011 French Search Report issued in French Patent Application No. 1154039.
Rudd, Pauline M. et al., "Glycoforms modify the dynamic stability and functional activity of an enzyme." Biochemistry :1994) 33 p. 17-22.
MEMO, Myriad-Mayo guidance, Mar. 2014.
Chain A ribonuclease b complex with D(Tetra-(Deoxy-Adenylate)) (protein data bank, accession No. 1RBJ_, upload Oct. 10, 2012).
Solomons, T.W. Graham; Organic Chemistry, 4th Edition, (1988) ISBN 0-471-83659-1, p. 751.
Roussel et al., "Monolayer lipid membrane-forming dissymmetrical bolaamphiphiles derived from alginate oligosaccharides; " Chem. Communications; 2006; pp. 3622-3624 with supplement information.
Watanabe et al., "Synthesis of lipid A type carboxymethyl derivatives with ether chains instead of ester chains and their LPS-antagonistic activities;" Carbohydrate Research; 2003; pp. 47-54; vol. 338.
Song et al., 6-O-Amino-2-O-carboxymethyl Glucopyranoside as Novel Glycoaminoxy Acid Building Block for the Construction of Oligosaccharide Mimetics; Synthesis; 2011; pp. 2761-2766; No. 17 and supporting information S1-S23.
Tareq et al., "Ieodoglucomides A and B from a Marine-Derived Bacterium Bacillus lichentiformis;" Organic Letters; 2012; pp. 1464-1467; vol. 14, No. 6.
Smoot et al., "Oligosaccharide Synthesis: From Conventional Methods to Modem Expeditious Strategies;" Advances in Carbohydrate Chemistry and Biochemistry; 2009; pp. 161-250: vol. 62.
Pal et al., "Molecular mechanism of physical gelation of hydrocarbons by fatty acid amides of natural amino acids," Tetrahedron; 2007; pp. 7334-7348; vol. 63.
Bhaskar et al., "The Selective Silylation of D-Mannitol Assisted by Phenylboronic Acid and the Solid State and Solution Structures of the Intermediate 1,6-bis(silyl) bis(phenylboronates);" Journal of Carbohydrate Chemistry; 2003; pp. 867-879; vol. 22, 9.
Edwards et al., "Dispiroketals in Synthesis (Part 18): Regioselective and Enantioselective Protection of Symmetric Polyol Substrates Using an Enantiopure (2S,2'S)-Dimethyl-bis-dihydropyran;" Synlett; 1995; pp. 898-900; vol. 9.
Ruiz-Pena et al., "Physico-chemical studies of molecular interactions between non-ionic surfactants and bovine serum albumin;" Colloids and Surfaces B: Biointerfaces: 2010: pp. 282-289; vol. 75.
Sawardeker, Jawahar S. et al., "Quantitative determination of monosaccharides as their alditol acetates by gas liquid chromatography." Anal. Chem. (1965) 37 (12) p. 1602-1604.

(56) References Cited

OTHER PUBLICATIONS

Murray "Chapter 6 Class notes for physical chemistry from the University of Washington;" http://www.ocean.washington.edu/courses/oc400/Lecture_Notes/CHPT6.pdf, Oct. 2004.
Garanger, Elisabeth et al., "Simplified syntheses of complex multifunctional nanomaterials." Chem. Communications (2008) 4792-4794.
Oct. 15, 2014 Office Action issued in U.S. Appl. No. 14/079,437.
May 21, 2015 Office Action issued in U.S. Appl. No. 14/079,437.
U.S. Appl. No. 14/079,437, filed Nov. 13, 2013 in the name of Soula et al.
U.S. Appl. No. 14/581,239, filed Dec. 23, 2014 in the name of Soula et al.
U.S. Appl. No. 14/079,516, filed Nov. 13, 2013 in the name of Soula et al.
Dec. 18, 2015 Office Action issued in U.S. Appl. No. 14/079,437.
Wagner, Herman L., "The Mark-Houwink-Sakurada equation for the viscosity of linear polyethylene." J. Phys. Chem. Ref. Data (1985) 14(2) p. 611-617.
Wayne, Richard P., "Principles and applications of photochemistry" (1988) ISBN 0-19-855234-3; pp. 106.
"Gas Chromatography Autoinjector (AOC-14) Improves Accuracy of Capillary Column Analysis;" Shimadzu scientific publication SC-AP-GC-0138, downloaded Dec. 1, 2015.
Dec. 21, 2015 Office Action issued in U.S. Appl. No. 14/079,516.
Jan. 22, 2016 Office Action issued in U.S. Appl. No. 14/581,239.
Jun. 10, 2016 Office Action Issued in U.S Appl. No. 14/079,516.
Huus, Kasper et al., "Thermal Dissociation and Unfolding of Insulin", Biochemistry, 2005, vol. 44, pp. 11171-11177.
Uversky, Vladimir N. et al., "Prediction of the Association State of Insulin Using Spectral Parameters", Journal of Pharmaceutical Sciences, Apr. 2003, vol. 92, No. 4, pp. 847-858.
Lindhorst, Thisbe K, "O-Glycoside synthesis", Essentials of Carbohydrate Chemistry and Biochemistry, 2007, pp. 157-208.
Yalpani, Manssur et al., "Selective Chemical Modifications of Dextran", Journal of Polymer Science, 1985, vol. 23, pp. 1395-1405.
Cho, Byung Tae et al., "Direct and indirect reductive amination of aldehydes and ketones with solid acid-activated sodium borohydride under solvent-free conditions", Tetrahedron, 2005, vol. 61, pp. 5725-5734.
Zhang, Tianhong et al., "Novel Polysaccharide Surfactants: Synthesis of Model Compounds and Dextran-Based Surfactants", Macromolecules, 1994, vol. 27, pp. 7302-7308.
Takeoka, Shinji et al., "Physical properties and packing states of molecular assemblies of synthetic glycolipids in aqueous dispersions", Journal of the Chemical Society, Faraday Transactions, 1998, vol. 94, No. 15, pp. 2151-2158.
Sisu, Ioana et al., "Synthesis and structural characterization of amino-functionalized polysaccharides", Central European Journal of Chemistry, 2009, vol. 7, No. 1, pp. 66-73.
Kalra, Sanjay et al., "Ultra-fast acting insulin analogies", Recent Patents on Endocrine, Metabolic & Immune Drug Discovery, 2014, vol. 8, No. 2, pp. 117-123.
May 17, 2016 Office Action Issued in U.S Appl. No. 14/711,378.
Nov. 15, 2016 International Preliminary Report on Patentability issued in International Application No. PCT/EP2015/060716.
Ramesh & Chandrasekaran, "But-2-ynylbisoxycarbonyl Chloride: A Novel C2-Symmetric Reagent for the Protection of Amines and Amino Acids," Organic Letters, 2005, 7(22), 4947-4950.
Kartvelishvili et al, "Amino acid based bioanalogous polymers. Synthesis of novel poly(urethane amide)s based on N, N'-(trimethylenedioxy-dicarbonyl)bis(phenylalanine)," Macromolecular Chemistry and Physics, 1996, 197, 249-257.
Coker et al, "Pathways for the Decay of Organic Dichloramines and Liberation of Antimicrobial Chloramine Gases", Chemical Research in Toxicology, 2008, 21(12), 2334-2343.

Schuster et al, "Chymotryspin-catalyzed peptide synthesis in ice: use of unprotected amino acids as acyl acceptors", Tetrahedron Letters, 1993, 34(36), 5701-5702.
Votano et al, "Inhibition of deoxyhemoglobin S polymerization by biaromatic peptides found to associate with the hemoglobin molecule at a preferred site", Biochemistry, 1985, 24, 1966-1970.
Gorecki et al, "Peptide inhibitors of sickle hemoglobin aggregation: effect of hydrophobicity", Biochemistry, 1980, 19(8), 1564-1568.
Behe et al, "Quantitative assessment of the noncovalent inhibition of sickle hemoglobin gelation by phenyl derivatives and other known agents", Biochemistry, 1979, 18(19), 4196-4201.
Khosla et al, "Synthesis of mixed N alpha, N epsilon-peptides of lysine through direct N epsilon-peptidation", Journal of Scientific and Industrial Research, Section B: Physical Sciences, 1962, 21B, 318-321.
Liwschitz et al, "The reaction of N-maleoylamino-acids with benzylamine," Journal of the Chemical Society, 1962, 3726-3729.
Huffman et al, "Substrate specificity of isopenicillin N synthase", Journal of Medicinal Chemistry, 1992, 35, 1897-1914.
Swamy et al, "Synthesis of iron (III). cobalt (II), nickel (II), copper (II) and zinc (II) complexes with new quadridentate N, O-donor ligands", Oriental Journal of Chemistry, 2008, 24(3), 1103-1106.
Bergeron et al.; "An investigation of the Impact of Molecular Geometry upon Microcapsule Self-Assembly;", Journal of American Chemical Society, 1995, 117(25), 6658-65.
Coker et al, Supporting information for "Antimicrobial activity of chlorinated amino acids and peptides." Chemical Research in Toxicology, 2008, 21(12), 1-11.
Tse et al, "Translation of DNA into a Library of 13 000 Synthetic Small-Molecule Macrocycles Suitable for in Vitro Selection", Journal of the American Chemical Society, 2008, 130(46), 15611-15626.
Liu et al, "Ring opening polymerization of aliphatic cyclic carbonates in the presence of natural amino acids", Journal of Applied Polymer Science, 2008, 107(5), 3275-3279.
Gartner et al, "Multistep small-molecule synthesis programmed by DNA templates", Journal of the American Chemical Society, 2002, 124(35), 10304-10306 with supporting information pp. 1-4.
Siddique & Duhamel, "Effect of Polypeptide Sequence on Polypeptide Self-Assembly", Langmuir, 2011, 27(11), 6639-6650.
Sun et al, "Homo-cysteinyl peptide inhibitors of the L1 metallo-β-lactamase, and SAR as determined by combinatorial library synthesis", Bioorganic & Medicinal Chemistry Letters, 2006, 16(19), 5169-5175.
Hong et al, "Determination of inhibitory constants for CPA by competitive spectrophotometry", Peptides: Biology and Chemistry, Proceedings of the Chinese Peptide Symposium, 5th, Lanzhou, China, Jul. 14-17, 1998 (2000), pp. 247-248.
Humme, "Amino acid derivatives hydrolyzable by an enzyme of rennet. III. Peptides", Neth. Milk Dayry J., 1971, 25(1), 3-14.
Fruchart et al, "A new linker for the synthesis of C-terminal peptide alpha-oxo-aldehydes," Tetrahedron Letters, 1999, 40, 6225-6228.
U.S. Statutory Invention Registration No. H645, published Jun. 6, 1989.
Lodi et al, "Chiral aminoacid containing acyclic ligands-I. Syntheses and conformations", Tetrahedron, 1982, vol. 38, N° 14, pp. 2055-2060.
Marchelli et al, "Chiral aminoacid containing acyclic ligands-II. Complexation of alkaline earth cations", Tetrahedron, 1982, vol. 38, N°14, pp. 2061-2067.
Mar. 16, 2017 European Office Action issued in European Patent Application No. 13 801 655.5.
Apr. 21, 2017 Office Action issued in Chinese Patent Application No. 201380059136.3.
Apr. 26, 2017 Office Action issued in Japanese Patent Application No. 2015-542338.
Apr. 27, 2017 Office Action issued in Eurasian Patent Application No. 201590937128.

* cited by examiner

RAPID-ACTING INSULIN COMPOSITION COMPRISING A SUBSTITUTED CITRATE

The present invention relates to a rapid-acting insulin composition comprising a substituted citrate. The invention also relates to the rapid-acting insulin composition comprising a substituted citrate comprising, in addition, a polyanionic compound.

Since the production of insulin by genetic engineering, at the beginning of the 1980s, diabetic patients can receive human insulin for their treatment. This product greatly improved this therapy, since the immunological risks connected with the use of non-human insulin, in particular porcine insulin, have now been eliminated. However, human insulin injected by the subcutaneous route produces a hypoglycemic effect only after 60 minutes, which means that diabetic patients treated with human insulin have to administer the injection 30 minutes before the meal.

One of the problems to be solved in order to improve the health and comfort of diabetic patients is to make insulin formulations available to them that can produce a hypoglycemic response more rapidly than that of human insulin and, if possible, approximate the physiological response of the healthy person. The secretion of endogenous insulin in healthy individuals is triggered immediately by an increase in glycemia. The objective is to reduce the time period between the insulin injection and the start of the meal as much as possible.

Today, making such formulations available is considered useful for the best possible treatment of the disease.

Genetic engineering has provided an answer with the development of rapid insulin analogs. These insulins are modified on one or two amino acids so that they are absorbed more rapidly in the blood pool after a subcutaneous injection. These insulins, lispro (Humalog®, Lilly), aspart (Novolog®, Novo Nordisk) and glulisine (Apidra®, Sanofi Aventis), are stable insulin solutions with a more rapid hypoglycemic response than that of human insulin. Henceforth, patients treated with these rapid insulin analogs can administer the injection of insulin only 15 minutes before the meal.

The principle of rapid insulin analogs is to form hexamers at the concentration of 100 IU/mL in order to ensure the stability of the insulin in the commercial product, while promoting the very rapid dissociation of these hexamers to form monomers after subcutaneous injection in order to achieve a rapid action.

Human insulin, as formulated in its commercial form, does not make it possible to obtain a hypoglycemic response that, in terms of kinetics, is close to the physiological response generated by the start of a meal (increase in glycemia), since, at the concentration of use (100 IU/mL), in the presence of zinc and other excipients such as phenol or m-cresol, it self-assembles to form a hexamer, whereas it is active in the form of a monomer and of a dimer. Human insulin is prepared in the form of hexamers so as to be stable for close to 2 years at 4° C. because in the form of monomers, it has a very strong tendency to aggregate and then form fibrils, which makes it lose its activity. In addition, in this aggregated form, it presents an immunological risk for the patient.

The dissociations of the hexamers to form dimers, and of the dimers to form monomers, delay its action by close to 20 minutes in comparison to a rapid insulin analog (Brange J., et al., Advanced Drug Delivery Review, 35, 1999, 307-335).

In addition, the kinetics of the passage of the insulin analogs into the blood and their glycemia-reducing kinetics are not optimal, and there is a real need for a formulation having an even shorter action time in order to approximate the kinetics of the secretion of endogenous insulin in healthy persons.

The company Biodel has proposed a solution to this problem with a human insulin formulation comprising EDTA and citric acid, as described in the patent application US200839365. By virtue of the capacity of EDTA to complex with zinc atoms and citric acid by its interactions with the cationic zones present on the surface of the insulin are described as destabilizing the hexameric form of the insulin, thus reducing its action time.

However, such a formulation presents, in particular, the disadvantage of dissociating the hexameric form of the insulin, which is the only stable form capable of meeting the stability requirements of the pharmaceutical regulations.

In addition, in the name of the applicant, the applications PCT WO2010/122385 and WO2013/064787 are also known, which describe formulations of human insulin or insulin analog and of a polysaccharide or of a substituted oligosaccharide comprising carboxyl groups.

However, the requirements entailed by the chronic and intensive use or even from the pediatric use of such formulations lead the person skilled in the art to seek to use excipients whose molecular weight and size are as small as possible to facilitate elimination.

The polysaccharides described as excipients in the applications WO 2010/122385A1 and US 2012/094902A1 are compounds consisting of chains whose lengths are statistically variable and which have an abundance of potential sites of interaction with the active protein ingredients. This abundance could induce a lack of specificity in terms of interaction, and a smaller and better defined molecule could make it possible to be more specific in this regard.

In addition, a molecule with a well-defined backbone is in general more easily traceable (MS/MS, for example) in the biological media in pharmacokinetics experiments or ADME (administration, distribution, metabolism, elimination) experiments in comparison to a polymer which generally produces very diffuse and noisy signals in mass spectrometry.

On the contrary, it is not ruled out that a well-defined and shorter molecule could present a deficit of potential sites of interaction with active protein ingredients. Indeed, due to their reduced size, the small molecules do not have the same properties as polysaccharide polymers, since there may be a loss of the polymer effect.

The substituted citrates of the compositions according to the invention present a generally higher degree of substitution than that observed in the polymers/oligomers of the prior art.

The application EP 0 093 551 discloses molecules derived from phenylalanine that are capable of improving the absorption of a medicinal substance (such as insulin) in the context of oral or rectal administration. These modes of administration are compatible with galenic forms that are not aqueous solutions. For example, this application describes suspensions, tablets, gel capsules, or also suppositories. It also describes that a fatty oil can be considered as liquid support.

The applicant, however, succeeded in developing formulations that are capable of accelerating the insulin by using a substituted citrate.

In one embodiment, the formulation can comprise, in addition, a polyanionic compound.

In addition, as in the case of the use of polysaccharides, the hexameric nature of the insulin is not affected, and thus the stability of the formulations is not affected, which, furthermore, is confirmed by the examples of the association state of the insulin analog lispro and of human insulin in circular dichroism in the presence of substituted citrates according to the invention, and optionally of polyanionic compound.

The stability, in particular the physical stability, of the formulations according to the invention is also an important development criterion. In particular, the formulations have to meet the requirements of the pharmacopoeias in terms of long-term physical and/or chemical stability.

The present invention makes it possible to solve the different problems described above, completely or in part, since it makes it possible, in particular, to produce a formulation of human insulin or insulin analog capable, after administration, of accelerating the passage of the human insulin or of its analogs into the blood and of reducing the glycemia more rapidly, in comparison to corresponding commercial insulin products. The compositions according to the invention are injectable aqueous solutions according to the pharmacopoeia, in particular the European or the American Pharmacopoeia.

The invention consists of a composition, in the form of an aqueous solution, comprising an insulin in hexameric form and at least one substituted citrate.

In one embodiment, the composition comprises, in addition, at least one polyanionic compound different from said substituted citrate.

In one embodiment, the pH of the composition is between 6 and 8.

"Aqueous solution" is understood to mean a solution in the meaning of the European Pharmacopoeia.

The solution according to the invention can thus be in accordance with the European Pharmacopoeia 8.0, which defines that an injectable preparation of soluble insulin has the properties of a colorless, non-opalescent liquid that is free of foreign substances; trace amounts of very fine sediments possibly depositing during storage (01/2008: 0834).

The solution according to the invention can be a non-opalescent or even clear liquid.

According to the European Pharmacopoeia 8.0 in section 2.2.1, a liquid is considered to be clear if it has an opalescence that is not more pronounced than that of the control suspension I, which has an opalescence value of 3 UTN. The opalescence of the solution can be determined by the visual method and/or by the instrumental method, referred to as turbidimetry. Said methods are defined in the European Pharmacopoeia 8.0 in section 2.2.1.

Quite particularly, the solution according to the invention has a turbidity of less than or equal to 3 UTN according to the different methods described in the European Pharmacopoeia 8.0 in section 2.2.1.

In one embodiment, the compositions according to the invention are sterilized by filtration through a 0.22 μm membrane, for example, by filtration through a membrane SLGV033RS, Millex-GV from Millipore, 0.22 μm membrane made of PVDF.

In one embodiment, the pH of the solution is between 6 and 8.

In one embodiment, the invention relates to a composition, in the form of an aqueous solution, comprising an insulin in hexameric form, and at least one substituted citrate of formula I:

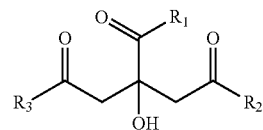

Formula I in which:
R$_1$, R$_2$, R$_3$, identical or different, represent OH or AA, at least one of the R$_1$, R$_2$, R$_3$ is an AA radical,
AA is a radical resulting from a natural or synthetic aromatic amino acid comprising at least one phenyl group or indole group, substituted or not substituted, said AA radical having at least one free carboxylic acid function,
the carboxylic acid functions are in the form of a salt of an alkali metal selected from Na$^+$ and K$^+$.

In one embodiment, the composition is characterized in that it comprises, in addition, at least one polyanionic compound different form said substituted citrate.

"Natural or synthetic aromatic amino acid comprising at least one phenyl group or indole group, substituted or not substituted" is understood to mean a compound comprising from 7 to 20 carbon atoms, a phenyl or an indole, substituted or not substituted, an amine function and a carboxylic acid function.

In one embodiment, the substituted citrate forms an amide bond with the radical resulting from an amino acid—AA. Thus, group R$_1$, R$_2$ or R$_3$ are amino acid residues bound via their amine function to an acid function of the citrate, thus forming an amide bond.

As specified above, the degrees of substitution with AA radical per gram of compounds are high in comparison to those of the polymers/oligomers of the prior art.

Moreover, the number of carboxylate functions of the substituted citrate, resulting from the citrate or the AA radicals, is greater than the number of carboxylate functions borne per monomer unit of the polymers/oligomers of the prior art.

Finally, the ratio of carboxylate functions with respect to the hydroxyl functions is much higher in the case of the substituted citrate than in the case of the polymers/oligomers of the prior art.

According to one embodiment, the composition is characterized in that the substituted citrate is selected from the compounds of formula I in which the AA radical results from a natural or synthetic aromatic amino acid comprising at least one phenyl group or indole group, substituted or not substituted, selected from the alpha or beta amino acids. The aromatic amino acids comprising a phenyl or an indole, substituted or not substituted, can be selected from the group consisting of phenylalanine, alpha-methylphenylalanine, 3,4-dihydroxyphenylalanine, alpha-phenylglycine, 4-hydroxyphenylglycine, 3,5-dihydroxyphenylglycine, tyrosine, alpha-methyltyrosine, O-methyltyrosine, and tryptophan.

In one embodiment, the composition is characterized in that the substituted citrate is selected from the compounds of formula I in which the AA radical results from a natural aromatic amino acid.

According to one embodiment, the natural aromatic amino acid is selected from the group consisting of phenylalanine, tyrosine and tryptophan.

In a preferred embodiment, the natural aromatic amino acid is phenylalanine.

The aromatic amino acids, as the case may be, can be in levorotatory or dextrorotatory form or in racemic form. In particular, they are in levorotatory form.

In a preferred embodiment, the aromatic amino acid is L-phenylalanine.

In a preferred embodiment, the aromatic amino acid is L-tryptophan.

In a preferred embodiment, the aromatic amino acid is L-tyrosine.

In one embodiment, the composition is characterized in that the substituted citrate is selected from the compounds of formula I in which the AA radical results from a synthetic aromatic amino acid.

According to one embodiment, the synthetic aromatic amino acid is alpha-phenylglycine.

According to one embodiment, the composition is characterized in that the substituted citrate comprises from 1 to 3 AA radicals.

In one embodiment, the composition is characterized in that the substituted citrate is selected from the compounds of formula I in which $R_1$ is an AA radical.

In one embodiment, the composition is characterized in that the substituted citrate is selected from the compounds of formula I in which $R_2$ is an AA radical.

In one embodiment, the composition is characterized in that the substituted citrate is selected from the compounds of formula I in which at least $R_1$ is an AA radical.

In one embodiment, the composition is characterized in that the substituted citrate is selected from the compounds of formula I in which at least $R_2$ is an AA radical.

In one embodiment, the composition is characterized in that the substituted citrate is selected from the compounds of formula I in which at least two of $R_1$, $R_2$, $R_3$ are an AA radical.

In one embodiment, the composition is characterized in that the substituted citrate is selected from the compounds of formula I in which at least $R_1$ and $R_2$ are an AA radical.

In one embodiment, the composition is characterized in that the substituted citrate is selected from the compounds of formula I in which at least $R_2$ and $R_3$ are an AA radical.

In one embodiment, the composition is characterized in that the substituted citrate is selected from the compounds of formula I in which $R_1$, $R_2$ and $R_3$ are an AA radical.

In one embodiment, the composition is characterized in that the substituted citrate is selected from the compounds of formula I in which $R_1$ is an AA radical, and $R_2$ and $R_3$ are OH.

In one embodiment, the composition is characterized in that the substituted citrate is selected from the compounds of formula I in which $R_2$ is an AA radical, and $R_1$ and $R_3$ are OH.

In one embodiment, the composition is characterized in that the substituted citrate is selected from the compounds of formula I in which $R_1$ is OH, and $R_2$ and $R_3$ are an AA radical.

In one embodiment, when $R_1$ and $R_2$, $R_1$ and $R_3$, $R_2$ and $R_3$ or $R_1$, $R_2$ and $R_3$ are an AA radical, all the AA radicals are identical.

In one embodiment, when $R_1$ and $R_2$, $R_1$ and $R_3$, $R_2$ and $R_3$ or $R_1$, $R_2$ and $R_3$ are an AA radical, all the AA radicals result from phenylalanine, in particular L-phenylalanine.

In one embodiment, the composition is characterized in that the substituted citrate is selected from the compounds of the following formula II:

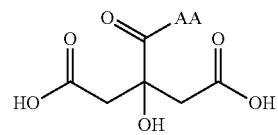

Formula II in which AA is defined as above,
the carboxylic acid functions are in the form of a salt of an alkali metal selected from $Na^+$ and $K^+$.

In one embodiment, the composition is characterized in that the substituted citrate is selected from the compounds of formula II in which AA results from an aromatic amino acid selected from the group consisting of phenylalanine, tyrosine and tryptophan.

In one embodiment, the composition is characterized in that the substituted citrate is selected from the compounds of formula II in which AA results from L-phenylalanine.

In one embodiment, the composition is characterized in that the substituted citrate is selected from the compounds of formula I in which $R_2$ or $R_3$ is an AA radical, $R_1$ is OH, if $R_2$=AA then $R_3$=OH, and if $R_3$=AA then $R_2$ is OH.

In one embodiment, the composition is characterized in that the substituted citrate is selected from the compounds of the following formula III:

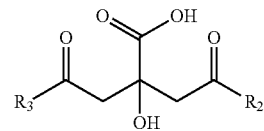

Formula III in which AA, $R_2$ and $R_3$ are defined as above, and,
if $R_2$=AA, then $R_3$=OH,
if $R_3$=AA, then $R_2$=OH,
the carboxylic acid functions are in the form of a salt of an alkali metal selected from $Na^+$ and $K^+$.

In one embodiment, the composition is characterized in that the substituted citrate is selected from the compounds of formula III in which AA results from an aromatic amino acid selected from the group consisting of phenylalanine, tyrosine and tryptophan.

In one embodiment, the composition is characterized in that the substituted citrate is selected from the compounds of formula III in which AA results from L-phenylalanine.

In one embodiment, the composition is characterized in that the substituted citrate is selected from the compounds of formula IV:

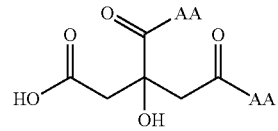

Formula IV in which the AA radical is as defined above, and the carboxylic acid functions are in the form of a salt of an alkali metal selected from $Na^+$ and $K^+$.

In one embodiment, the composition is characterized in that the substituted citrate is selected from the compounds of formula V:

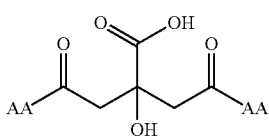

Formula V in which the AA radical is as defined above, and the carboxylic acid functions are in the form of a salt of an alkali metal selected from Na$^+$ and K$^+$.

In one embodiment, the composition is characterized in that the substituted citrate is selected from the compounds of formula VI:

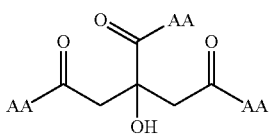

Formula VI in which the AA radical is as defined above, and the carboxylic acid functions are in the form of a salt of an alkali metal selected from Na$^+$ and K$^+$.

In one embodiment, the composition is characterized in that the substituted citrate has formula I in which $R_1$ is an AA radical, $R_2$ and $R_3$ are OH, and the AA radical results from phenylalanine.

In one embodiment, the composition is characterized in that the substituted citrate has formula I in which $R_1$ is an AA radical, $R_2$ and $R_3$ are OH, and the AA radical results from tryptophan.

In one embodiment, the composition is characterized in that the substituted citrate has formula I in which $R_1$ is an AA radical, $R_2$ and $R_3$ are OH, and the AA radical results from tyrosine.

In one embodiment, the composition is characterized in that the substituted citrate has formula IV in which the AA radical results from phenylalanine.

In one embodiment, the composition is characterized in that the substituted citrate has formula I in which $R_2$ is an AA radical, $R_1$ and $R_3$ are OH, and the AA radical results from phenylalanine.

In one embodiment, the composition is characterized in that the substituted citrate has formula I in which $R_2$ is an AA radical, $R_1$ and $R_3$ are OH, and the AA radical results from tryptophan.

In one embodiment, the composition is characterized in that the substituted citrate has formula I in which $R_2$ is an AA radical, $R_1$ and $R_3$ are OH, and the AA radical results from tyrosine.

In one embodiment, the composition is characterized in that the substituted citrate has formula I in which $R_1$ is OH, $R_2$ and $R_3$ are an AA radical, and the AA radical results from phenylalanine.

In one embodiment, the composition is characterized in that the substituted citrate has formula V in which the AA radical results from phenylalanine.

In one embodiment, the composition is characterized in that the substituted citrate has formula I in which $R_1$, $R_2$ and $R_3$ are an AA radical, and the AA radical results from phenylalanine.

In one embodiment, the composition is characterized in that the substituted citrate has formula VI in which the AA radical results from phenylalanine.

In one embodiment, the composition is characterized in that the substituted citrate/insulin molar ratios are between 3 and 400.

In one embodiment, the composition is characterized in that the substituted citrate/insulin molar ratios are between 4 and 350.

In one embodiment, the composition is characterized in that the substituted citrate/insulin molar ratios are between 5 and 300.

In one embodiment, the composition is characterized in that the substituted citrate/insulin molar ratios are between 8 and 250.

In one embodiment, the composition is characterized in that the substituted citrate/insulin molar ratios are between 12 and 200.

In one embodiment, the composition is characterized in that the substituted citrate/insulin molar ratios are between 15 and 150.

In one embodiment, the composition is characterized in that the substituted citrate/insulin molar ratios are between 18 and 128.

In one embodiment, the composition is characterized in that the substituted citrate/insulin molar ratios are between 18 and 64.

In one embodiment, the composition is characterized in that the substituted citrate/insulin molar ratios are between 18 and 36.

In one embodiment, the composition is characterized in that the substituted citrate/insulin molar ratio is equal to 18, 25, 32, 36, 50 and 64.

In the above molar ratios, the number of moles of insulin is understood to mean the number of moles of insulin monomer.

In one embodiment, the composition is characterized in that the substituted citrate/insulin mass ratios are between 0.5 and 30.

In one embodiment, the composition is characterized in that the substituted citrate/insulin mass ratios are between 0.5 and 20.

In one embodiment, the composition is characterized in that the substituted citrate/insulin mass ratios are between 0.5 and 16.

In one embodiment, the composition is characterized in that the substituted citrate/insulin mass ratios are between 0.6 and 12.

In one embodiment, the composition is characterized in that the substituted citrate/insulin mass ratios are between 1.2 and 10.

In one embodiment, the composition is characterized in that the substituted citrate/insulin mass ratios are between 1.6 and 8.

In one embodiment, the composition is characterized in that the substituted citrate/insulin mass ratios are between 2 and 8.

In one embodiment, the composition is characterized in that the substituted citrate/insulin mass ratios are between 2 and 6.

In one embodiment, the composition is characterized in that the substituted citrate/insulin mass ratios are between 2 and 4.

In one embodiment, the composition is characterized in that the substituted citrate/insulin mass ratio is 2, 3, 4 or 6.

In one embodiment, the composition is characterized in that the insulin is human insulin.

Human insulin is understood to mean an insulin obtained by synthesis or recombination, whose peptide sequence is the sequence of human insulin, including the allelic variations and the homologs.

In one embodiment, the composition is characterized in that the insulin is a recombinant human insulin as described in the European Pharmacopoeia and the American (or US) Pharmacopoeia.

In one embodiment, the composition is characterized in that the insulin is an insulin analog.

Insulin analog is understood to mean a recombinant insulin whose primary sequence contains at least one modification in comparison to the primary sequence of the human insulin.

In one embodiment, the insulin analog is selected from the group consisting of the insulin lispro (Humalog®), the insulin aspart (Novolog®, Novorapid®), and the insulin glulisine (Apidra®).

In one embodiment, the composition is characterized in that the insulin analog is the insulin lispro (Humalog®).

In one embodiment, the composition is characterized in that the insulin analog is the insulin aspart (Novolog®, Novorapid®).

In one embodiment, the composition is characterized in that the insulin analog is the insulin glulisine (Apidra®).

In one embodiment, the composition is characterized in that the insulin is in hexameric form.

The units recommended for the insulins by the pharmacopoeias are presented in the table below with their equivalents in mg:

| Insulin | Pharmacopoeia EP 8.0 (2014) | Pharmacopoeia US - USP38 (2015) |
|---|---|---|
| Aspart | 1 U = 0.0350 mg of insulin aspart | 1 USP = 0.0350 mg of insulin aspart |
| Lispro | 1 U = 0.0347 mg of insulin lispro | 1 USP = 0.0347 mg of insulin lispro |
| Human | 1 IU = 0.0347 mg of human insulin | 1 USP = 0.0347 mg of human insulin |

In the case of the insulin glulisine, 100 U=3.49 mg of insulin glulisine (according to "Annex 1—Summary of product characteristics" pertaining to ADIPRA®).

Nevertheless, in the continuation of the text, IU is used systematically for the quantities and the concentrations, interchangeably, of all the insulins. The respective equivalent values in mg are those given above for the values expressed in U, IU or USP.

In the text, when "insulin" is used without qualifier, it denotes an insulin selected from the group consisting of human insulin or insulin analogs.

In one embodiment, the composition is characterized in that the pharmaceutical composition is characterized in that the concentration of insulin is between 240 and 3000 µM (40 to 500 IU/mL).

In one embodiment, the composition is characterized in that the pharmaceutical composition is characterized in that the concentration of insulin is between 600 and 3000 µM (100 to 500 IU/mL).

In one embodiment, the composition is characterized in that the pharmaceutical composition is characterized in that the concentration of insulin is between 600 and 2400 µM (100 to 400 IU/mL).

In one embodiment, the composition is characterized in that the pharmaceutical composition is characterized in that the concentration of insulin is between 600 and 1800 µM (100 to 300 IU/mL).

In one embodiment, the composition is characterized in that the pharmaceutical composition is characterized in that the concentration of insulin is between 600 and 1200 µM (100 to 200 IU/mL).

In one embodiment, the composition is characterized in that it relates to a pharmaceutical composition characterized in that the concentration of insulin is 600 µM (100 IU/mL), 1200 µM (200 IU/mL), 1800 µM (300 IU/mL), 2400 µM (400 IU/mL) or 3000 µM (500 IU/mL).

In one embodiment, the composition is characterized in that the polyanionic compound (compound PNP) has an affinity for zinc that is less than the affinity of the insulin for zinc, and a dissociation constant $K_dCa=[\text{compound PNP}]^{r*}[Ca^{2+}]^s/[(\text{compound PNP})r\text{-}(Ca^{2+})s]$ is less than or equal to $10^{-1.5}$.

This dissociation constant is the reaction constant associated with the dissociation of the complex (compound PNP)r-$(Ca^{2+})$s, that is to say the following reaction: (compound PNP)r-$(Ca^{2+})$s dissociates to r (compound PNP)+s$Ca^{2+}$. In the present application, the symbol * is used as the multiplication sign.

The dissociation constants ($K_d$) of the different polyanionic compounds with respect to the calcium ions are determined by external calibration using an electrode specific for the calcium ions (Mettler Toledo) and a reference electrode.

All the measurements are carried out in 150 mM of NaCl at pH 7. Only the concentrations of free calcium ions are determined; the calcium ions bound to the polyanionic compound do not induce an electrode potential.

In one embodiment, the composition is characterized in that the polyanionic compound is selected from the group consisting of the carboxylic polyacids and their salts of $Na^+$, $K^+$, $Ca^{2+}$ or $Mg^{2+}$, preferably $Na^+$ or $K^+$.

In one embodiment, the composition is characterized in that the polyacid is selected from the group consisting of citric acid, aspartic acid, glutamic acid, maleic acid, tartaric acid, succinic acid, adipic acid, oxalic acid, phosphate, the phosphoric polyacids such as triphosphate and their salts of $Na^+$, $K^+$. $Ca^{2+}$ or $Mg^{2+}$, preferably $Na^+$ or $K^+$.

In one embodiment, the composition is characterized in that the polyanionic compound is selected from the group consisting of citric acid and its salts of $Na^+$, $K^+$, $Ca^{2+}$ or $Mg^{2+}$, preferably $Na^+$ or $K^+$.

In one embodiment, the composition is characterized in that the concentration of substituted citrate is between 1.8 and 100 mg/mL.

In one embodiment, the composition is characterized in that the concentration of substituted citrate is between 1.8 and 50 mg/mL.

In one embodiment, the composition is characterized in that the concentration of substituted citrate is between 1.8 and 36 mg/mL.

In one embodiment, the composition is characterized in that the concentration of substituted citrate is between 1.8 and 36.5 mg/mL.

In one embodiment, the composition is characterized in that the concentration of substituted citrate is between 2.1 and 25 mg/mL.

In one embodiment, the composition is characterized in that the concentration of substituted citrate is between 4.2 and 18 mg/mL.

In one embodiment, the composition is characterized in that the concentration of substituted citrate is between 5.6 and 15 mg/mL.

In one embodiment, the composition is characterized in that the concentration of substituted citrate is between 7 and 15 mg/mL.

In one embodiment, the composition is characterized in that the concentration of substituted citrate is 7.3 mg/mL.

In one embodiment, the composition is characterized in that the concentration of substituted citrate is 10.5 mg/mL.

In one embodiment, the composition is characterized in that the concentration of substituted citrate is 14.6 mg/mL.

In one embodiment, the composition is characterized in that the concentration of substituted citrate is 21.9 mg/mL.

In one embodiment, the composition is characterized in that the concentration of substituted citrate is between 1.8 and 100 mg for 100 IU of insulin.

In one embodiment, the composition is characterized in that the concentration of substituted citrate is between 1.8 and 50 mg for 100 IU of insulin.

In one embodiment, the composition is characterized in that the concentration of substituted citrate is between 1.8 and 36 mg for 100 IU of insulin.

In one embodiment, the composition is characterized in that the concentration of substituted citrate is between 1.8 and 36.5 mg for 100 IU of insulin.

In one embodiment, the composition is characterized in that the concentration of substituted citrate is between 2.1 and 25 mg for 100 IU of insulin.

In one embodiment, the composition is characterized in that the concentration of substituted citrate is between 4.2 and 18 mg for 100 IU of insulin.

In one embodiment, the composition is characterized in that the concentration of substituted citrate is between 5.6 and 15 mg for 100 IU of insulin.

In one embodiment, the composition is characterized in that the concentration of substituted citrate is between 7 and 15 mg for 100 IU of insulin.

In one embodiment, the composition is characterized in that the concentration of substituted citrate is 7.3 mg for 100 IU of insulin.

In one embodiment, the composition is characterized in that the concentration of substituted citrate is 10.5 mg for 100 IU of insulin.

In one embodiment, the composition is characterized in that the concentration of substituted citrate is 14.6 mg for 100 IU of insulin.

In one embodiment, the composition is characterized in that the concentration of substituted citrate is 21.9 mg for 100 IU of insulin.

In one embodiment, the composition is characterized in that the concentration of polyanionic compound is between 2 and 150 mM.

In one embodiment, the composition is characterized in that the concentration of polyanionic compound is between 2 and 100 mM.

In one embodiment, the composition is characterized in that the concentration of polyanionic compound is between 2 and 75 mM.

In one embodiment, the composition is characterized in that the concentration of polyanionic compound is between 2 and 50 mM.

In one embodiment, the composition is characterized in that the concentration of polyanionic compound is between 2 and 30 mM.

In one embodiment, the composition is characterized in that the concentration of polyanionic compound is between 2 and 20 mM.

In one embodiment, the composition is characterized in that the concentration of polyanionic compound is between 2 and 10 mM.

In one embodiment, the composition is characterized in that the concentration of polyanionic compound is between 5 and 150 mM.

In one embodiment, the composition is characterized in that the concentration of polyanionic compound is between 5 and 100 mM.

In one embodiment, the composition is characterized in that the concentration of polyanionic compound is between 5 and 75 mM.

In one embodiment, the composition is characterized in that the concentration of polyanionic compound is between 5 and 50 mM.

In one embodiment, the composition is characterized in that the concentration of polyanionic compound is between 5 and 30 mM.

In one embodiment, the composition is characterized in that the concentration of polyanionic compound is between 5 and 20 mM.

In one embodiment, the composition is characterized in that the concentration of polyanionic compound is between 5 and 10 mM.

In one embodiment, the composition is characterized in that the concentration of polyanionic compound is between 0.5 and 30 mg/mL.

In one embodiment, the composition is characterized in that the concentration of polyanionic compound is between 0.5 and 25 mg/mL.

In one embodiment, the composition is characterized in that the concentration of polyanionic compound is between 0.5 and 10 mg/mL.

In one embodiment, the composition is characterized in that the concentration of polyanionic compound is between 0.5 and 8 mg/mL.

In one embodiment, the composition is characterized in that the concentration of polyanionic compound is between 1 and 30 mg/mL.

In one embodiment, the composition is characterized in that the concentration of polyanionic compound is between 1.5 and 25 mg/mL.

In one embodiment, the composition is characterized in that the concentration of polyanionic compound is between 2 and 25 mg/mL.

In one embodiment, the composition is characterized in that the concentration of polyanionic compound is between 2 and 10 mg/mL.

In one embodiment, the composition is characterized in that the concentration of polyanionic compound is between 2 and 8 mg/mL.

In one embodiment, the composition is characterized in that the pH of the composition is between 6 and 8.

In a particular embodiment, the composition according to the invention comprises an insulin, in particular as defined above, at least one substituted citrate as defined above, and citric acid or its salts of $Na^+$, $K^+$, $Ca^{2+}$ or $Mg^{2+}$, in particular as defined above.

In a particular embodiment, the composition according to the invention comprises an insulin, in particular as defined above, at least one substituted citrate having formula I as defined above, and citric acid or its salts of $Na^+$, $K^+$, $Ca^{2+}$ or $Mg^{2+}$, in particular as defined above.

It is known to the person skilled in the art that the onset of action of insulins depends on the concentration of insulin. Only the values of the onset of action of the compositions at 100 IU/Ml are documented.

The "regular" human insulin compositions on the market at a concentration of 600 μM (100 IU/mL) have an onset of action between 50 and 90 minutes and an offset of action of approximately 360 to 420 minutes in humans. The time to reach the maximum concentration of insulin in the blood is between 90 and 180 minutes in humans.

The compositions of rapid insulin analogs on the market at a concentration of 600 μM (100 IU/mL) have an onset of action between 30 and 60 minutes and an offset of action of approximately 240-300 minutes in humans. The time to reach the maximum concentration of insulin in the blood is between 50 and 90 minutes in humans.

The invention also relates to a method for preparing a composition of human insulin having a concentration of insulin between 240 and 3000 μM (40 and 500 IU/mL), whose onset of action in humans is less than that of the reference composition at the same concentration of insulin in the absence of substituted citrate and of polyanionic compound, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention also relates to a method for preparing a composition of human insulin having a concentration of insulin between 600 and 1200 μM (100 and 200 IU/mL), whose onset of action in humans is less than that of the reference composition at the same concentration of insulin in the absence of substituted citrate and of polyanionic compound, characterized in that it comprises (I) a step of addition to the said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention also relates to a method for preparing a composition of human insulin having a concentration of insulin of 600 μM (100 IU/mL), whose onset of action in humans is less than 60 minutes, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention also relates to a method for preparing a composition of human insulin having a concentration of insulin of 1200 μM (200 IU/mL), whose onset of action in humans is at least 10% less than that of the composition of human insulin at the same concentration (200 IU/mL) and in the absence of substituted citrate and of polyanionic compound, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention also relates to a method for preparing a composition of human insulin having a concentration of insulin of 1800 μM (300 IU/mL), whose onset of action in humans is at least 10% less than that of the composition of human insulin at the same concentration (300 IU/mL) and in the absence of substituted citrate and of polyanionic compound, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention also relates to a method for preparing a composition of human insulin having a concentration of insulin of 2400 μM (400 IU/mL), whose onset of action in humans is at least 10% less than that of the composition of human insulin at the same concentration (400 IU/mL) and in the absence of substituted citrate and of polyanionic compound, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention also relates to a method for preparing a composition of human insulin having a concentration of insulin of 3000 μM (500 IU/mL), whose onset of action in humans is at least 10% less than that of the composition of human insulin at the same concentration (500 IU/mL) and in the absence of substituted citrate and of polyanionic compound, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention consists of the preparation of a composition of human insulin referred to as rapid human insulin, characterized in that it comprises (1) a step of addition to said composition of at least one substituted citrate, and, optionally, in addition, (2) a step of addition to said composition of at least one polyanionic compound.

In one embodiment, the insulin is in hexameric form.

In one embodiment, the pH of the composition is between 6 and 8.

The invention also relates to a method for preparing a composition of human insulin at a concentration of 600 μM (100 IU/mL), whose onset of action in humans is less than 60 minutes, preferably less than 45 minutes, and even more preferably less than 30 minutes, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention also relates to a method for preparing a composition of insulin analog having a concentration of insulin between 240 and 3000 μM (40 and 500 IU/mL), whose onset of action in humans is less than that of the reference composition at the same concentration of insulin in the absence of substituted citrate and of polyanionic compound, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention also relates to a method for preparing a composition of insulin analog having a concentration of insulin between 600 and 1200 µM (100 and 200 IU/mL), whose onset of action in humans is less than that of the reference composition at the same concentration of insulin in the absence of substituted citrate and of polyanionic compound, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention also relates to a method for preparing a composition of insulin analog having a concentration of insulin of 600 µmol/L (100 IU/mL), whose onset of action in humans is less than 30 minutes, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention also relates to a method for preparing a composition of insulin analog having a concentration of insulin of 1200 µM (200 IU/mL), whose onset of action in humans is at least 10% less than that of the composition of insulin analog in the absence of substituted citrate and of polyanionic compound, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention also relates to a method for preparing a composition of insulin analog having a concentration of insulin of 1800 µM (300 IU/mL), whose onset of action in humans is at least 10% less than that of the composition of insulin analog in the absence of substituted citrate and of polyanionic compound, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention also relates to a method for preparing a composition of insulin analog having a concentration of insulin of 2400 µM (400 IU/mL), whose onset of action in humans is at least 10% less than that of the composition of insulin analog in the absence of substituted citrate and of polyanionic compound, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention also relates to a method for preparing a composition of insulin analog having a concentration of insulin of 3000 µM (500 IU/mL), whose onset of action in humans is at least 10% less than that of the composition of insulin analog in the absence of substituted citrate and of polyanionic compound, characterized in that it comprises (1) a step of addition to said composition of at least one substituted citrate, and, optionally, in addition, (2) a step of addition to said composition of at least one polyanionic compound.

In one embodiment of the method, the insulin is in hexameric form.

In one embodiment of the method, the pH of the composition is between 6 and 8.

The invention consists of the preparation of a composition of insulin analog referred to as very rapid insulin analog, characterized in that it comprises a step of addition to said composition of at least one substituted citrate, the not substituted carboxyl functional groups being salifiable.

In one embodiment, the preparation comprises, in addition, a step of addition to said composition of at least one polyanionic compound.

In one embodiment, the insulin is in hexameric form.

In one embodiment, the pH of the composition is between 6 and 8.

In one embodiment, the invention also relates to the use of at least one substituted citrate, optionally in combination with a polyanionic compound, in order to prepare a pharmaceutical composition of human insulin, making it possible, after administration, to accelerate the passage of the human insulin into the blood and to reduce glycemia more rapidly in comparison to a composition that is free of substituted citrate.

In one embodiment, the invention relates to the use of at least one substituted citrate, optionally in combination with a polyanionic compound, in order to prepare a composition of insulin analog, making it possible, after administration, to accelerate the passage of the insulin analog into the blood and to reduce glycemia more rapidly in comparison to a composition that is free of substituted citrate.

In one embodiment of the use, the pH of the composition is between 6 and 8.

The invention also relates to a pharmaceutical composition according to the invention, characterized in that it is obtained by drying and/or lyophilization.

In one embodiment, the compositions according to the invention comprise, in addition, the addition of salts of zinc at a concentration between 0 and 500 µM, particularly between 0 and 300 µM, and, in particular, between 0 and 200 µM.

In one embodiment, the compositions according to the invention comprise buffers at concentrations between 0 and 100 mM, preferably between 0 and 50 mM, and even between 15 and 50 mM.

In one embodiment, the buffer is Tris.

In one embodiment, the compositions according to the invention comprise, in addition, preservatives.

In one embodiment, the preservatives are selected from the group consisting of m-cresol and phenol alone or in a mixture.

In one embodiment, the concentration of the preservatives is between 10 and 50 mM, in particular between 10 and 40 mM.

The compositions according to the invention can, in addition, comprise additives such as tonicity agents, for example, glycerol, sodium chloride (NaCl), mannitol and glycine.

The compositions according to the invention can, in addition, comprise additives in accordance with the pharmacopoeias, as surfactants, for example, polysorbate.

The compositions according to the invention can comprise, in addition, all the excipients in accordance with the pharmacopoeias and compatible with the insulins used at the concentrations of use.

In the case of local and systemic releases, the modes of administration considered are the intravenous, subcutaneous, intradermal or intramuscular routes. Quite particularly, the mode of administration is the subcutaneous route.

The routes of transdermal, oral, nasal, vaginal, ocular, buccal, pulmonary administration are also considered.

The invention also relates to the use of a composition according to the invention for the composition of a solution of human or insulin analog having a concentration of 100 IU/mL or 200 IU/mL, intended for implantable or transportable insulin pumps.

According to another of its aspects, the invention also relates to the substituted citrates as defined above.

In one embodiment, the substituted citrate has the following formula I:

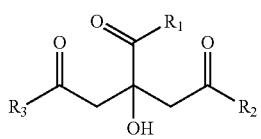

Formula I in which:
$R_1$, $R_2$, $R_3$, identical or different, represent OH or AA, only one of $R_1$, $R_2$, $R_3$ is an AA radical,
AA is a radical resulting from a natural or synthetic aromatic amino acid comprising at least one phenyl group or indole group, substituted or not substituted, said AA radical representing at least one free carboxylic acid function.

According to one embodiment, the substituted citrate is characterized in that the AA radical results from a natural or synthetic aromatic amino acid comprising at least one phenyl group or indole group, substituted or not substituted, selected from the alpha or beta amino acids. The aromatic amino acids comprising a phenyl or an indole, substituted or not substituted, can be selected from the group consisting of phenylalanine, alpha-methylphenylalanine, 3,4-dihydroxyphenylalanine, alpha-phenylglycine, 4-hydroxyphenylglycine, 3,5-dihydroxyphenylglycine, tyrosine, alpha-methyltyrosine, O-methyltyrosine and tryptophan.

In one embodiment, the substituted citrate is characterized in that the AA radical results from a natural aromatic amino acid.

According to one embodiment, the natural aromatic amino acid is selected from the group consisting of phenylalanine, tyrosine and tryptophan.

In a preferred embodiment, the natural aromatic amino acid is phenylalanine.

The aromatic amino acids can, as the case may be, be in levorotatory or dextrorotatory form or in racemic form. In particular, they are in levorotatory form.

In a preferred embodiment, the aromatic amino acid is L-phenylalanine.

In a preferred embodiment, the aromatic amino acid is L-tryptophan.

In a preferred embodiment, the aromatic amino acid is L-tyrosine.

In one embodiment, the substituted citrate is characterized in that the AA radical results from a synthetic aromatic amino acid.

According to one embodiment, the synthetic aromatic amino acid is alpha-phenylglycine.

In one embodiment, the substituted citrate is characterized in that $R_1$ is an AA radical, and $R_2$ and $R_3$ are OH.

In one embodiment, the substituted citrate has the following formula II:

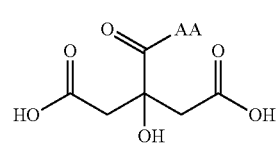

Formula II in which the AA radical is defined as above.

In one embodiment, the substituted citrate is selected from the substituted citrates of formula II in which AA results from an aromatic amino acid selected from the group consisting of phenylalanine, tyrosine and tryptophan.

In one embodiment, the substituted citrate is selected from the substituted citrates of formula II in which AA results from L-phenylalanine.

In one embodiment, the substituted citrate is characterized in that $R_2$ or $R_3$ is an AA radical, $R_1$ is OH, if $R_2$=AA then $R_3$=OH, and if $R_3$=AA then $R_2$ is OH.

In one embodiment, the substituted citrate has the following formula III:

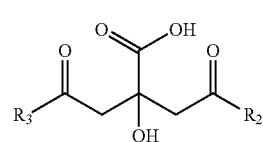

Formula III in which the AA radical, $R_2$ and $R_3$ are as defined above, and,
if $R_2$=AA, then $R_3$=OH,
if $R_3$=AA, then $R_2$=OH.

In one embodiment, the substituted citrate is selected from the substituted citrates of formula III in which AA results from an aromatic amino acid selected from the group consisting of phenylalanine, tyrosine and tryptophan.

In one embodiment, the substituted citrate is selected from the substituted citrates of formula III in which AA results from L-phenylalanine.

In one embodiment, the substituted citrate has the following formula IV:

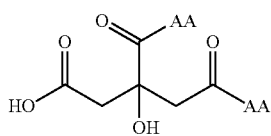

Formula IV in which the AA radical is as defined above, and the carboxylic acid functions are in the form of a salt of an alkali metal selected from Na⁺ and K⁺.

In one embodiment, the substituted citrate is selected from the substituted citrates of formula IV in which the AA radical results from an aromatic amino acid selected from the group consisting of phenylalanine, tyrosine and tryptophan.

In one embodiment, the substituted citrate is selected from the substituted citrates of formula IV in which AA results from L-phenylalanine.

In one embodiment, the composition is characterized in that the substituted citrate is selected from the compounds of formula V:

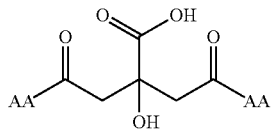

Formula V in which the AA radical is as defined above, and the carboxylic acid functions are in the form of a salt of an alkali metal selected from Na⁺ and K⁺.

In one embodiment, the substituted citrate is selected from the substituted citrates of formula V in which AA results from an aromatic amino acid selected from the group consisting of phenylalanine, tyrosine and tryptophan.

In one embodiment, the substituted citrate is selected from the substituted citrates of formula V in which the AA radical results from L-phenylalanine.

In one embodiment, the composition is characterized in that the substituted citrate is selected from the compounds of formula VI:

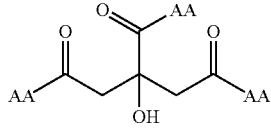

Formula VI in which the AA radical is as defined above, and the carboxylic acid functions are in the form of a salt of an alkali metal selected from Na⁺ and K⁺.

In one embodiment, the substituted citrate is selected from the substituted citrates of formula VI in which the AA radical results from an aromatic amino acid selected from the group consisting of phenylalanine, tyrosine and tryptophan.

In one embodiment, the substituted citrate is selected from the substituted citrates of formula VI in which AA radical results from L-phenylalanine.

The substituted citrates according to the invention are, for example, synthesized as in the examples below. The synthesis pathway used can be revised and adapted depending on the nature of the AA radicals that one wishes to have on the substituted citrate.

Conventional methods of the prior art that involve steps of protection/deprotection of the carboxylate functions of the citrate can be used in order to couple the functions of interest with the precursor of the AA radical.

Thus, in order to obtain a substituted citrate bearing two AA radicals, one can, for example, protect the carboxylate function of the citrate that one wishes to keep in the —COOH form, then form the amide bond by reaction between the desired carboxylate functions of the citrate and an amine function borne by the precursor of the AA radical, and then, finally, deprotect the carboxylate function of the citrate that one wishes to keep in —COOH form. This final deprotection step can also serve as a deprotection step for the carboxylate function(s) borne by the precursors of the AA radicals in —COOH form. The deprotection of the carboxylate function(s) borne by the precursors of the AA radicals borne by the citrate can optionally occur independently in a specific synthesis step before or after the deprotection step, leading to the —COOH form of the carboxylate function of the citrate being left free.

In the case in which the $R_1$, $R_2$ and $R_3$ are identical AA radicals, they are introduced in a single step by reaction between an amine function borne by their precursor and the three carboxylate functions of the citrate.

In the case where the $R_1$, $R_2$ and $R_3$ are different AA radicals, orthogonal protection/deprotection steps for the carboxylate functions of the citrate are necessary in order to obtain a substituted citrate with different AA radicals on the carboxylate functions of the citrate.

In one embodiment, the synthesis pathway of the substituted citrates involves one or more steps of deprotection of carboxylate functions, which are then converted to the —COOH form or to the carboxylate salt form.

In one embodiment, the synthesis of the substituted citrates involves a final step of conversion of the carboxylate functions of the substituted citrate from the —COOH form to the carboxylate salt form.

DESCRIPTION OF THE FIGURES

FIG. 9 describes, on the ordinate, the CD signal at 240 nm (deg·cm$^2$·dmol$^{-1}$) and, on the abscissa:
A: insulin lispro 100 IU/mL
B: insulin lispro 100 IU/mL+7.3 mg of substituted citrate A1
B': insulin lispro 100 IU/mL+7.3 mg of substituted citrate A1 and citrate at 9.3 mM
C: insulin lispro 100 IU/mL+7.3 mg of substituted citrate A2
C': insulin lispro 100 IU/mL+7.3 mg of substituted citrate A2 and citrate at 9.3 mM
D: insulin lispro 100 IU/mL+7.3 mg of substituted citrate A3
D': insulin lispro 100 IU/mL+7.3 mg of substituted citrate A3 and citrate at 9.3 mM
E: insulin lispro+EDTA at 300 µM
FIG. 10 describes, on the ordinate, the CD signal at 240 nm (deg·cm$^2$·dmol$^{-1}$) and, on the abscissa:
A: insulin lispro 100 IU/mL
F: insulin lispro 100 IU/mL+14.6 mg of substituted citrate A1
E: insulin lispro+EDTA at 300 µM

FIG. 13 describes, on the ordinate, the CD signal at 240 nm (deg·cm$^2$·dmol$^{-1}$) and, on the abscissa:
A: insulin lispro 100 IU/mL
D: insulin lispro 100 IU/mL+7.3 mg/mL of substituted citrate A3
D': insulin lispro 100 IU/mL+7.3 mg/mL of substituted citrate A3 and citrate at 9.3 mM
E: insulin lispro+EDTA at 300 µM
FIG. 14 describes, on the ordinate, the CD signal at 240 nm (deg·cm$^2$·dmol$^{-1}$) and, on the abscissa:
A: insulin lispro 100 IU/mL
E: insulin lispro+EDTA at 300 µM
G: insulin lispro 100 IU/mL+14.6 mg/mL of substituted citrate A3

FIG. 15 describes, on the ordinate, the CD signal at 240 nm (deg·cm$^2$·dmol$^{-1}$) and, on the abscissa:
A: human insulin 100 IU/mL
B: human insulin 100 IU/mL+7.3 mg/ml of substituted citrate A3
C: human insulin 100 IU/mL+7.3 mg/ml of substituted citrate A3 and citrate at 9.3 mM
D: human insulin 100 IU/mL+EDTA at 300 µM
D': human insulin 100 IU/mL+EDTA at 6 mM
FIG. 16 describes, on the ordinate, the CD signal at 240 nm (deg·cm$^2$·dmol$^{-1}$) and, on the abscissa:
A: human insulin 100 IU/mL (Humulin® R)
B: human insulin 100 IU/mL+EDTA at 300 µM
B': human insulin 100 IU/mL+EDTA at 6 mM
C: human insulin 100 IU/mL+14.6 mg/mL of substituted citrate A3.

EXAMPLES

Figure 1:
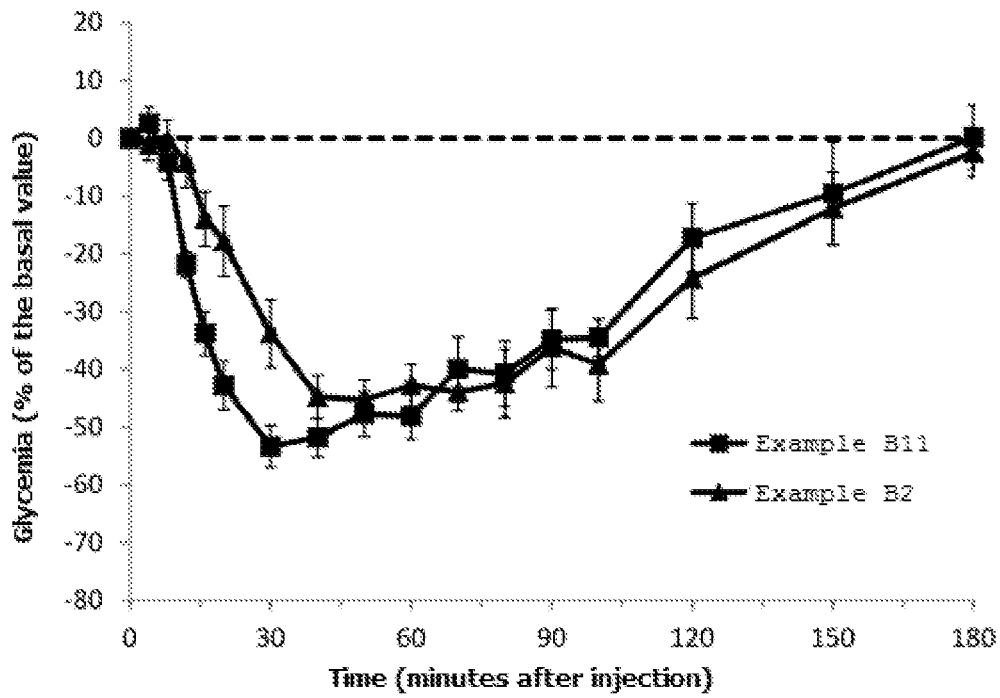
FIG. 1: Glycemia (% of the basal value) as a function of time (minutes after injection). The analysis of these curves shows that the composition of Example B11 comprising the substituted citrate A1 and the citrate as excipient (curve plotted with squares corresponding to Example B11, Tmin glucose=44±18 min and T50% Rmin glucose=15±3 min) makes it possible to obtain a more rapid action than that of the commercial composition Humalog® of Example B2 (curved plotted with triangles corresponding to Example B2, Tmin glucose=61±23 min and T50% Rmin glucose=26±9 min).

Table 1 below presents, in a nonlimiting manner, examples of compounds according to the invention.

TABLE 1

| Substituted citrates | Formulas |
|---|---|
| A1 | (structure: citrate with one phenylalanine amide, two NaO carboxylates, central HO) |
| A2 | (structure: citrate with one phenylalanine amide at bottom, two NaO carboxylates at top, central HO) |
| A3 | (structure: citrate with two phenylalanine amides and one NaO carboxylate, central HO) |
| A4 | (structure: citrate with three phenylalanine amides, central HO) |

TABLE 2

Counter-examples

| Compounds of the prior art | Formulas | CAS Name Origin |
|---|---|---|
| CE1 | (structure of N-Carbobenzoxy-L-phenylalanyl-L-phenylalanine) | CAS: 13122-91-3<br>N-Carbobenzoxy-L-phenylalanyl-L-phenylalanine<br>Supplier: TCI |

TABLE 2-continued

Counter-examples

| Compounds of the prior art | Formulas | CAS Name Origin |
|---|---|---|
| CE2 | (structure of Benzoyl-L-phenylalanine) | CAS: 2566-22-5 Benzoyl-L-phenylalanine Supplier: BACHEM |

Example A1: Substituted Citrate A1

Molecule 1: 1,3-dimethyl acid citrate

A solution of citric acid (50 g, 260 mmol), of boric acid (1.5 g, 24.7 mmol) in 70 mL of methanol and 80 mL of acetone is stirred at ambient temperature for 3 days. Acetone (80 mL) is added to the reaction medium which is cooled to 0° C. for 2 h. The solid is recovered by filtration through a frit, washed with an acetone/dichloromethane mixture (1/1), and dried under a vacuum.

Yield: 48.8 g (85%)

$^1$H NMR (DMSO-$d_6$, ppm): 2.74 (2H); 2.85 (2H); 3.56 (6H).

LC/MS (ESI): 221.2; (calculated ([M+H]$^+$): 221.2)

Molecule 2: Product Obtained by the Reaction Between Molecule 1 and the L-Phenylalanine Ethyl Ester Hydrochloride Salt To a solution of molecule 1 (25 g, 113.5 mmol) in tetrahydrofuran (THF) (1.1 L) at 0° C., dicyclochlohexyl carbodiimide (DCC) (24.6 g, 119.2 mmol) and N-hydroxysuccinimide (NHS) (13.72 g, 119.2 mmol) are added successively. After 16 h of stirring at ambient temperature, the medium is cooled to 0° C. for 20 min, filtered through a frit, and added to a suspension of L-phenylalanine ethyl ester hydrochloride salt (26.8 g, 113.5 mmol) and of triethylamine (110.8 mL, 794.8 mmol) in THF (150 mL), 50 mL are added to obtain a homogeneous medium, and the solution is stirred at ambient temperature for 1 h. The medium is evaporated under a vacuum, diluted with ethyl acetate, and washed with a saturated aqueous solution of NaHCO$_3$. The aqueous phase is extracted with ethyl acetate. The combined organic phases are washed with a 10% aqueous solution of HCl, then a saturated aqueous solution of NaCl. After drying over Na$_2$SO$_4$, the organic phase is filtered, concentrated under a vacuum, and the residue is purified by flash chromatography (cyclohexane, ethyl acetate) to yield a colorless oil.

Yield: 20.4 g (45%)

$^1$H NMR (DMSO-$d_6$, ppm): 1.26 (3H); 2.78-2.90 (4H); 3.14 (2H); 3.70 (6H); 4.15 (2H); 4.82 (1H); 4.93 (1H); 7.20-7.33 (5H); 7.40 (1H).

LC/MS (ESI): 396.3; (calculated [N+H]$^+$): 396.4).

Substituted Citrate A1

To a solution of molecule 2 (20.34 g, 51.44 mmol) in methanol (514 mL) at 0° C., a 2N aqueous solution of soda (128.6 mL) is added. The mixture is stirred at 0° C. for 2 h, then at ambient temperature for 2 h. An additional 25.7 mL of 2N soda are added, and the mixture is stirred at ambient temperature for 2 h. The solid form is filtered through a frit, azeotroped with water (150 mL), and dried under a vacuum to yield a white solid of substituted citrate A1. Yield: 13.6 g (64%)

$^1$H NMR (DMSO-$d_6$, ppm): 1.95-2.65 (4H); 2.99 (1H); 3.20 (1H); 4.49 (1H); 7.30-7.42 (5H).

LC/MS (ESI): 340.1; (calculated [M+4H−3Na]$^+$): 340.2).

Example A2: Substituted Citrate A2

Molecule 3: Tert-Butyl Ester of Molecule 1

To a solution of molecule 1 (7 g, 31.8 mmol) in dichloromethane (318 mL) at ambient temperature, tert-butyl-2,2,2-trichloroacetimidate (9.3 mL) is added. After 16 h of stirring, an additional portion of tert-butyl-2,2,2-trichloroacetimidate (3.09 mL) is added. After 6 h of stirring, an additional portion of tert-butyl-2,2,2-trichloroacetimidate (3.09 mL) is added. After 16 h of stirring, the mixture is evaporated to dryness under a vacuum to yield a solid, which is dissolved in hexane (100 mL). The suspension is stirred hot for 30 min, cooled to 5° C., and filtered through a frit. The solid is rinsed with dichloromethane (50 mL), and the filtrate is evaporated under a vacuum to yield an oil, which is purified by flash chromatography (cyclohexane, ethyl acetate).

Yield: 4.76 g (50%)

$^1$H NMR (CDCl$_3$, ppm): 1.48 (9H); 2.70-2.86 (4H); 3.67 (6H); 4.02 (1H).

$^{13}$C NMR (CDCl$_3$, ppm): 27.67; 43.27; 51.75; 72.98; 83.22; 170.04; 172.23.

Molecule 4: Product Obtained by Saponification of Molecule 3

To a solution of molecule 3 (3.35 g, 12.13 mmol) in methanol (120 mL) at 0° C., a 2N aqueous solution of soda (18.2 mL), cooled beforehand to 0° C., is added. The medium is stirred at 0° C. for 15 min, then at ambient temperature for 5 h. After evaporation of the organic phase under a vacuum, the medium is diluted with water (50 mL), and the aqueous phase is washed with ethyl acetate (100 mL), then acidified with a 10% aqueous solution of HCl and extracted with ethyl acetate (2×150 mL). The organic phase is washed with water (100 mL), a saturated aqueous solution of NaCl (150 mL), then dried over Na$_2$SO$_4$, filtered and evaporated under a vacuum, to yield a white solid. The aqueous phase is extracted again with ethyl acetate (2×150 mL), dried over Na$_2$SO$_4$, filtered and evaporated under a vacuum to yield a second portion of the desired product.

Yield: 15.6 g (86%)

$^1$H NMR (CD$_3$OD, ppm): 1.46 (9H); 2.71 (2H); 2.86 (2H).

LC/MS (ESI): 247.1; (calculated ([M−H]−): 247.3).

Molecule 5: Product Obtained by the Reaction Between Molecule 4 and DCC

To a solution of molecule 4 (15.6 g, 62.8 mmol) in a dichloromethane/THF mixture (310/100 mL), DCC (14.26 g, 69.1 mmol) is added, and the medium is stirred for 5 h at ambient temperature. After filtration through celite, the medium is evaporated to dryness. The residue is stirred hot in a hexane/ethyl acetate mixture (320/80 mL), then cooled to −20° C. overnight. After filtration through a frit, an orangish solid is isolated.

Yield: 13.3 g (91%)

$^1$H NMR (CDCl$_3$, ppm): 1.50 (9H); 2.94 (2H); 3.03 (2H).

Molecule 6: Product Obtained by the Reaction Between Molecule 5 and the L-Phenylalanine Tert-Butyl Ester Hydrochloride Salt To a solution of L-phenylalanine tert-butyl ester hydrochloride salt (16.4 g, 63.55 mmol) in dichlormethane (100 mL), a saturated aqueous solution of NaHCO$_3$ (150 mL) is added. The organic phase is separated, and the aqueous phase is extracted with dichloromethane (50 mL). The combined organic phases are dried over Na$_2$SO$_4$, filtered and partially concentrated under a vacuum to a volume of 40 mL. The solution obtained is poured onto a solution of molecule 5 (13.3 g, 57.8 mmol) in THF (577 mL) at 0° C. After 3 h of stirring at 0° C., the medium is concentrated under a vacuum. The residue is dissolved in ethyl acetate (200 mL), filtered through a PTFE membrane (0.45 µm), washed with a saturated aqueous solution of NH$_4$Cl (100 mL), water (100 mL), and a saturated aqueous solution of NaCl (100 mL). After drying over Na$_2$SO$_4$ and filtration, the organic phase is evaporated under a vacuum. The residue is purified by flash chromatography (cyclohexane, ethyl acetate). The oil obtained is azeotroped with water and with acetone to yield a beige solid.

Yield: 24.3 g (93%)

$^1$H NMR (CDCl$_3$, ppm): 1.40 (9H); 1.45 (9H); 2.60-2.85 (4H); 3.08 (2H); 4.73 (1H); 6.73 (1H); 7.15-7.30 (5H).

LC/MS (ESI): 453.2; (calculated ([M+H]$^+$): 452.5).

Substituted Citrate A2

To a solution of molecule 6 (24.3 g, 53.8 mmol) in dichloromethane (110 mL) at 0° C., trifluoroacetic acid (TFA) (82.4 mL) is added. The temperature of the mixture is allowed to rise to ambient temperature and stirred for 5 h. After evaporation to dryness under a vacuum, the residue is dissolved in ethyl acetate (100 mL), cooled to −20° C. for 1 h, and filtered through a PVDF membrane (0.45 µm). The filtrate is concentrated under a vacuum to yield the substituted citrate A2 in acid form.

Yield: 18.4 g (quantitative)

$^1$H NMR (DMSO-d$_6$, ppm): 2.50-2.65 (4H); 2.90 (1H); 3.02 (1H); 4.43 (1H); 7.20-7.30 (5H); 8.24 (1H).

LC/MS (ESI): 338.0; (calculated ([M−H]−): 338.3).

To a suspension of substituted citrate A2 in acid form (18.2 g, 53.6 mmol) in 250 mL of water, a 2N aqueous solution of soda (80.5 mL) is added dropwise. The solution is evaporated. The residue is dissolved in water at reflux (40 mL), then ethanol (400 mL) is added. The medium which forms lumps is stirred with heating for 15 min, then cooled in an ice bath. The precipitate is recovered by filtration through a frit, then dissolved in water to yield a solid. After 3 water/ethanol/filtration treatments, a white solid of substituted citrate A2 is obtained.

Yield: 11.74 g (54%)

$^1$H NMR (D$_2$O, ppm): 2.10-2.70 (4H); 2.90 (1H); 3.02 (1H); 3.16 (1H); 4.48 (1h); 7.32-7.42 (5H).

Example A3: Substituted Citrate A3

Molecule 7: Product Obtained by the Reaction Between Molecule 4 and the L-Phenylalanine Tert-Butyl Ester Hydrochloride Salt To a solution of molecule 4 (1.0 g, 4.03 mmol) in THF (40 mL), DCC (2.49 g, 12.09 mmol) and NHS (1.27 g, 11.08 mmol) are added successively. After 4 h of stirring at ambient temperature, the medium is evaporated under a vacuum to yield a solid, which is dissolved in anhydrous dioxane and cooled to 0° C.

The L-phenylalanine tert-butyl ester hydrochloride salt (2.28 g, 8.85 mmol) is dissolved in a dichloromethane/ saturated aqueous solution of NaHCO$_3$ mixture (15/20 mL). After separation of the phases, the aqueous phase is extracted with dichloromethane. The organic phases are dried over Na$_2$SO$_4$ and filtered. The solution obtained is added dropwise to the solution of molecule 4 activated at 0° C. The mixture is allowed to return to ambient temperature and stirred for 16 h. Three additional equivalents of free amine prepared as above in 20 mL of dichloromethane are then added at 24 h interval. The reaction medium is filtered through a frit, and the organic solvents are evaporated under a vacuum. The medium is diluted with ethyl acetate (100 mL), washed with a 10% aqueous solution of HCl (50 mL), a saturated aqueous solution of NaHCO$_3$ (50 mL), and a saturated aqueous solution of NaCl (50 mL). After drying over Na$_2$SO$_4$, the organic phase is filtered and concentrated under a vacuum to yield an oil. The residue is purified by flash chromatography (cyclohexane, ethyl acetate) to yield a yellow oil, which is dissolved in ethyl acetate (20 mL). The solution is cooled to −20° C. for 1 h, filtered through a PVDF membrane (0.45 µm). The filtrate is evaporated under a vacuum to yield a yellow lacquer.

Yield: 1.84 g (70%)

$^1$H NMR (CDCl$_3$, ppm): 1.43 (18H); 1.47 (9H); 2.49 (1H); 2.60 (3H); 2.95-3.10 (4H); 4.68 (2H); 5.02 (1H); 7.13 (1H); 7.19-7.30 (12H).

LC/MS (ESI): 655.5; (calculated ([M+H]$^+$): 655.8).

Substituted Citrate A3

To a solution of molecule 7 (1.72 g, 2.63 mmol) in dichloromethane (13 mL) at 0° C., TFA (5.7 mL) is added. The temperature of the medium is allowed to rise again to ambient temperature and is stirred for 5 h. The medium is cooled to −20° C. overnight, then returned to ambient temperature, and an additional 2 mL of TFA are added. After 1 h of stirring and evaporation under a vacuum at 30° C., the medium is azeotroped with water (50 mL). The residue is dissolved in ethyl acetate (20 mL), and the organic phase is extracted with a 1 N aqueous solution of soda (20 mL). The aqueous phase is acidified with a 10% aqueous solution of HCl and extracted with ethyl acetate (30 mL). The organic phase is washed with water (25 mL), a saturated aqueous solution of NaCl (2×25 mL), dried over Na$_2$SO$_4$, filtered and evaporated under a vacuum to yield the substituted citrate A3 in acid form.

Yield: 0.83 g (64%)

$^1$H NMR (DMSO-d$_6$, ppm): 2.44-2.56 (4H); 2.87 (2H); 2.99 (2H); 4.41 (2H); 7.19-7.30 (10H); 8.19 (2H).

LC/MS (ESI): 487.2; (calculated ([M+H]$^+$): 487.5).

After an azeotrope with water (2×50 mL), the substituted citrate A3 in acid form (828 mg, 1.7 mmol) is dissolved in 50 mL of water, and a 2N soda solution is added dropwise until the pH is 7.27. The solution is evaporated to dryness, and the solid obtained is triturated in an ethanol/water mixture (10/1 mL) with heating for 30 min. After cooling by means of an ice bath, the suspension is filtered through a frit. The solid obtained is azeotroped in water (150 mL). After drying under a vacuum, the solid is dissolved in 2.5 mL of hot water, then 25 mL of ethanol are added with heating. After cooling at −20° C. for 1 h, the precipitate formed is recovered by filtration through a frit and azeotroped in water (50 mL). After drying under a bell jar (16 h, 55° C., 0.2 mbar), a white solid of substituted citrate A3 is obtained.

Yield: 396 mg (42%)

$^1$H NMR (D$_2$O, ppm): 2.22-2.31 (2H); 2.50 (2H); 2.94-3.01 (2H); 3.20 (2H); 4.48 (2H); 7.26-7.39 (10H).

Example A4: Substituted Citrate A4

Molecule 8: Product Obtained by the Reaction Between Citric Acid and the L-Phenylalanine Ethyl Ester Hydrochloride Salt To a solution of citric acid (1.0 g, 5.20 mmol) in N,N-dimethylformamide (DMF) (50 mL), diisopropylethylamine (DIPEA) (2.69 g, 20.8 mmol), 1-ethyl-3-(3-dimethylaminopropyl)carbodiimide hydrochloride salt (EDCI.HCl) (3.29 g, 17.18 mmol), and 2-hydroxypyridine-N-oxide (HOPO) (1.82 g, 16.4 mmol) are successively added. After 5 min of stirring, the L-phenylalanine ethyl ester hydrochloride salt (3.95 g, 17.18 mmol) is added, and the reaction medium is stirred at ambient temperature. After 16 h of stirring, the DMF is evaporated under a vacuum. The residue is diluted in ethyl acetate (250 mL) and washed with a saturated aqueous solution of NaHCO$_3$ (2×120 mL). The phases are separated. The aqueous phase is washed with ethyl acetate (50 mL). The combined organic phases are washed with a 1N aqueous solution of HCl (120 mL), water (2×120 mL), a saturated aqueous solution of NaCl (120 mL). After drying over Na$_2$SO$_4$, the organic phase is filtered and concentrated under a vacuum. The residue is purified by flash chromatography (cyclohexane, ethyl acetate) to yield a white solid after evaporation under a vacuum followed by an azeotrope with dichloromethane two times.

Yield: 2.49 g (66%)

$^1$H NMR (CDCl$_3$, ppm): 1.21 (9H); 2.47 (1H); 2.58 (3H); 3.03 (6H); 4.14 (6H); 4.75 (3H); 6.09 (1H); 6.86 (2H); 7.14 (6H); 7.20-7.35 (9H); 7.50 (1H).

LC/MS (ESI): 718.6; (calculated ([M+H]$^+$): 718.8.

Substituted Citrate A4

To a solution of molecule 8 (2.77 g, 3.86 mmol) in a THF/methanol mixture (1/1, 26 mL) cooled to 0° C., a solution of lithium hydroxide hydrate (LiOH.H$_2$O) (0.57 g, 13.51 mmol) in water (13 mL) is added. The reaction medium is stirred at 0° C. After 3 h of stirring, the solvents are evaporated under a vacuum, and the aqueous residue is acidified until the pH is 1 by adding a 1N aqueous solution of HCl. The aqueous phase is extracted with methyl tert-butyl ether (MTBE) (4×20 mL). The organic phases are pooled, washed with a saturated aqueous solution of NaCl (20 mL), dried over Na$_2$SO$_4$, filtered and concentrated under a vacuum. The residue is dissolved in acetonitrile (120 mL) and co-evaporated with MTBE to yield a white solid of substituted citrate A4 in acid form after drying under a vacuum.

Yield: 2.35 g (66%)

$^1$H NMR (DMSO-d$_6$, ppm): 2.34-2.49 (4H); 2.85 (2H); 2.97 (4H); 4.42 (3H); 6.25 (1H); 7.15-7.21 (15H); 7.58 (1H); 8.19 (1H); 0.8.24 (1H); 12.77 (3H).

LC/MS (ESI): 634.5; (calculated ([M+H]$^+$): 634.6).

To a solution of substituted citrate A4 in acid form (2.35 g, 3.71 mmol) in water (100 mL), a 2M aqueous solution of soda is added dropwise until the pH is 7.04. The solution is then filtered through a 0.22 μm nitrocellulose membrane, frozen and lyophilized to yield a white solid of substituted citrate A4.

Yield: 2.57 g (99%)

$^1$H NMR (D$_2$O, ppm): 1.94 (1H); 2.35 (2H); 2.54 (1H); 2.88-3.13 (5H); 3.20 (1H); 4.37-4.43 (2H); 4.50 (1H); 7.18-7.36 (15H).

Part B: Preparation of the Solutions

B1. Solution of: Rapid Insulin Analog Novolog® at 100 IU/mL

This solution is a commercial solution of insulin aspart from Novo Nordisk sold under the name of Novolog®. This product is a rapid insulin analog.

B2. Solution of Rapid Insulin Analog Humalog® at 100 IU/mL

This solution is a commercial solution of insulin lispro from Eli Lilly sold under the name of Humalog® U100. This product is a rapid insulin analog. In the present text, when the term Humalog is used without other specification, it refers to Humalog® r U100, and when the expression "the commercial formulation of insulin lispro" is used without other specification, it refers to the commercial formulation of insulin lispro at 100 IU/mL.

B3. Solution of Human Insulin Humulin® R at 100 IU/mL

This solution is a commercial solution of human insulin from Eli Lilly sold under the name of Humulin® R. This product is a composition of human insulin.

B4. Solution of rapid insulin analog Apidra® at 100 IU/mL

This solution is a commercial solution of insulin glulisine from Sanofi sold under the name of Apidra®. This product is a rapid insulin analog.

B5. Preparation of a Solution of Sodium Citrate at 1.188 M

The solution of sodium citrate is obtained by dissolving 9.0811 g of sodium citrate (30.9 mmol) in 25 mL of water in a graduated flask. The pH is adjusted to 7.4 by adding 1 mL of 1M HCl. The solution is filtered through 0.22 μm.

B6. Preparation of a Solution of Insulin Analog (Insulin Lispro) at 200 IU/mL.

The commercial formulation of insulin lispro (Humalog® U100) was concentrated using AMICON Ultra-15 centrifugation tubes with a cutoff of 3 kDa. The amicon tubes were first rinsed with 12 mL of deionized water, 12 mL of the commercial formulation were centrifuged for 35 minutes at 4000 g at 20° C. The volume of the retentate was measured, and the concentration was estimated in this way. All the retentates were pooled, and the overall concentration was estimated (>200 IU/mL).

The concentration of this concentrated solution of insulin lispro was adjusted to 200 IU/mL by adding the commercial formulation of insulin lispro (Humalog®). The concentrated formulation of insulin lispro has the same concentrations of excipients (m-cresol, glycerol, phosphate) as the commercial formulation at 100 IU/mL.

The final pH is adjusted to 7.4±0.4. The clear solution is filtered through a 0.22 μm membrane and stored at 4° C.

B7. Preparation of a Solution of Human Insulin at 200 IU/mL.

The commercial formulation of human insulin (Humulin® R) was concentrated using AMICON Ultra-15 centrifugation tubes with a cutoff of 3 kDa. The amicon tubes were first rinsed with 12 mL of deionized water. 12 mL of the commercial formulation were centrifuged for 35 minutes at 4000 g at 20° C. The volume of the retentate was measured, and the concentration was estimated in this way. All the retentates were pooled, and the overall concentration was estimated (>200 IU/mL).

The concentration of this concentrated solution of human insulin was adjusted to 200 IU/mL by adding the commercial formulation of human insulin (Humulin® R). The concentrated formulation of human insulin has the same concentrations of excipients (m-cresol, glycerol) as the commercial formulation at 100 IU/mL.

The final pH is adjusted to 7.4±0.4. The clear solution is filtered through a 0.22 m membrane and stored at 4° C.

B8. Preparation of a Solution of Insulin Aspart at 200 IU/mL.

The commercial formulation of insulin aspart (Novolog®) was concentrated using AMICON Ultra-15 centrifugation tubes with a cutoff of 3 kDa. The amicon tubes were first rinsed with 12 mL of deionized water. 12 mL of the commercial formulation were centrifuged for 35 minutes at 4000 g at 20° C. The volume of the retentate was measured, and the concentration was estimated in this way. All the retentates were pooled, and the overall concentration was estimated (>200 IU/mL).

The concentration of this concentrated solution of insulin aspart was adjusted to 200 IU/mL by adding the commercial formulation of insulin aspart (Novolog®). The concentrated formulation of concentrated insulin aspart has the same concentrations of excipients (m-cresol, glycerol) as the commercial formulation at 100 IU/mL.

The final pH is adjusted to 7.4±0.4. The clear solution is filtered through a 0.22 m membrane and stored at 4° C.

B9. Preparation of a Solution of Insulin Glulisine at 200 IU/mL.

The commercial formulation of insulin glulisine (Apidra®) was concentrated using AMICON Ultra-15 centrifugation tubes with a cutoff of 3 kDa. The amicon tubes were first rinsed with 12 mL of deionized water. 12 mL of the commercial formulation were centrifuged for 35 minutes at 4000 g at 20° C. The volume of the retentate was measured, and the concentration was estimated in this way. All the retentates were pooled, and the overall concentration was estimated (>200 IU/mL).

The concentration of this concentrated solution of insulin glulisine was adjusted to 200 IU/mL by adding the commercial formulation of insulin glulisine (Apidra®). The concentrated formulation of insulin glulisine has the same concentrations of excipients (m-cresol, NaCl, TRIS) as the commercial formulation at 100 IU/mL.

The final pH is adjusted to 7.4±0.4. The clear solution is filtered through a 0.22 μm membrane and stored at 4° C.

B10. Preparation of a Solution of Human Insulin, of Insulin Lispro, of Insulin Aspart or of Insulin Glulisine at 300, 400 and 500 IU/mL.

The concentrated formulations of human insulin, of insulin lispro, of insulin aspart or of insulin glulisine at 300 IU/mL, 400 IU/mL or 500 IU/mL (as well as at all the intermediate concentrations) are prepared based on the protocol of Example B9 pertaining to the preparation of a solution of insulin glulisine at 200 IU/mL. The commercial formulation of insulin is concentrated using AMICON Ultra-15 centrifugation tubes with a cutoff of 3 kDa. The amicon tubes are first rinsed with 12 mL of deionized water. 12 mL of the commercial formulation are centrifuged at 4000 g and at 20° C. By varying the centrifugation time, it is possible to adjust the final volume and thus the final concentration of insulin in the formulation. The volume of the retentate is measured, and the concentration is estimated in this way. All the retentates are pooled, and the overall concentration is estimated (>300, 400 or 500 IU/mL).

The concentration of this concentrated solution of insulin is adjusted to the desired concentration (e.g., 300 IU/mL, 400 IU/mL or 500 IU/mL) by adding the formulation of insulin (Humulin® R, Novolog®, Humalog® or Apidra®). The concentrated formulation of concentrated insulin has the same concentrations of excipients as the commercial formulation at 100 IU/mL.

The final pH is adjusted to 7.4±0.4. The clear solution is filtered through a 0.22 μm membrane and stored at 4° C.

B11. Preparation of a Solution of Insulin Lispro at 100 IU/mL in the Presence of the Substituted Citrate A1 and of Citrate For a final volume of 100 mL of composition, with a mass ratio [substituted citrate A1]/[insulin lispro] of 2.0 and a concentration of 9.3 mM of citrate, the different reagents are added in the quantities specified below and in the following order:

| Lyophilized compound (substituted citrate A1) | 730 mg |
| Commercial solution of Humalog ® | 100 mL |
| Solution of sodium citrate at 1.188M | 783 μL |

The final pH is adjusted to 7.4±0.4.

The clear solution is filtered through a 0.22 μm membrane and stored at 4° C.

B12. Preparation of a Solution of Human Insulin at 100 IU/mL in the Presence of the Substituted Citrate A1 and of Citrate For a final volume of 100 mL of composition, with a mass ratio [substituted citrate A1]/[human insulin] of 2.0 and a concentration of 9.3 mM of citrate, the different reagents are added in the quantities specified below and in the following order:

| Lyophilized compound (substituted citrate A1) | 730 mg |
| Commercial solution of Humulin ® R | 100 mL |
| Solution of sodium citrate at 1.188M | 783 μL |

The final pH is adjusted to 7.4±0.4.

The clear solution is filtered through a 0.22 μm membrane and stored at 4° C.

B13. Preparation of a Solution of Insulin Aspart at 100 IU/mL in the Presence of the Substituted Citrate A1 and of Citrate For a final volume of 100 mL of composition, with a mass ratio [substituted citrate A1]/[insulin aspart] of 2.0 and a concentration of 9.3 mM of citrate, the different reagents are added in the quantities specified below and in the following order:

| Lyophilized compound (substituted citrate A1) | 730 mg |
| Commercial solution of Novolog ® | 100 mL |
| Solution of sodium citrate at 1.188M | 783 μL |

The final pH is adjusted to 7.4±0.4. The clear solution is filtered through a 0.22 μm membrane and stored at 4° C.

B14. Preparation of a Solution of Insulin Glulisine at 100 IU/mL in the Presence of the Substituted Citrate A1 and of Citrate For a final volume of 100 mL of composition, with a mass ratio [substituted citrate A1]/[insulin glulisine] of 2.0 and a concentration of 9.3 mM of citrate, the different reagents are added in the quantities specified below and in the following order:

| | |
|---|---|
| Lyophilized compound (substituted citrate A1) | 730 mg |
| Commercial solution of Apidra ® | 100 mL |
| Solution of sodium citrate at 1.188M | 783 µL |

The final pH is adjusted to 7.4±0.4.
The clear solution is filtered through a 0.22 µm membrane and stored at 4° C.

B15. Preparation of a Solution of Insulin Lispro at 200 IU/mL in the Presence of the Substituted Citrate A1 and of Citrate.

For a final volume of 100 mL of formulation, with a mass ratio [substituted citrate A1]/[insulin lispro] of 2 and a concentration of 18.6 mM of citrate, the different reagents are added in the quantities specified below and in the following order:

| | |
|---|---|
| Lyophilized compound (substituted citrate A1) | 1460 mg |
| Insulin lispro at 200 IU/mL | 100 mL |
| Solution of sodium citrate at 1.188M | 1566 µL |

The final pH is adjusted to 7.4±0.4. The clear solution is filtered through a 0.22 µm membrane and stored at 4° C.

B16. Preparation of a Solution of Human Insulin at 200 IU/mL in the Presence of the Substituted Citrate A1 and of Citrate.

For a final volume of 100 mL of formulation, with a mass ratio [substituted citrate A1]/[human insulin] of 2 and a concentration of 18.6 mM of citrate, the different reagents are added in quantities specified below and in the following order:

| | |
|---|---|
| Lyophilized compound (substituted citrate A1) | 1460 mg |
| Human insulin at 200 IU/mL | 100 mL |
| Solution of sodium citrate at 1.188M | 1566 µL |

The final pH is adjusted to 7.4±0.4. The clear solution is filtered through a 0.22 µm membrane and stored at 4° C.

B17. Preparation of a Solution of Insulin Aspart at 200 IU/mL in the Presence of the Substituted Citrate A1 and of Citrate.

For a final volume of 100 mL of formulation, with a mass ratio [substituted citrate A1]/[insulin aspart] of 2 and a concentration of 18.6 mM of citrate, the different reagents are added in quantities specified below and in the following order:

| | |
|---|---|
| Lyophilized compound (substituted citrate A1) | 1460 mg |
| Insulin aspart at 200 IU/mL | 100 mL |
| Solution of sodium citrate at 1.188M | 1566 µL |

The final pH is adjusted to 7.4±0.4. The clear solution is filtered through a 0.22 µm membrane and stored at 4° C.

B18. Preparation of a solution of insulin glulisine at 200 IU/mL in the presence of the substituted citrate A1 and of citrate.

For a final volume of 100 mL of formulation, with a mass ratio [substituted citrate A1]/[insulin glulisine] of 2 and a concentration of 18.6 mM of citrate, the different reagents are added in quantities specified below and in the following order:

| | |
|---|---|
| Lyophilized compound (substituted citrate A1) | 1460 mg |
| Insulin glulisine at 200 IU/mL | 100 mL |
| Solution of sodium citrate at 1.188M | 1566 µL |

The final pH is adjusted to 7.4±0.4. The clear solution is filtered through a 0.22 µm membrane and stored at 4° C.

B19. Preparation of a Solution of Insulin Lispro at 300 IU/mL in the Presence of the Substituted Citrate A1 and of Citrate.

For a final volume of 100 mL of formulation, with a mass ratio [substituted citrate A1]/[insulin lispro] of 2.0 and a concentration of 27.9 mM of citrate, the different reagents are added in quantities specified below and in the following order:

| | |
|---|---|
| Lyophilized compound (substituted citrate A1) | 2190 mg |
| Insulin lispro at 300 IU/mL | 100 mL |
| Sodium citrate | 720 mg |

The final pH is adjusted to 7.4±0.4. The clear solution is filtered through a 0.22 µm membrane and stored at 4° C.

B20. Preparation of a Solution of Human Insulin at 300 IU/mL in the Presence of the Substituted Citrate A1 and of Citrate.

For a final volume of 100 mL of formulation, with a mass ratio [substituted citrate A1]/[human insulin] of 2.0 and a concentration of 27.9 mM of citrate, the different reagents are added in quantities specified below and in the following order:

| | |
|---|---|
| Lyophilized compound (substituted citrate A1) | 2190 mg |
| Human insulin at 300 IU/mL | 100 mL |
| Sodium citrate | 720 mg |

The final pH is adjusted to 7.4±0.4. The clear solution is filtered through a 0.22 m membrane and stored at 4° C.

B21. Preparation of a Solution of Insulin Lispro at 400 IU/mL in the Presence of the Substituted Citrate A1 and of Citrate.

For a final volume of 100 mL of formulation, with a mass ratio [substituted citrate A1]/[insulin lispro] of 2.0 and a concentration of 37.2 mM of citrate, the different reagents are added in quantities specified below and in the following order:

| | |
|---|---|
| Lyophilized compound (substituted citrate A1) | 2920 mg |
| Insulin lispro at 400 IU/mL | 100 mL |
| Sodium citrate | 960 mg |

The final pH is adjusted to 7.4±0.4. The clear solution is filtered through a 0.22 µm membrane and stored at 4° C.

B22. Preparation of a Solution of Human Insulin at 400 IU/mL in the Presence of the Substituted Citrate A1 and of Citrate.

For a final volume of 100 mL of formulation, with a mass ratio [substituted citrate A1]/[human insulin] of 2.0 and a concentration of 37.2 mM of citrate, the different reagents are added in quantities specified below and in the following order:

| Lyophilized compound (substituted citrate A1) | 2920 mg |
| Human insulin at 400 IU/mL | 100 mL |
| Sodium citrate | 960 mg |

The final pH is adjusted to 7.4±0.4. The clear solution is filtered through a 0.22 μm membrane and stored at 4° C.

B23. Preparation of a Solution of Insulin Lispro at 500 IU/mL in the Presence of the Substituted Citrate A1 and of Citrate.

For a final volume of 100 mL of formulation, with a mass ratio [substituted citrate A1]/[insulin lispro] of 2.0 and a concentration of 46.5 mM of citrate, the different reagents are added in the quantities specified below and in the following order:

| Lyophilized compound (substituted citrate A1) | 3650 mg |
| Insulin lispro at 500 IU/mL | 100 mL |
| Sodium citrate | 1200 mg |

The final pH is adjusted to 7.4±0.4. The clear solution is filtered through a 0.22 μm membrane and stored at 4° C.

B24. Preparation of a Solution of Human Insulin at 500 IU/mL in the Presence of the Substituted Citrate A1 and of Citrate.

For a final volume of 100 mL of formulation, with a mass ratio [substituted citrate A1]/[human insulin] of 2.0 and a concentration of 46.5 mM of citrate, the different reagents are added in quantities specified below and in the following order:

| Lyophilized compound (substituted citrate A1) | 3650 mg |
| Human insulin at 500 IU/mL | 100 mL |
| Sodium citrate | 1200 mg |

The final pH is adjusted to 7.4±0.4. The clear solution is filtered through a 0.22 μm membrane and stored at 4° C.

B25. Preparation of a Solution of Insulin Aspart at 500 IU/mL in the Presence of the Substituted Citrate A1 and of Citrate.

For a final volume of 100 mL of formulation, with a mass ratio [substituted citrate A1]/[insulin aspart] of 2.0 and a concentration of 46.5 mM of citrate, the different reagents are added in quantities specified below and in the following order:

| Lyophilized compound (substituted citrate A1) | 3650 mg |
| Insulin aspart at 500 IU/mL | 100 mL |
| Sodium citrate | 1200 mg |

The final pH is adjusted to 7.4±0.4. The clear solution is filtered through a 0.22 μm membrane and stored at 4° C.

B26. Preparation of a Solution of Insulin Lispro at 100 IU/mL in the Presence of the Substituted Citrate A1 at 14.6 mg/mL.

For a final volume of 100 mL of composition, with a mass ratio [substituted citrate A1]/[insulin lispro] of 4.0, the different reagents are added in the quantities specified below and in the following order:

| Lyophilized compound (substituted citrate A1) | 1460 mg |
| Commercial solution of Humalog ® | 100 mL |

The final pH is adjusted to 7.4±0.4.
The clear solution is filtered through a 0.22 μm membrane and stored at 4° C.

B27. Preparation of a Solution of Human Insulin at 100 IU/mL in the Presence of the Substituted Citrate A1 at 14.6 mg/mL.

For a final volume of 100 mL of composition, with a mass ratio [substituted citrate A1]/[human insulin] of 4.0, the different reagents are added in the quantities specified below and in the following order:

| Lyophilized compound (substituted citrate A1) | 1460 mg |
| Commercial solution of Humulin ® R | 100 mL |

The final pH is adjusted to 7.4±0.4.
The clear solution is filtered through a 0.22 μm membrane and stored at 4° C.

B28. Preparation of a Solution of Insulin Aspart at 100 IU/mL in the Presence of the Substituted Citrate A1 at 14.6 mg/mL.

For a final volume of 100 mL of composition, with a mass ratio [substituted citrate A1]/[insulin aspart] of 4.0, the different reagents are added in the quantities specified below and in the following order:

| Lyophilized compound (substituted citrate A1) | 1460 mg |
| Commercial solution of Novolog ® | 100 mL |

The final pH is adjusted to 7.4±0.4.
The clear solution is filtered through a 0.22 μm membrane and stored at 4° C.

B29. Preparation of a Solution of Insulin Glulisine at 100 IU/mL in the Presence of the Substituted Citrate A1 at 14.6 mg/mL.

For a final volume of 100 mL of composition, with a mass ratio [substituted citrate A1]/[insulin glulisine] of 4.0, the different reagents are added in the quantities specified below and in the following order:

| Lyophilized compound (substituted citrate A1) | 1460 mg |
| Commercial solution of Apidra ® | 100 mL |

The final pH is adjusted to 7.4±0.4.
The clear solution is filtered through a 0.22 μm membrane and stored at 4° C.

B30. Preparation of a Solution of Insulin Lispro at 200 IU/mL in the Presence of the Substituted Citrate A1 at 29.2 mg/mL.

For a final volume of 100 mL of formulation with a mass ratio [substituted citrate A1]/[insulin lispro] of 4, the different reagents are added in the quantities specified below and in the following order:

| Lyophilized compound (substituted citrate A1) | 2920 mg |
| Insulin lispro at 200 IU/mL | 100 mL |

The final pH is adjusted to 7.4±0.4. The clear solution is filtered through a 0.22 μm membrane and stored at 4° C.

B31. Preparation of a Solution of Human Insulin at 200 IU/mL in the Presence of the Substituted Citrate A1 at 29.2 mg/mL.

For a final volume of 100 mL of formulation with a mass ratio [substituted citrate A1]/[human insulin] of 4, the different reagents are added in quantities specified below and in the following order:

| | |
|---|---|
| Lyophilized compound (substituted citrate A1) | 2920 mg |
| Human insulin at 200 IU/mL | 100 mL |

The final pH is adjusted to 7.4±0.4. The clear solution is filtered through a 0.22 μm membrane and stored at 4° C.

B32. Preparation of a Solution of Insulin Aspart at 200 IU/mL in the Presence of the Substituted Citrate A1 at 29.2 mg/mL.

For a final volume of 100 mL of formulation with a mass ratio [substituted citrate A1]/[insulin aspart] of 4.0, the different reagents are added in the quantities specified below and in the following order:

| | |
|---|---|
| Lyophilized compound (substituted citrate A1) | 2920 mg |
| Insulin aspart at 200 IU/mL | 100 mL |

The final pH is adjusted to 7.4±0.4. The clear solution is filtered through a 0.22 μm membrane and stored at 4° C.

B32. Preparation of a Solution of Insulin Lispro at 300 IU/mL in the Presence of the Substituted Citrate A1 at 43.8 mg/mL.

For a final volume of 100 mL of formulation with a mass ratio [substituted citrate A1]/[insulin lispro] of 4.0, the different reagents are added in quantities specified below and in the following order:

| | |
|---|---|
| Lyophilized compound (substituted citrate A1) | 4380 mg |
| Insulin lispro at 300 IU/mL | 100 mL |

The final pH is adjusted to 7.4±0.4. The clear solution is filtered through a 0.22 μm membrane and stored at 4° C.

B33 Preparation of a Solution of Human Insulin at 300 IU/mL in the Presence of the Substituted Citrate A1 at 43.8 mg/mL.

For a final volume of 100 mL of formulation with a mass ratio [substituted citrate A1]/[human insulin] of 4.0, the different reagents are added in quantities specified below and in the following order:

| | |
|---|---|
| Lyophilized compound (substituted citrate A1) | 4380 mg |
| Human insulin at 300 IU/mL | 100 mL |

The final pH is adjusted to 7.4±0.4. The clear solution is filtered through a 0.22 μm membrane and stored at 4° C.

B34. Preparation of a Solution of Insulin Lispro at 400 IU/mL in the Presence of the Substituted Citrate A1 at 58.4 mg/mL.

For a final volume of 100 mL of formulation with a mass ratio [substituted citrate A1]/[insulin lispro] of 4.0, the different reagents are added in quantities specified below and in the following order:

| | |
|---|---|
| Lyophilized compound (substituted citrate A1) | 5840 mg |
| Insulin lispro at 400 IU/mL | 100 mL |

The final pH is adjusted to 7.4±0.4. The clear solution is filtered through a 0.22 μm membrane and stored at 4° C.

B35. Preparation of a Solution of Human Insulin at 400 IU/mL in the Presence of the Substituted Citrate A1 at 58.4 mg/mL.

For a final volume of 100 mL of formulation with a mass ratio [substituted citrate A1]/[human insulin] of 4.0, the different reagents are added in quantities specified below and in the following order:

| | |
|---|---|
| Lyophilized compound (substituted citrate A1) | 5840 mg |
| Human insulin at 400 IU/mL | 100 mL |

The final pH is adjusted to 7.4±0.4. The clear solution is filtered through a 0.22 μm membrane and stored at 4° C.

B36. Preparation of a Solution of Insulin Lispro at 500 IU/mL in the Presence of the Substituted Citrate A1 at 73 mg/mL.

For a final volume of 100 mL of formulation with a mass ratio [substituted citrate A1]/[insulin lispro] of 4.0, the different reagents are added in quantities specified below and in the following order:

| | |
|---|---|
| Lyophilized compound (substituted citrate A1) | 7300 mg |
| Insulin lispro at 500 IU/mL | 100 mL |

The final pH is adjusted to 7.4±0.4. The clear solution is filtered through a 0.22 μm membrane and stored at 4° C.

B37. Preparation of a Solution of Human Insulin at 500 IU/mL in the Presence of the Substituted Citrate A1 at 73 mg/mL.

For a final volume of 100 mL of formulation with a mass ratio [substituted citrate A1]/[human insulin] of 4.0, the different reagents are added in quantities specified below and in the following order:

| | |
|---|---|
| Lyophilized compound (substituted citrate A1) | 7300 mg |
| Human insulin at 500 IU/mL | 100 mL |

The final pH is adjusted to 7.4±0.4. The clear solution is filtered through a 0.22 μm membrane and stored at 4° C.

B38. Preparation of a Solution of Insulin Aspart at 500 IU/mL in the Presence of the Substituted Citrate A1 at 73 mg/mL.

For a final volume of 100 mL of formulation with a mass ratio [substituted citrate A1]/[insulin aspart] of 4.0, the different reagents are added in quantities specified below and in the following order:

| | |
|---|---|
| Lyophilized compound (substituted citrate A1) | 7300 mg |
| Insulin aspart at 500 IU/mL | 100 mL |

The final pH is adjusted to 7.4±0.4.

The clear solution is filtered through a 0.22 μm membrane and stored at 4° C.

B39. Preparation of a Solution of Insulin Lispro at 100 IU/mL in the Presence of the Substituted Citrate A2 and of Citrate For a final volume of 100 mL of composition, with a mass ratio [substituted citrate A2]/[insulin lispro] of 2.0 and a concentration of 9.3 mM of citrate, the different reagents are added in the quantities specified below and in the following order:

| | |
|---|---|
| Lyophilized compound (substituted citrate A2) | 730 mg |
| Commercial solution of Humalog ® | 100 mL |
| Solution of sodium citrate at 1.188M | 783 µL |

The final pH is adjusted to 7.4±0.4.
The clear solution is filtered through a 0.22 µm membrane and stored at 4° C.

B40. Preparation of a Solution of Human Insulin at 100 IU/mL in the Presence of the Substituted Citrate A2 and of Citrate For a final volume of 100 mL of composition, with a mass ratio [substituted citrate A2]/[human insulin] of 2.0 and a concentration of 9.3 mM of citrate, the different reagents are added in the quantities specified below and in the following order:

| | |
|---|---|
| Lyophilized compound (substituted citrate A2) | 730 mg |
| Commercial solution of Humulin ® R | 100 mL |
| Solution of sodium citrate at 1.188M | 783 µL |

The final pH is adjusted to 7.4±0.4.
The clear solution is filtered through a 0.22 µm membrane and stored at 4° C.

B41. Preparation of a Solution of Insulin Aspart at 100 IU/mL in the Presence of the Substituted Citrate A2 and of Citrate For a final volume of 100 mL of composition, with a mass ratio [substituted citrate A2]/[insulin aspart] of 2.0 and a concentration of 9.3 mM of citrate, the different reagents are added in the quantities specified below and in the following order:

| | |
|---|---|
| Lyophilized compound (substituted citrate A2) | 730 mg |
| Commercial solution of Novolog ® | 100 mL |
| Solution of sodium citrate at 1.188M | 783 µL |

The final pH is adjusted to 7.4±0.4.
The clear solution is filtered through a 0.22 µm membrane and stored at 4° C.

B42. Preparation of a Solution of Insulin Lispro at 200 IU/mL in the Presence of the Substituted Citrate A2 and of Citrate.

For a final volume of 100 mL of formulation with a mass ratio [substituted citrate A2]/[insulin lispro] of 2.0 and a concentration of 18.6 mM of citrate, the different reagents are added in the quantities specified below and in the following order:

| | |
|---|---|
| Lyophilized compound (substituted citrate A2) | 1460 mg |
| Insulin lispro at 200 IU/mL | 100 mL |
| Solution of sodium citrate at 1.188M | 1566 µL |

The final pH is adjusted to 7.4±0.4. The clear solution is filtered through a 0.22 µm membrane and stored at 4° C.

B43. Preparation of a Solution of Human Insulin at 200 IU/mL in the Presence of the Substituted Citrate A2 and of Citrate.

For a final volume of 100 mL of formulation with a mass ratio [substituted citrate A2]/[human insulin] of 2.0 and a concentration of 18.6 mM of citrate, the different reagents are added in quantities specified below and in the following order:

| | |
|---|---|
| Lyophilized compound (substituted citrate A2) | 1460 mg |
| Human insulin at 200 IU/mL | 100 mL |
| Solution of sodium citrate at 1.188M | 1566 µL |

The final pH is adjusted to 7.4±0.4. The clear solution is filtered through a 0.22 µm membrane and stored at 4° C.

B44. Preparation of a Solution of Insulin Aspart at 200 IU/mL in the Presence of the Substituted Citrate A2 and of Citrate.

For a final volume of 100 mL of formulation with a mass ratio [substituted citrate A2]/[insulin aspart] of 2.0 and a concentration of 18.6 mM of citrate, the different reagents are added in quantities specified below and in the following order:

| | |
|---|---|
| Lyophilized compound (substituted citrate A2) | 1460 mg |
| Insulin aspart at 200 IU/mL | 100 mL |
| Solution of sodium citrate at 1.188M | 1566 µL |

The final pH is adjusted to 7.4±0.4. The clear solution is filtered through a 0.22 µm membrane and stored at 4° C.

B45. Preparation of a Solution of Insulin Lispro at 300 IU/mL in the Presence of the Substituted Citrate A2 and of Citrate.

For a final volume of 100 mL of formulation with a mass ratio [substituted citrate A2]/[insulin lispro] of 2.0 and a concentration of 27.9 mM of citrate, the different reagents are added in quantities specified below and in the following order:

| | |
|---|---|
| Lyophilized compound (substituted citrate A2) | 2190 mg |
| Insulin lispro at 300 IU/mL | 100 mL |
| Sodium citrate | 720 mg |

The final pH is adjusted to 7.4±0.4. The clear solution is filtered through a 0.22 µm membrane and stored at 4° C.

B46. Preparation of a Solution of Human Insulin at 300 IU/mL in the Presence of the Substituted Citrate A2 and of Citrate.

For a final volume of 100 mL of formulation with a mass ratio [substituted citrate A2]/[human insulin] of 2.0 and a concentration of 27.9 mM of citrate, the different reagents are added in quantities specified below and in the following order:

| | |
|---|---|
| Lyophilized compound (substituted citrate A2) | 2190 mg |
| Human insulin at 300 IU/mL | 100 mL |
| Sodium citrate | 720 mg |

The final pH is adjusted to 7.4±0.4. The clear solution is filtered through a 0.22 µm membrane and stored at 4° C.

B47. Preparation of a Solution of Insulin Lispro at 400 IU/mL in the Presence of the Substituted Citrate A2 and of Citrate.

For a final volume of 100 mL of formulation with a mass ratio [substituted citrate A2]/[insulin lispro] of 2.0 and a concentration of 37.2 mM of citrate, the different reagents are added in quantities specified below and in the following order:

| | |
|---|---|
| Lyophilized compound (substituted citrate A2) | 2920 mg |
| Insulin lispro at 400 IU/mL | 100 mL |
| Sodium citrate | 960 mg |

The final pH is adjusted to 7.4±0.4. The clear solution is filtered through a 0.22 μm membrane and stored at 4° C.

B48. Preparation of a Solution of Insulin Lispro at 500 IU/mL in the Presence of the Substituted Citrate A2 and of Citrate.

For a final volume of 100 mL of formulation with a mass ratio [substituted citrate A2]/[insulin lispro] of 2.0 and a concentration of 46.5 mM of citrate, the different reagents are added in quantities specified below and in the following order:

| | |
|---|---|
| Lyophilized compound (substituted citrate A2) | 3650 mg |
| Insulin lispro at 500 IU/mL | 100 mL |
| Sodium citrate | 1200 mg |

The final pH is adjusted to 7.4±0.4. The clear solution is filtered through a 0.22 μm membrane and stored at 4° C.

B49. Preparation of a Solution of Human Insulin at 500 IU/mL in the Presence of the Substituted Citrate A2 and of Citrate.

For a final volume of 100 mL of formulation with a mass ratio [substituted citrate A2]/[human insulin] of 2.0 and a concentration of 46.5 mM of citrate, the different reagents are added in quantities specified below and in the following order:

| | |
|---|---|
| Lyophilized compound (substituted citrate A2) | 3650 mg |
| Human insulin at 500 IU/mL | 100 mL |
| Sodium citrate | 1200 mg |

The final pH is adjusted to 7.4±0.4. The clear solution is filtered through a 0.22 μm membrane and stored at 4° C.

B50. Preparation of a Solution of Insulin Aspart at 500 IU/mL in the Presence of the Substituted Citrate A2 and of Citrate.

For a final volume of 100 mL of formulation with a mass ratio [substituted citrate A2]/[insulin aspart] of 2.0 and a concentration of 46.5 mM of citrate, the different reagents are added in quantities specified below and in the following order:

| | |
|---|---|
| Lyophilized compound (substituted citrate A2) | 3650 mg |
| Insulin aspart at 500 IU/mL | 100 mL |
| Sodium citrate | 1200 mg |

The final pH is adjusted to 7.4±0.4. The clear solution is filtered through a 0.22 μm membrane and stored at 4° C.

B51. Preparation of a Solution of Insulin Lispro at 100 IU/mL in the Presence of the Substituted Citrate A3 and of Citrate For a final volume of 100 mL of composition, with a mass ratio [substituted citrate A3]/[insulin lispro] of 2.0 and a concentration of 9.3 mM of citrate, the different reagents are added in the quantities specified below and in the following order:

| | |
|---|---|
| Lyophilized compound (substituted citrate A3) | 730 mg |
| Commercial solution of Humalog® | 100 mL |
| Solution of sodium citrate at 1.188M | 783 μL |

The final pH is adjusted to 7.4±0.4.
The clear solution is filtered through a 0.22 μm membrane and stored at 4° C.

B52. Preparation of a Solution of Human Insulin at 100 IU/mL in the Presence of the Substituted Citrate A3 and of Citrate For a final volume of 100 mL of composition, with a mass ratio [substituted citrate A3]/[human insulin] of 2.0 and a concentration of 9.3 mM of citrate, the different reagents are added in the quantities specified below and in the following order:

| | |
|---|---|
| Lyophilized compound (substituted citrate A3) | 730 mg |
| Commercial solution of Humulin® R | 100 mL |
| Solution of sodium citrate at 1.188M | 783 μL |

The final pH is adjusted to 7.4±0.4.
The clear solution is filtered through a 0.22 μm membrane and stored at 4° C.

B53. Preparation of a Solution of Insulin Aspart at 100 IU/mL in the Presence of the Substituted Citrate A3 and of Citrate For a final volume of 100 mL of composition, with a mass ratio [substituted citrate A3]/[insulin aspart] of 2.0 and a concentration of 9.3 mM of citrate, the different reagents are added in the quantities specified below and in the following order:

| | |
|---|---|
| Lyophilized compound (substituted citrate A3) | 730 mg |
| Commercial solution of Novolog® | 100 mL |
| Solution of sodium citrate at 1.188M | 783 μL |

The final pH is adjusted to 7.4±0.4.
The clear solution is filtered through a 0.22 μm membrane and stored at 4° C.

B54. Preparation of a Solution of Insulin Lispro at 200 IU/mL in the Presence of the Substituted Citrate A3 and of Citrate.

For a final volume of 100 mL of formulation with a mass ratio [substituted citrate A3]/[insulin lispro] of 2.0 and a concentration of 18.6 mM of citrate, the different reagents are added in the quantities specified below and in the following order:

| | |
|---|---|
| Lyophilized compound (substituted citrate A3) | 1460 mg |
| Insulin lispro at 200 IU/mL | 100 mL |
| Solution of sodium citrate at 1.188M | 1566 μL |

The final pH is adjusted to 7.4±0.4. The clear solution is filtered through a 0.22 μm membrane and stored at 4° C.

B55. Preparation of a Solution of Human Insulin at 200 IU/mL in the Presence of the Substituted Citrate A3 and of Citrate.

For a final volume of 100 mL of formulation with a mass ratio [substituted citrate A3]/[human insulin] of 2.0 and a concentration of 18.6 mM of citrate, the different reagents are added in quantities specified below and in the following order:

| | |
|---|---|
| Lyophilized compound (substituted citrate A3) | 1460 mg |
| Human insulin at 200 IU/mL | 100 mL |
| Solution of sodium citrate at 1.188M | 1566 µL |

The final pH is adjusted to 7.4±0.4. The clear solution is filtered through a 0.22 µm membrane and stored at 4° C.

B56. Preparation of a Solution of Insulin Aspart at 200 IU/mL in the Presence of the Substituted Citrate A3 and of Citrate.

For a final volume of 100 mL of formulation with a mass ratio [substituted citrate A3]/[insulin aspart] of 2.0 and a concentration of 18.6 mM of citrate, the different reagents are added in quantities specified below and in the following order:

| | |
|---|---|
| Lyophilized compound (substituted citrate A3) | 1460 mg |
| Insulin aspart at 200 IU/mL | 100 mL |
| Solution of sodium citrate at 1.188M | 1566 µL |

The final pH is adjusted to 7.4±0.4. The clear solution is filtered through a 0.22 µm membrane and stored at 4° C.

B57. Preparation of a Solution of Insulin Lispro at 300 IU/mL in the Presence of the Substituted Citrate A3 and of Citrate.

For a final volume of 100 mL of formulation, the different reagents are added in quantities specified below and in the following order:

| | |
|---|---|
| Lyophilized compound (substituted citrate A3) | 1460 mg |
| Insulin lispro at 300 IU/mL | 100 mL |
| Sodium citrate | 720 mg |

The final pH is adjusted to 7.4±0.4. The clear solution is filtered through a 0.22 µm membrane and stored at 4° C.

B58. Preparation of a Solution of Insulin Lispro at 400 IU/mL in the Presence of the Substituted Citrate A3 and of Citrate.

For a final volume of 100 mL of formulation, the different reagents are added in quantities specified below and in the following order:

| | |
|---|---|
| Lyophilized compound (substituted citrate A3) | 1460 mg |
| Insulin lispro at 400 IU/mL | 100 mL |
| Sodium citrate | 960 mg |

The final pH is adjusted to 7.4±0.4. The clear solution is filtered through a 0.22 µm membrane and stored at 4° C.

B59. Preparation of a Solution of Insulin Lispro at 500 IU/mL in the Presence of the Substituted Citrate A3 and of Citrate.

For a final volume of 100 mL of formulation, the different reagents are added in quantities specified below and in the following order:

| | |
|---|---|
| Lyophilized compound (substituted citrate A3) | 1460 mg |
| Insulin lispro at 500 IU/mL | 100 mL |
| Sodium citrate | 1200 mg |

The final pH is adjusted to 7.4±0.4. The clear solution is filtered through a 0.22 µm membrane and stored at 4° C.

B60. Preparation of a Solution of Human Insulin at 500 IU/mL in the Presence of the Substituted Citrate A3 and of Citrate.

For a final volume of 100 mL of formulation, the different reagents are added in quantities specified below and in the following order:

| | |
|---|---|
| Lyophilized compound (substituted citrate A3) | 1460 mg |
| Human insulin at 500 IU/mL | 100 mL |
| Sodium citrate | 1200 mg |

The final pH is adjusted to 7.4±0.4. The clear solution is filtered through a 0.22 µm membrane and stored at 4° C.

B61. Preparation of a Solution of Insulin Aspart at 500 IU/mL in the Presence of the Substituted Citrate A3 and of Citrate.

For a final volume of 100 mL of formulation, the different reagents are added in quantities specified below and in the following order:

| | |
|---|---|
| Lyophilized compound (substituted citrate A3) | 1460 mg |
| Insulin aspart at 500 IU/mL | 100 mL |
| Sodium citrate | 1200 mg |

The final pH is adjusted to 7.4±0.4. The clear solution is filtered through a 0.22 µm membrane and stored at 4° C.

B62. Preparation of a Solution of Insulin Lispro at 100 IU/mL in the Presence of the Substituted Citrate A3.

For a final volume of 100 mL of composition, with a mass ratio [substituted citrate A3]/[insulin lispro] of 2.0, the different reagents are added in the quantities specified below and in the following order:

| | |
|---|---|
| Lyophilized compound (substituted citrate A3) | 730 mg |
| Commercial solution of Humalog ® | 100 mL |

The final pH is adjusted to 7.4±0.4. The clear solution is filtered through a 0.22 µm membrane and stored at 4° C.

B63. Preparation of a Solution of Human Solution at 100 IU/mL in the Presence of the Substituted Citrate A3.

For a final volume of 100 mL of composition, with a mass ratio [substituted citrate A3]/[human insulin] of 2.0, the different reagents are added in the quantities specified below and in the following order:

| | |
|---|---|
| Lyophilized compound (substituted citrate A3) | 730 mg |
| Commercial solution of Humulin ® R | 100 mL |

The final pH is adjusted to 7.4±0.4. The clear solution is filtered through a 0.22 µm membrane and stored at 4° C.

B64. Preparation of a Solution of Insulin Lispro at 200 IU/mL in the Presence of the Substituted Citrate A3, For a final volume of 100 mL of formulation with a mass ratio [substituted citrate A3]/[insulin lispro] of 2.0, the different reagents are added in the quantities specified below and in the following order:

| Lyophilized compound (substituted citrate A3) | 1460 mg |
| Insulin lispro at 200 IU/mL | 100 mL |

The final pH is adjusted to 7.4±0.4. The clear solution is filtered through a 0.22 μm membrane and stored at 4° C.

B65. Preparation of a Solution of Human Insulin at 200 IU/mL in the Presence of the Substituted Citrate A3.

For a final volume of 100 mL of formulation with a mass ratio [substituted citrate A3]/[human insulin] of 2.0, the different reagents are added in quantities specified below and in the following order:

| Lyophilized compound (substituted citrate A3) | 1460 mg |
| Human insulin at 200 IU/mL | 100 mL |

The final pH is adjusted to 7.4±0.4. The clear solution is filtered through a 0.22 μm membrane and stored at 4° C.

B66. Preparation of a Solution of Insulin Lispro at 300 IU/mL in the Presence of the Substituted Citrate A3.

For a final volume of 100 mL of formulation, the different reagents are added in quantities specified below and in the following order:

| Lyophilized compound (substituted citrate A3) | 1460 mg |
| Insulin lispro at 300 IU/mL | 100 mL |

The final pH is adjusted to 7.4±0.4. The clear solution is filtered through a 0.22 μm membrane and stored at 4° C.

B67. Preparation of a Solution of Human Insulin at 300 IU/mL in the Presence of the Substituted Citrate A3.

For a final volume of 100 mL of formulation, the different reagents are added in quantities specified below and in the following order:

| Lyophilized compound (substituted citrate A3) | 1460 mg |
| Human insulin at 300 IU/mL | 100 mL |

The final pH is adjusted to 7.4±0.4. The clear solution is filtered through a 0.22 μm membrane and stored at 4° C.

B68. Preparation of a Solution of Insulin Lispro at 400 IU/mL in the Presence of the Substituted Citrate A3.

For a final volume of 100 mL of formulation, the different reagents are added in quantities specified below and in the following order:

| Lyophilized compound (substituted citrate A3) | 1460 mg |
| Insulin lispro at 400 IU/mL | 100 mL |

The final pH is adjusted to 7.4±0.4. The clear solution is filtered through a 0.22 μm membrane and stored at 4° C.

B69. Preparation of a Solution of Human Insulin at 400 IU/mL in the Presence of the Substituted Citrate A3.

For a final volume of 100 mL of formulation, the different reagents are added in quantities specified below and in the following order:

| Lyophilized compound (substituted citrate A3) | 1460 mg |
| Human insulin at 400 IU/mL | 100 mL |

The final pH is adjusted to 7.4±0.4. The clear solution is filtered through a 0.22 μm membrane and stored at 4° C.

B70. Preparation of a Solution of Insulin Lispro at 500 IU/mL in the Presence of the Substituted Citrate A3.

For a final volume of 100 mL of formulation, the different reagents are added in quantities specified below and in the following order:

| Lyophilized compound (substituted citrate A3) | 1460 mg |
| Insulin lispro at 500 IU/mL | 100 mL |

The final pH is adjusted to 7.4±0.4. The clear solution is filtered through a 0.22 μm membrane and stored at 4° C.

B71. Preparation of a Solution of Human Insulin at 500 IU/mL in the Presence of the Substituted Citrate A3.

For a final volume of 100 mL of formulation, the different reagents are added in quantities specified below and in the following order:

| Lyophilized compound (substituted citrate A3) | 1460 mg |
| Human insulin at 500 IU/mL | 100 mL |

The final pH is adjusted to 7.4±0.4. The clear solution is filtered through a 0.22 μm membrane and stored at 4° C.

B72. Preparation of a Solution of Insulin Lispro at 100 IU/mL in the Presence of the Substituted Citrate A3.

For a final volume of 100 mL of composition, with a mass ratio [substituted citrate A3]/[insulin lispro] of 4.0, the different reagents are added in the quantities specified below and in the following order:

| Lyophilized compound (substituted citrate A3) | 1460 mg |
| Commercial solution of Humalog ® | 100 mL |

The final pH is adjusted to 7.4±0.4.

The clear solution is filtered through a 0.22 μm membrane and stored at 4° C.

B73. Preparation of a Solution of Human Insulin at 100 IU/mL in the Presence of the Substituted Citrate A3.

For a final volume of 100 mL of composition, with a mass ratio [substituted citrate A3]/[human insulin] of 4.0, the different reagents are added in the quantities specified below and in the following order:

| Lyophilized compound (substituted citrate A3) | 1460 mg |
| Commercial solution of Humulin ® R | 100 mL |

The final pH is adjusted to 7.4±0.4.

The clear solution is filtered through a 0.22 μm membrane and stored at 4° C.

B74. Preparation of a Solution of Insulin Lispro at 200 IU/mL in the Presence of the Substituted Citrate A3.

For a final volume of 100 mL of formulation, the different reagents are added in the quantities specified below and in the following order:

| Lyophilized compound (substituted citrate A3) | 1460 mg |
| Insulin lispro at 200 IU/mL | 100 mL |

The final pH is adjusted to 7.4±0.4. The clear solution is filtered through a 0.22 μm membrane and stored at 4° C.

B75. Preparation of a Solution of Human Insulin at 200 IU/mL in the Presence of the Substituted Citrate A3.

For a final volume of 100 mL of formulation, the different reagents are added in quantities specified below and in the following order:

| Lyophilized compound (substituted citrate A3) | 1460 mg |
| Human insulin at 200 IU/mL | 100 mL |

The final pH is adjusted to 7.4±0.4. The clear solution is filtered through a 0.22 μm membrane and stored at 4° C.

B76. Preparation of a Solution of Insulin Lispro at 300 IU/mL in the Presence of the Substituted Citrate A3.

For a final volume of 100 mL of formulation, the different reagents are added in quantities specified below and in the following order:

| Lyophilized compound (substituted citrate A3) | 1460 mg |
| Insulin lispro at 300 IU/mL | 100 mL |

The final pH is adjusted to 7.4±0.4. The clear solution is filtered through a 0.22 μm membrane and stored at 4° C.

B77. Preparation of a Solution of Human Insulin at 300 IU/mL in the Presence of the Substituted Citrate A3.

For a final volume of 100 mL of formulation, the different reagents are added in quantities specified below and in the following order:

| Lyophilized compound (substituted citrate A3) | 1460 mg |
| Human insulin at 300 IU/mL | 100 mL |

The final pH is adjusted to 7.4±0.4. The clear solution is filtered through a 0.22 μm membrane and stored at 4° C.

B78. Preparation of a Solution of Insulin Lispro at 400 IU/mL in the Presence of the Substituted Citrate A3.

For a final volume of 100 mL of formulation, the different reagents are added in quantities specified below and in the following order:

| Lyophilized compound (substituted citrate A3) | 1460 mg |
| Insulin lispro at 400 IU/mL | 100 mL |

The final pH is adjusted to 7.4±0.4. The clear solution is filtered through a 0.22 μm membrane and stored at 4° C.

B79. Preparation of a Solution of Human Insulin at 400 IU/mL in the Presence of the Substituted Citrate A3.

For a final volume of 100 mL of formulation, the different reagents are added in quantities specified below and in the following order:

| Lyophilized compound (substituted citrate A3) | 1460 mg |
| Human insulin at 400 IU/mL | 100 mL |

The final pH is adjusted to 7.4±0.4. The clear solution is filtered through a 0.22 μm membrane and stored at 4° C.

B80. Preparation of a Solution of Insulin Lispro at 500 IU/mL in the Presence of the Substituted Citrate A3.

For a final volume of 100 mL of formulation, the different reagents are added in quantities specified below and in the following order:

| Lyophilized compound (substituted citrate A3) | 1460 mg |
| Insulin lispro at 500 IU/mL | 100 mL |

The final pH is adjusted to 7.4±0.4. The clear solution is filtered through a 0.22 μm membrane and stored at 4° C.

B81. Preparation of a Solution of Human Insulin at 500 IU/mL in the Presence of the Substituted Citrate A3.

For a final volume of 100 mL of formulation, the different reagents are added in quantities specified below and in the following order:

| Lyophilized compound (substituted citrate A3) | 1460 mg |
| Human insulin at 500 IU/mL | 100 mL |

The final pH is adjusted to 7.4±0.4. The clear solution is filtered through a 0.22 μm membrane and stored at 4° C.

B82. Preparation of a Solution of Insulin Aspart at 100 IU/mL in the Presence of the Substituted Citrate A3

For a final volume of 100 mL of composition, with a mass ratio [substituted citrate A3]/[insulin aspart] of 2.0, the different reagents are added in the quantities specified below and in the following order:

| Lyophilized compound (substituted citrate A3) | 730 mg |
| Commercial solution of Novolog® | 100 mL |

The final pH is adjusted to 7.4±0.4.

The clear solution is filtered through a 0.22 μm membrane and stored at 4° C.

B83. Preparation of a Solution of Insulin Aspart at 100 IU/mL in the Presence of the Substituted Citrate A3

For a final volume of 100 mL of composition, with a mass ratio [substituted citrate A3]/[insulin aspart] of 4.0, the different reagents are added in the quantities specified below and in the following order:

| Lyophilized compound (substituted citrate A3) | 1460 mg |
| Commercial solution of Novolog® | 100 mL |

The final pH is adjusted to 7.4±0.4.

The clear solution is filtered through a 0.22 μm membrane and stored at 4° C.

B84. Preparation of a Solution of Insulin Glulisine at 100 IU/mL in the Presence of the Substituted Citrate A3 and of Citrate For a final volume of 100 mL of composition, with a mass ratio [substituted citrate A3]/[insulin glulisine] of 2.0 and a concentration of 9.3 mM of citrate, the different reagents are added in the quantities specified below and in the following order:

| Lyophilized compound (substituted citrate A3) | 730 mg |
| Commercial solution of Apidra® | 100 mL |
| Solution of sodium citrate at 1.188M | 783 μL |

The final pH is adjusted to 7.4±0.4.

The clear solution is filtered through a 0.22 μm membrane and stored at 4° C.

B85. Preparation of a Solution of Insulin Glulisine at 100 IU/mL in the Presence of the Substituted Citrate A3

For a final volume of 100 mL of composition, with a mass ratio [substituted citrate A3]/[insulin glulisine] of 2.0, the different reagents are added in the quantities specified below and in the following order:

| Lyophilized compound (substituted citrate A3) | 730 mg |
| Commercial solution of Apidra ® | 100 mL |

The final pH is adjusted to 7.4±0.4.

The clear solution is filtered through a 0.22 μm membrane and stored at 4° C.

B86. Preparation of a Solution of Insulin Glulisine at 100 IU/mL in the Presence of the Substituted Citrate A3

For a final volume of 100 mL of composition, with a mass ratio [substituted citrate A3]/[insulin glulisine] of 4.0, the different reagents are added in the quantities specified below and in the following order:

| Lyophilized compound (substituted citrate A3) | 1460 mg |
| Commercial solution of Apidra ® | 100 mL |

The final pH is adjusted to 7.4±0.4.

The clear solution is filtered through a 0.22 μm membrane and stored at 4° C.

B87. Preparation of a Solution of Insulin Lispro at 100 IU/mL in the Presence of the Substituted Citrate A4 and of Citrate For a final volume of 100 mL of composition, with a mass ratio [substituted citrate A4]/[insulin lispro] of 2.0 and a concentration of 9.3 mM of citrate, the different reagents are added in the quantities specified below and in the following order:

| Lyophilized compound (substituted citrate A4) | 730 mg |
| Commercial solution of Humalog ® | 100 mL |
| Solution of sodium citrate at 1.188M | 783 μL |

The final pH is adjusted to 7.4±0.4.

The clear solution is filtered through a 0.22 μm membrane and stored at 4° C.

B88. Preparation of a Solution of Human Insulin at 100 IU/mL in the Presence of the Substituted Citrate A4 and of Citrate For a final volume of 100 mL of composition, with a mass ratio [substituted citrate A4]/[human insulin] of 2.0 and a concentration of 9.3 mM of citrate, the different reagents are added in the quantities specified below and in the following order:

| Lyophilized compound (substituted citrate A4) | 730 mg |
| Commercial solution of Humulin ® R | 100 mL |
| Solution of sodium citrate at 1.188M | 783 μL |

The final pH is adjusted to 7.4±0.4.

The clear solution is filtered through a 0.22 μm membrane and stored at 4° C.

B89. Preparation of a Solution of Insulin Aspart at 100 IU/mL in the Presence of the Substituted Citrate A4 and of Citrate For a final volume of 100 mL of composition, with a mass ratio [substituted citrate A4]/[insulin aspart] of 2.0 and a concentration of 9.3 mM of citrate, the different reagents are added in the quantities specified below and in the following order:

| Lyophilized compound (substituted citrate A4) | 730 mg |
| Commercial solution of Novolog ® | 100 mL |
| Solution of sodium citrate at 1.188M | 783 μL |

The final pH is adjusted to 7.4±0.4.

The clear solution is filtered through a 0.22 μm membrane and stored at 4° C.

B90. Preparation of a Solution of Insulin Lispro at 200 IU/mL in the Presence of the Substituted Citrate A4 and of Citrate.

For a final volume of 100 mL of formulation with a mass ratio [substituted citrate A4]/[insulin lispro] of 2.0 and a concentration of 18.6 mM of citrate, the different reagents are added in the quantities specified below and in the following order:

| Lyophilized compound (substituted citrate A4) | 1460 mg |
| Insulin lispro at 200 IU/mL | 100 mL |
| Solution of sodium citrate at 1.188M | 1566 μL |

The final pH is adjusted to 7.4±0.4. The clear solution is filtered through a 0.22 μm membrane and stored at 4° C.

B91. Preparation of a Solution of Human Insulin at 200 IU/mL in the Presence of the Substituted Citrate A4 and of Citrate.

For a final volume of 100 mL of formulation, with a mass ratio [substituted citrate A4]/[human insulin] of 2.0 and a concentration of 18.6 mM of citrate, the different reagents are added in quantities specified below and in the following order:

| Lyophilized compound (substituted citrate A4) | 1460 mg |
| Human insulin at 200 IU/mL | 100 mL |
| Solution of sodium citrate at 1.188M | 1566 μL |

The final pH is adjusted to 7.4±0.4. The clear solution is filtered through a 0.22 μm membrane and stored at 4° C.

B92. Preparation of a Solution of Insulin Aspart at 200 IU/mL in the Presence of the Substituted Citrate A4 and of Citrate.

For a final volume of 100 mL of formulation with a mass ratio [substituted citrate A4]/[insulin aspart] of 2.0 and a concentration of 18.6 mM of citrate, the different reagents are added in quantities specified below and in the following order:

| Lyophilized compound (substituted citrate A4) | 1460 mg |
| Insulin aspart at 200 IU/mL | 100 mL |
| Solution of sodium citrate at 1.188M | 1566 μL |

The final pH is adjusted to 7.4±0.4. The clear solution is filtered through a 0.22 μm membrane and stored at 4° C.

B93. Preparation of a Solution of Insulin Lispro at 300 IU/mL in the Presence of the Substituted Citrate A4 and of Citrate.

For a final volume of 100 mL of formulation, the different reagents are added in quantities specified below and in the following order:

| | |
|---|---|
| Lyophilized compound (substituted citrate A4) | 1460 mg |
| Insulin lispro at 300 IU/mL | 100 mL |
| Sodium citrate | 720 mg |

The final pH is adjusted to 7.4±0.4. The clear solution is filtered through a 0.22 μm membrane and stored at 4° C.

B94. Preparation of a Solution of Insulin Lispro at 400 IU/mL in the Presence of the Substituted Citrate A4 and of Citrate.

For a final volume of 100 mL of formulation, the different reagents are added in quantities specified below and in the following order:

| | |
|---|---|
| Lyophilized compound (substituted citrate A4) | 1460 mg |
| Insulin lispro at 400 IU/mL | 100 mL |
| Sodium citrate | 960 mg |

The final pH is adjusted to 7.4±0.4. The clear solution is filtered through a 0.22 μm membrane and stored at 4° C.

B95. Preparation of a Solution of Insulin Lispro at 500 IU/mL in the Presence of the Substituted Citrate A4 and of Citrate.

For a final volume of 100 mL of formulation, the different reagents are added in quantities specified below and in the following order:

| | |
|---|---|
| Lyophilized compound (substituted citrate A4) | 1460 mg |
| Insulin lispro at 500 IU/mL | 100 mL |
| Sodium citrate | 1200 mg |

The final pH is adjusted to 7.4±0.4. The clear solution is filtered through a 0.22 μm membrane and stored at 4° C.

B96. Preparation of a Solution of Human Insulin at 500 IU/mL in the Presence of the Substituted Citrate A4 and of Citrate.

For a final volume of 100 mL of formulation, the different reagents are added in quantities specified below and in the following order:

| | |
|---|---|
| Lyophilized compound (substituted citrate A4) | 1460 mg |
| Human insulin at 500 IU/mL | 100 mL |
| Sodium citrate | 1200 mg |

The final pH is adjusted to 7.4±0.4. The clear solution is filtered through a 0.22 μm membrane and stored at 4° C.

B97. Preparation of a Solution of Insulin Aspart at 500 IU/mL in the Presence of the Substituted Citrate A4 and of Citrate.

For a final volume of 100 mL of formulation, the different reagents are added in quantities specified below and in the following order:

| | |
|---|---|
| Lyophilized compound (substituted citrate A4) | 1460 mg |
| Insulin aspart at 500 IU/mL | 100 mL |
| Sodium citrate | 1200 mg |

The final pH is adjusted to 7.4±0.4. The clear solution is filtered through a 0.22 μm membrane and stored at 4° C.

B98. Preparation of a Solution of Insulin Lispro at 100 IU/mL in the Presence of the Substituted Citrate A4.

For a final volume of 100 mL of composition, with a mass ratio [substituted citrate A4]/[insulin lispro] of 2.0, the different reagents are added in the quantities specified below and in the following order:

| | |
|---|---|
| Lyophilized compound (substituted citrate A4) | 730 mg |
| Commercial solution of Humalog ® | 100 mL |

The final pH is adjusted to 7.4±0.4. The clear solution is filtered through a 0.22 μm membrane and stored at 4° C.

B99. Preparation of a Solution of Human Insulin at 100 IU/mL in the Presence of the Substituted Citrate A4.

For a final volume of 100 mL of composition, with a mass ratio [substituted citrate A4]/[human insulin] of 2.0, the different reagents are added in the quantities specified below and in the following order:

| | |
|---|---|
| Lyophilized compound (substituted citrate A4) | 730 mg |
| Commercial solution of Humulin ® R | 100 mL |

The final pH is adjusted to 7.4±0.4. The clear solution is filtered through a 0.22 μm membrane and stored at 4° C.

B100. Preparation of a Solution of Insulin Lispro at 200 IU/mL in the Presence of the Substituted Citrate A4.

For a final volume of 100 mL of formulation, with a mass ratio [substituted citrate A4]/[insulin lispro] of 2.0, the different reagents are added in the quantities specified below and in the following order:

| | |
|---|---|
| Lyophilized compound (substituted citrate A4) | 1460 mg |
| Insulin lispro at 200 IU/mL | 100 mL |

The final pH is adjusted to 7.4±0.4. The clear solution is filtered through a 0.22 μm membrane and stored at 4° C.

B101. Preparation of a Solution of Human Insulin at 200 IU/mL in the Presence of the Substituted Citrate A4.

For a final volume of 100 mL of formulation, with a mass ratio [substituted citrate A4]/[human insulin] of 2.0, the different reagents are added in quantities specified below and in the following order:

| | |
|---|---|
| Lyophilized compound (substituted citrate A4) | 1460 mg |
| Human insulin at 200 IU/mL | 100 mL |

The final pH is adjusted to 7.4±0.4. The clear solution is filtered through a 0.22 μm membrane and stored at 4° C.

B102. Preparation of a Solution of Insulin Lispro at 300 IU/mL in the Presence of the Substituted Citrate A4.

For a final volume of 100 mL of formulation, the different reagents are added in quantities specified below and in the following order:

| | |
|---|---|
| Lyophilized compound (substituted citrate A4) | 1460 mg |
| Insulin lispro at 300 IU/mL | 100 mL |

The final pH is adjusted to 7.4±0.4. The clear solution is filtered through a 0.22 μm membrane and stored at 4° C.

B103. Preparation of a Solution of Human Insulin at 300 IU/mL in the Presence of the Substituted Citrate A4.

For a final volume of 100 mL of formulation, the different reagents are added in quantities specified below and in the following order:

| Lyophilized compound (substituted citrate A4) | 1460 mg |
| Human insulin at 300 IU/mL | 100 mL |

The final pH is adjusted to 7.4±0.4. The clear solution is filtered through a 0.22 μm membrane and stored at 4° C.

B104. Preparation of a Solution of Insulin Lispro at 400 IU/mL in the Presence of the Substituted Citrate A4.

For a final volume of 100 mL of formulation, the different reagents are added in quantities specified below and in the following order:

| Lyophilized compound (substituted citrate A4) | 1460 mg |
| Insulin lispro at 400 IU/mL | 100 mL |

The final pH is adjusted to 7.4±0.4. The clear solution is filtered through a 0.22 μm membrane and stored at 4° C.

B105. Preparation of a Solution of Human Insulin at 400 IU/mL in the Presence of the Substituted Citrate A4.

For a final volume of 100 mL of formulation, the different reagents are added in quantities specified below and in the following order:

| Lyophilized compound (substituted citrate A4) | 1460 mg |
| Human insulin at 400 IU/mL | 100 mL |

The final pH is adjusted to 7.4±0.4. The clear solution is filtered through a 0.22 μm membrane and stored at 4° C.

B106. Preparation of a Solution of Insulin Lispro at 500 IU/mL in the Presence of the Substituted Citrate A4.

For a final volume of 100 mL of formulation, the different reagents are added in quantities specified below and in the following order:

| Lyophilized compound (substituted citrate A4) | 1460 mg |
| Insulin lispro at 500 IU/mL | 100 mL |

The final pH is adjusted to 7.4±0.4. The clear solution is filtered through a 0.22 μm membrane and stored at 4° C.

B107. Preparation of a Solution of Human Insulin at 500 IU/mL in the Presence of the Substituted Citrate A4.

For a final volume of 100 mL of formulation, the different reagents are added in quantities specified below and in the following order:

| Lyophilized compound (substituted citrate A4) | 1460 mg |
| Human insulin at 500 IU/mL | 100 mL |

The final pH is adjusted to 7.4±0.4. The clear solution is filtered through a 0.22 μm membrane and stored at 4° C.

B108. Preparation of a Solution of Insulin Lispro at 100 IU/mL in the Presence of the Substituted Citrate A4.

For a final volume of 100 mL of composition, with a mass ratio [substituted citrate A4]/[insulin lispro] of 4.0, the different reagents are added in the quantities specified below and in the following order:

| Lyophilized compound (substituted citrate A4) | 1460 mg |
| Commercial solution of Humalog ® | 100 mL |

The final pH is adjusted to 7.4±0.4.
The clear solution is filtered through a 0.22 μm membrane and stored at 4° C.

B109. Preparation of a Solution of Human Insulin at 100 IU/mL in the Presence of the Substituted Citrate A4.

For a final volume of 100 mL of composition, with a mass ratio [substituted citrate A4]/[human insulin] of 4.0, the different reagents are added in the quantities specified below and in the following order:

| Lyophilized compound (substituted citrate A4) | 1460 mg |
| Commercial solution of Humulin ® | 100 mL |

The final pH is adjusted to 7.4±0.4.
The clear solution is filtered through a 0.22 μm membrane and stored at 4° C.

B110. Preparation of a Solution of Insulin Lispro at 200 IU/mL in the Presence of the Substituted Citrate A4.

For a final volume of 100 mL of formulation, the different reagents are added in the quantities specified below and in the following order:

| Lyophilized compound (substituted citrate A4) | 1460 mg |
| Insulin lispro at 200 IU/mL | 100 mL |

The final pH is adjusted to 7.4±0.4. The clear solution is filtered through a 0.22 μm membrane and stored at 4° C.

B111. Preparation of a Solution of Human Insulin at 200 IU/mL in the Presence of the Substituted Citrate A4.

For a final volume of 100 mL of formulation, the different reagents are added in quantities specified below and in the following order:

| Lyophilized compound (substituted citrate A4) | 1460 mg |
| Human insulin at 200 IU/mL | 100 mL |

The final pH is adjusted to 7.4±0.4. The clear solution is filtered through a 0.22 μm membrane and stored at 4° C.

B112. Preparation of a Solution of Insulin Lispro at 300 IU/mL in the Presence of the Substituted Citrate A4.

For a final volume of 100 mL of formulation, the different reagents are added in the quantities specified below and in the following order:

| Lyophilized compound (substituted citrate A4) | 1460 mg |
| Insulin lispro at 300 IU/mL | 100 mL |

The final pH is adjusted to 7.4±0.4. The clear solution is filtered through a 0.22 μm membrane and stored at 4° C.

B113. Preparation of a Solution of Human Insulin at 300 IU/mL in the Presence of the Substituted Citrate A4.

For a final volume of 100 mL of formulation, the different reagents are added in quantities specified below and in the following order:

| Lyophilized compound (substituted citrate A4) | 1460 mg |
| Human insulin at 300 IU/mL | 100 mL |

The final pH is adjusted to 7.4±0.4. The clear solution is filtered through a 0.22 μm membrane and stored at 4° C.

B114. Preparation of a Solution of Insulin Lispro at 400 IU/mL in the Presence of the Substituted Citrate A4.

For a final volume of 100 mL of formulation, the different reagents are added in quantities specified below and in the following order:

| Lyophilized compound (substituted citrate A4) | 1460 mg |
| Insulin lispro at 400 IU/mL | 100 mL |

The final pH is adjusted to 7.4±0.4. The clear solution is filtered through a 0.22 μm membrane and stored at 4° C.

B115. Preparation of a Solution of Human Insulin at 400 IU/mL in the Presence of the Substituted Citrate A4.

For a final volume of 100 mL of formulation, the different reagents are added in quantities specified below and in the following order:

| Lyophilized compound (substituted citrate A4) | 1460 mg |
| Human insulin at 400 IU/mL | 100 mL |

The final pH is adjusted to 7.4±0.4. The clear solution is filtered through a 0.22 μm membrane and stored at 4° C.

B116. Preparation of a Solution of Insulin Lispro at 500 IU/mL in the Presence of the Substituted Citrate A4.

For a final volume of 100 mL of formulation, the different reagents are added in quantities specified below and in the following order:

| Lyophilized compound (substituted citrate A4) | 1460 mg |
| Insulin lispro at 500 IU/mL | 100 mL |

The final pH is adjusted to 7.4±0.4. The clear solution is filtered through a 0.22 μm membrane and stored at 4° C.

B117. Preparation of a Solution of Human Insulin at 500 IU/mL in the Presence of the Substituted Citrate A4.

For a final volume of 100 mL of formulation, the different reagents are added in quantities specified below and in the following order:

| Lyophilized compound (substituted citrate A4) | 1460 mg |
| Human insulin at 500 IU/mL | 100 mL |

The final pH is adjusted to 7.4±0.4. The clear solution is filtered through a 0.22 μm membrane and stored at 4° C.

B118. Preparation of a Solution of Insulin Aspart at 100 IU/mL in the Presence of the Substituted Citrate A4

For a final volume of 100 mL of composition, with a mass ratio [substituted citrate A4]/[insulin aspart] of 2.0, the different reagents are added in the quantities specified below and in the following order:

| Lyophilized compound (substituted citrate A4) | 730 mg |
| Commercial solution of Novolog ® | 100 mL |

The final pH is adjusted to 7.4±0.4.

The clear solution is filtered through a 0.22 μm membrane and stored at 4° C.

B119. Preparation of a Solution of Insulin Aspart at 100 IU/mL in the Presence of the Substituted Citrate A4

For a final volume of 100 mL of composition, with a mass ratio [substituted citrate A4]/[insulin aspart] of 4.0, the different reagents are added in the quantities specified below and in the following order:

| Lyophilized compound (substituted citrate A4) | 1460 mg |
| Commercial solution of Novolog ® | 100 mL |

The final pH is adjusted to 7.4±0.4.

The clear solution is filtered through a 0.22 μm membrane and stored at 4° C.

B120. Preparation of a Solution of Insulin Glulisine at 100 IU/mL in the Presence of the Substituted Citrate A4 and of Citrate For a final volume of 100 mL of composition, with a mass ratio [substituted citrate A4]/[insulin glulisine] of 2.0, and a concentration of 9.3 mM of citrate, the different reagents are added in the quantities specified below and in the following order:

| Lyophilized compound (substituted citrate A4) | 730 mg |
| Commercial solution of Apidra ® | 100 mL |
| Solution of sodium citrate at 1.188M | 783 μL |

The final pH is adjusted to 7.4±0.4.

The clear solution is filtered through a 0.22 μm membrane and stored at 4° C.

B121. Preparation of a Solution of Insulin Glulisine at 100 IU/mL in the Presence of the Substituted Citrate A4

For a final volume of 100 mL of composition, with a mass ratio [substituted citrate A4]/[insulin glulisine] of 2.0, the different reagents are added in the quantities specified below and in the following order:

| Lyophilized compound (substituted citrate A4) | 730 mg |
| Commercial solution of Apidra ® | 100 mL |

The final pH is adjusted to 7.4±0.4.

The clear solution is filtered through a 0.22 μm membrane and stored at 4° C.

B122. Preparation of a Solution of Insulin Glulisine at 100 IU/mL in the Presence of the Substituted Citrate A4

For a final volume of 100 mL of composition, with a mass ratio [substituted citrate A4]/[insulin glulisine] of 4.0, the different reagents are added in the quantities specified below and in the following order:

| Lyophilized compound (substituted citrate A4) | 1460 mg |
| Commercial solution of Apidra ® | 100 mL |

The final pH is adjusted to 7.4±0.4.

The clear solution is filtered through a 0.22 μm membrane and stored at 4° C.

C Pharmacodynamics and pharmacokinetics

C1: Protocol for Measuring the Pharmacodynamics and the Pharmacokinetics of the Solutions of Insulin Domestic pigs weighing approximately 50 kg that had been catheterized beforehand through the jugular are fasted for 2.5 hours before the start of the experiment. In the hour preceding the injection of insulin, 3 blood samples are collected in order to determine the basal level of glucose and of insulin.

The injection of insulin at the dose of 0.125 IU/kg for the insulin lispro is carried out subcutaneously in the flank or neck of the animal using an insulin pen (Novo, Sanofi or Lilly) provided with a 31 G needle.

Blood samples are then collected every 4 minutes for 20 minutes, then every 10 minutes for 3 hours. After each collection, the catheter is rinsed with a dilute heparin solution.

A drop of blood is collected to determine the glycemia using a glucometer.

The pharmacodynamics curves of the glucose, expressed as a percentage of the basal level, are then plotted. The time needed to reach the minimum level of glucose in the blood and 50% of the minimum level of glucose in the blood are determined for each pig and plotted as Tmin glucose and T50% Rmin glucose, respectively. The averages of the Tmin glucose and T50% Rmin glucose values are then calculated.

The remaining blood is collected in a dry tube and centrifuged to isolate the serum. The insulin contents in the serumn samples are measured for each pig using the immunoenzymatic sandwich ELISA method.

The pharmacokinetics curves expressed as delta of the basal level are then plotted. The time needed to reach the maximum concentration and the time needed to reach 50% of the maximum concentration of insulin in the serum for each pig are determined and plotted as Tmax insulin and T50% Cmax insulin, respectively. The averages of the Tmax insulin and T50% Cmax insulin values are then calculated.

C2: Pharmacodynamics and Pharmacokinetics Results of the Solutions of Insulins of Examples B2 and B1 (Injection in the Flank)

| Example | Insulin | Substituted citrate | Excipient | Number of pigs |
|---|---|---|---|---|
| B2 | Lispro | — | — | 9 |
| B11 | Lispro | A1 | Citrate 9.3 mM | 10 |

The pharmacodynamics results obtained with the compositions described in Examples B2 and B11 are presented in FIG. 1. The analysis of these curves shows that the composition of Example B11 comprising the substituted citrate A1 and citrate as excipient (curve plotted with squares corresponding to Example B11, Tmin glucose=44±18 min and T50% Rmin glucose=15±3 min) makes it possible to obtain a more rapid action than that of the commercial composition Humalog® of Example B2 (curved plotted with triangles corresponding to Example B2, Tmin glucose=61±23 min and T50% Rmin glucose=26±9 min).

Figure 2:
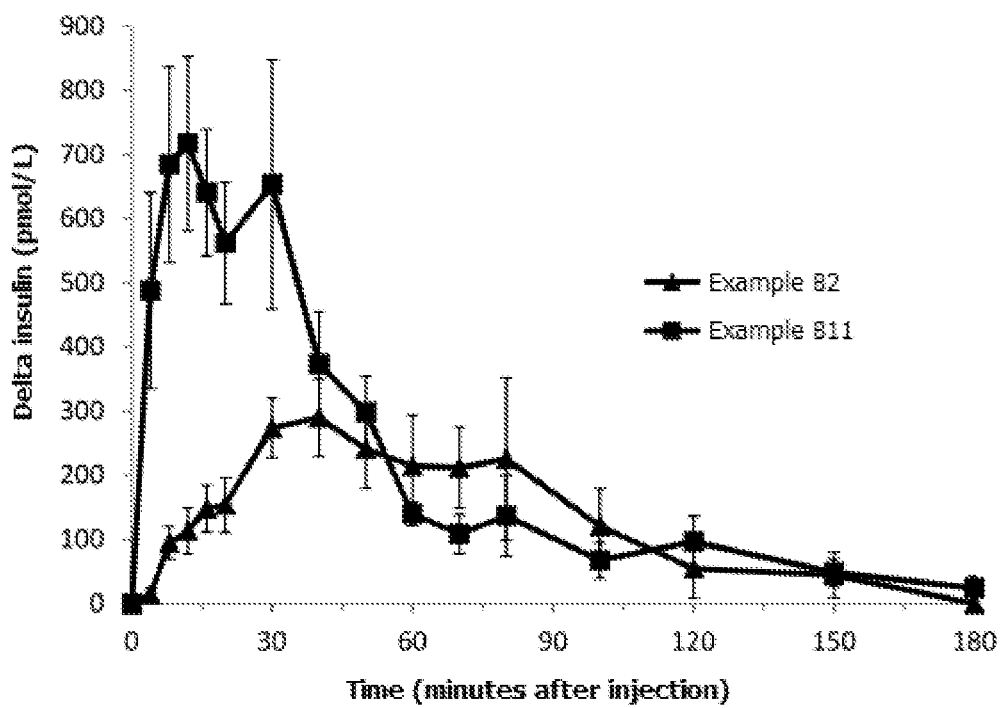
FIG. 2: Delta insulin (pmol/L) as a function of time (minutes after injection). The analysis of these curves shows that the composition of Example B11 comprising the substituted citrate A1 and citrate as excipient (curve plotted with squares corresponding to Example B11, Tmax insulin=20±23 min and T50% Cmax insulin=6±5 min) induces a more rapid absorption of the insulin lispro than the commercial composition Humalog® of Example B2 (curve plotted with triangles corresponding to Example B2, Tmax insulin=39±18 min and T50% Cmax insulin=24±14 min).

The pharmacokinetics results obtained with the compositions described in Examples B2 and B11 are presented in FIG. 2. The analysis of these curves shows that the composition of Example B11 comprising the substituted citrate A1 and citrate as excipient (curve plotted with squares corresponding to Example B11, Tmax insulin=20±23 min and T50% Cmax insulin=6±5 min) induces a more rapid absorption of the insulin lispro than the commercial composition Humalog® of Example B2 (curve plotted with triangles corresponding to Example B2, Tmax insulin=39±18 min and T50% Cmax insulin=24±14 min).

C3: Pharmacodynamics and Pharmacokinetics Results of the Solutions of Insulins of Examples B2 and B26 (Injection in the Flank)

| Example | Insulin | Substituted citrate | Excipient | Number of pigs |
|---|---|---|---|---|
| B2 | lispro | — | — | 9 |
| B26 | lispro | A1 at 14.6 mg/mL | — | 12 |

Figure 3:
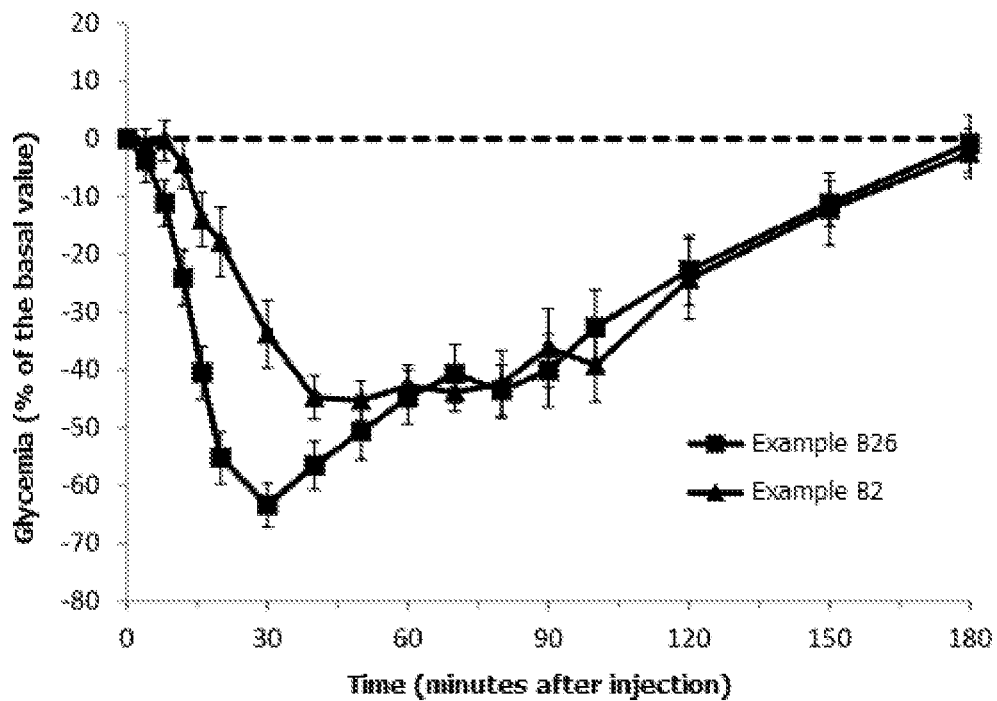
FIG. 3: Glycemia (% of the basal value) as a function of time (minutes after injection). The analysis of these curves shows that the composition of Example B26 comprising the substituted citrate A1 at 14.6 mg/mL (curve plotted with squares corresponding to Example B26, Tmin glucose=37±18 min and T50% Rmin glucose=14±3 min) makes it possible to obtain a more rapid action than that of the commercial composition Humalog® of Example B2 (curve plotted with triangles corresponding to Example B2, Tmin glucose=61±23 min and T50% Rmin glucose=26±9 min).

The pharmacodynamics results obtained with the compositions described in Examples B2 and B26 are presented in FIG. 3. The analysis of these curves shows that the composition of Example B26 comprising the substituted citrate A1 at 14.6 mg/mL (curve plotted with squares corresponding to Example B26, Tmin glucose=37±18 min and T50% Rmin glucose=14±3 min) makes it possible to obtain a more rapid action than that of the commercial composition Humalog® of Example B2 (curved plotted with triangles corresponding to Example B2, Tmin glucose=61±23 min and T50% Rmin glucose=26±9 min).

Figure 4:
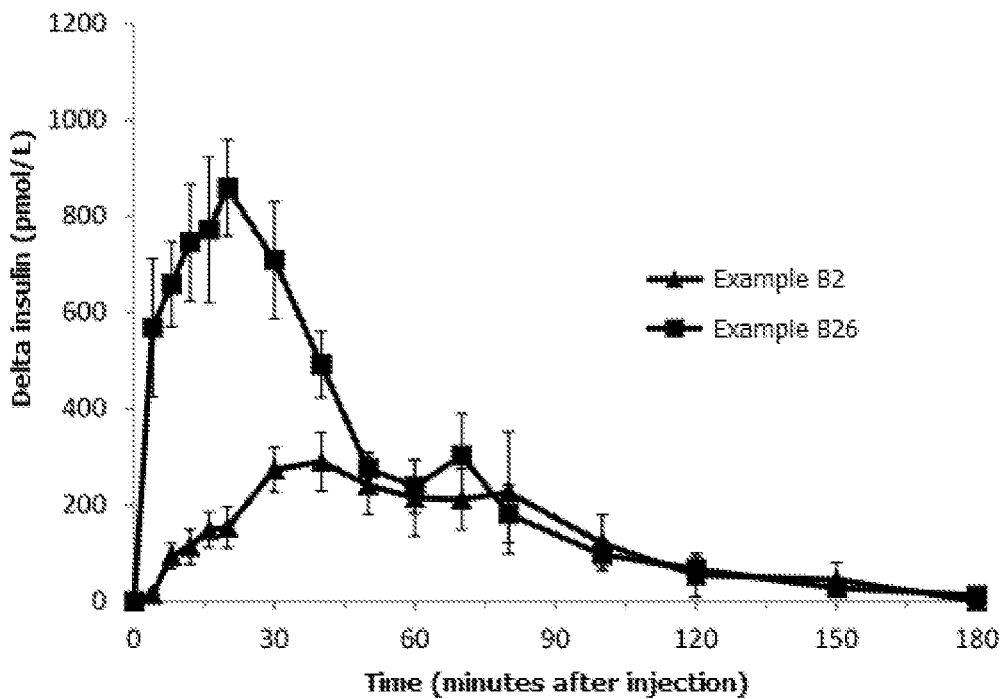
FIG. 4: Delta insulin (pmol/L) as a function of time (minutes after injection). The analysis of these curves shows that the composition of Example B26 comprising the substituted citrate A1 at 14.6 mg/mL (curve plotted with squares corresponding to Example B26, Tmax insulin=22±17 min and T50% Cmax insulin=5±3 min) induces a more rapid absorption of the insulin lispro than the commercial composition Humalog® of Example B2 (curve plotted with triangles corresponding to Example B2, Tmax insulin=39±18 min and T50% Cmax insulin=24±14 min).

The pharmacokinetics results obtained with the compositions described in Examples B2 and B26 are presented in FIG. 4. The analysis of these curves shows that the composition of Example B26 comprising the substituted citrate A1 at 14.6 mg/mL (curve plotted with squares corresponding to Example B26, Tmax insulin=22±17 min and T50% Cmax insulin=5±3 min) induces a more rapid absorption of the insulin lispro than the commercial composition Humalog® of Example B2 (curve plotted with triangles corresponding to Example B2, Tmax insulin=39±18 min and T50% Cmax insulin=24±14 min).

C4: Pharmacodynamics and Pharmacokinetics Results of the Solutions of Insulins of Examples B2 and B39 (Injection in the Flank)

| Example | Insulin | Substituted citrate | Excipient | Number of pigs |
|---|---|---|---|---|
| B2 | lispro | — | — | 14 |
| B39 | lispro | A2 | Citrate 9.3 mM | 12 |

Figure 5:
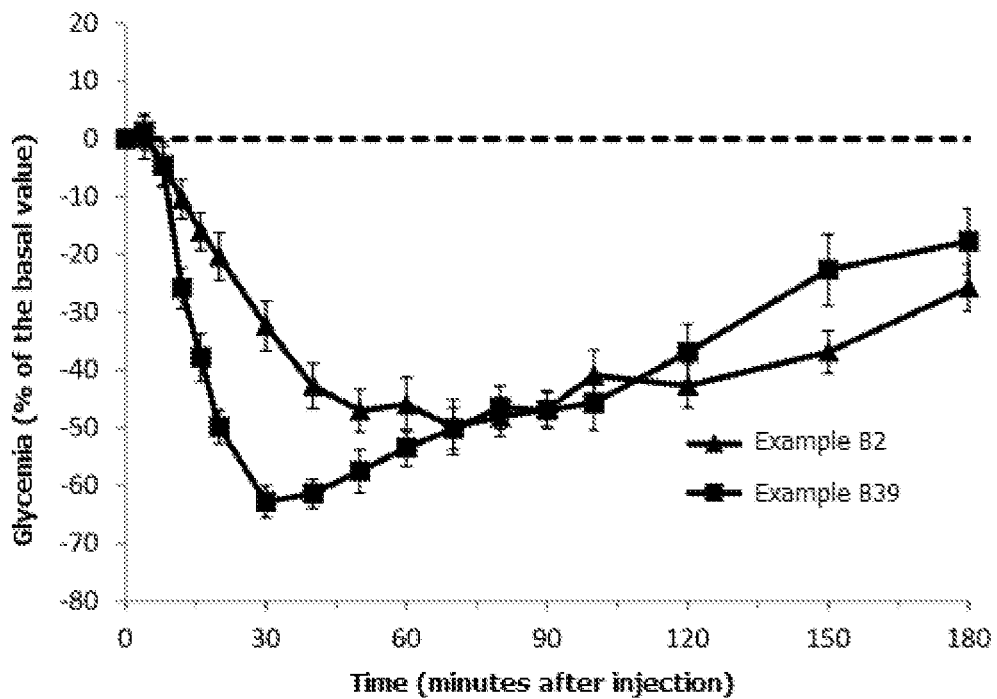
FIG. 5: Glycemia (% of the basal value) as a function of time (minutes after injection). The analysis of these curves shows that the composition of Example B39 comprising the substituted citrate A2 and citrate as excipient (curve plotted with squares corresponding to Example B39, Tmin glucose=37±12 min and T50% Rmin glucose=14±3 min) makes it possible to obtain a more rapid action than that of the commercial composition Humalog® of Example B2 (curve plotted with triangles corresponding to Example B2, Tmin glucose=76±40 min and T50% Rmin glucose=29±13 min).

The pharmacodynamics results obtained with the compositions described in Examples B2 and B39 are presented in FIG. 5. The analysis of these curves shows that the composition of Example B39 comprising the substituted citrate A2 and citrate as excipient (curve plotted with squares corresponding to Example B39, Tmax insulin=37±12 min and T50% Cmax insulin=14±3 min) makes it possible to obtain a more rapid action than that of the commercial composition Humalog® of Example B2 (curve plotted with triangles corresponding to Example B2, Tmin glucose=76±40 min and T50% Rmin glucose=29±13 min).

Figure 6:
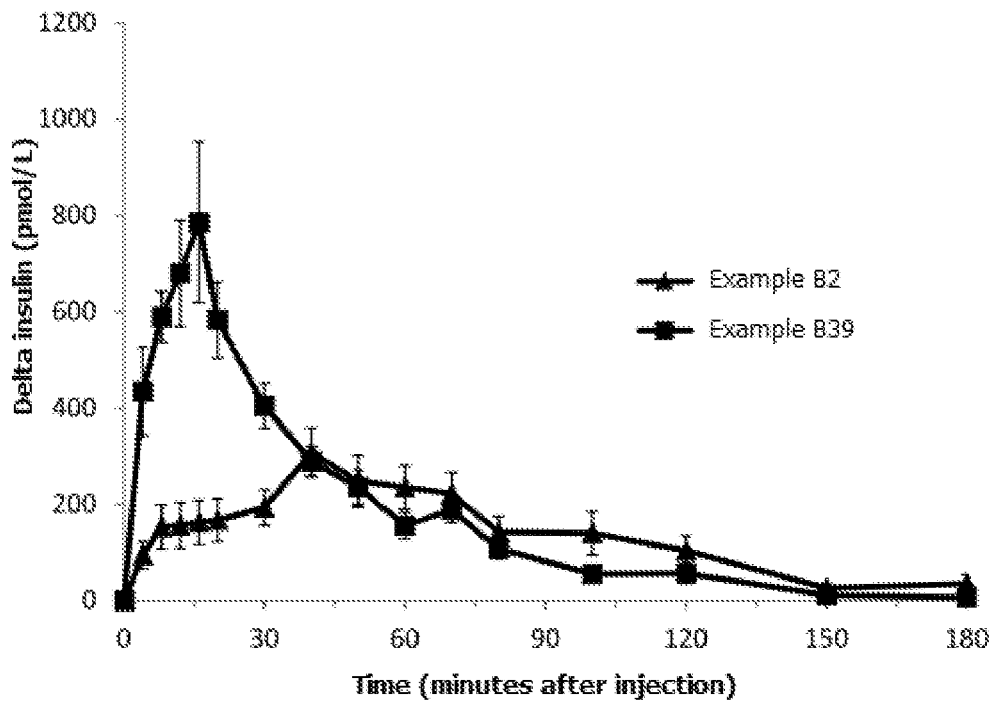
FIG. 6: Delta insulin (pmol/L) as a function of time (minutes after injection). The analysis of these curves shows that the composition of Example B39 comprising the substituted citrate A2 and citrate as excipient (curve plotted with squares corresponding to Example B39, Tmax insulin=34±26 min and T50% Cmax insulin=9±6 min) induces a more rapid absorption of the insulin lispro than the commercial composition Humalog® of Example B2 (curve plotted with triangles corresponding to Example B2, Tmax insulin=43±24 min and T50% Cmax insulin=20±19 min).

The pharmacokinetics results obtained with the compositions described in Examples B2 and B39 are presented in FIG. 6. The analysis of these curves shows that the composition of Example B39 comprising the substituted citrate A2 and citrate as excipient (curve plotted with squares corresponding to Example B39, Tmax insulin=34±26 min and T50% Cmax insulin=9±6 min) induces a more rapid absorption of the insulin lispro than the commercial composition Humalog® of Example B2 (curve plotted with triangles corresponding to Example B2. Tmax insulin=43±24 min and T50% Cmax insulin=20±19 min).

C5: Pharmacodynamics and Pharmacokinetics Results of the Solutions of Insulin of Examples B2 and B51 (Injection in the Flank)

| Example | Insulin | Substituted citrate | Excipient | Number of pigs |
|---|---|---|---|---|
| B2 | lispro | — | — | 14 |
| B51 | lispro | A3 | Citrate 9.3 mM | 12 |

Figure 7:
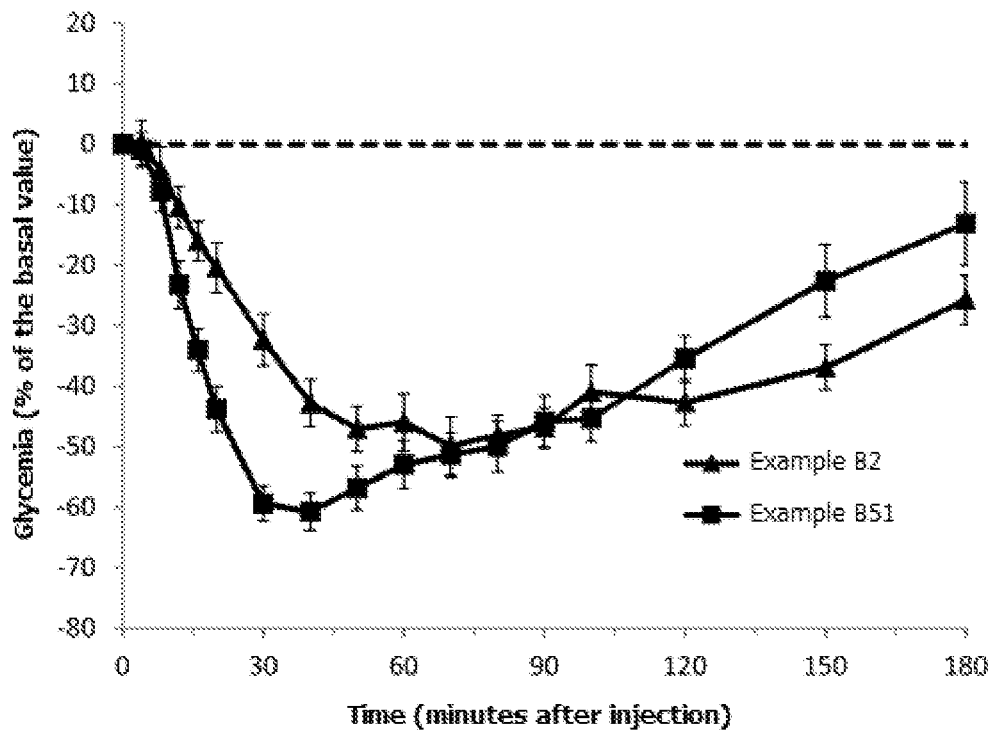
FIG. 7: Glycemia (% of the basal value) as a function of time (minutes after injection). The analysis of these curves shows that the composition of Example B51 comprising the substituted citrate A3 and citrate as excipient (curve plotted with squares corresponding to Example B51, Tmin glucose=46±14 min and T50% Rmin glucose=15±4 min) makes it possible to obtain a more rapid action than that of the commercial composition Humalog® of Example B2 (curve plotted with triangles corresponding to Example B2, Tmin glucose=76±40 min and T50% Rmin glucose=29±13 min).

The pharmacodynamics results obtained with the compositions described in Examples B2 and B51 are presented in FIG. 7. The analysis of these curves shows that the composition of Example B51 comprising the substituted citrate A3 and citrate as excipient (curve plotted with squares corresponding to Example B51, Tmin glucose=46±14 min and T50% Rmin glucose=15±4 min) makes it possible to obtain a more rapid action than that of the commercial composition Humalog® of Example B2 (curve plotted with triangles corresponding to Example B2, Tmin glucose=76±40 min and T50% Rmin glucose=29±13 min).

Figure 8:
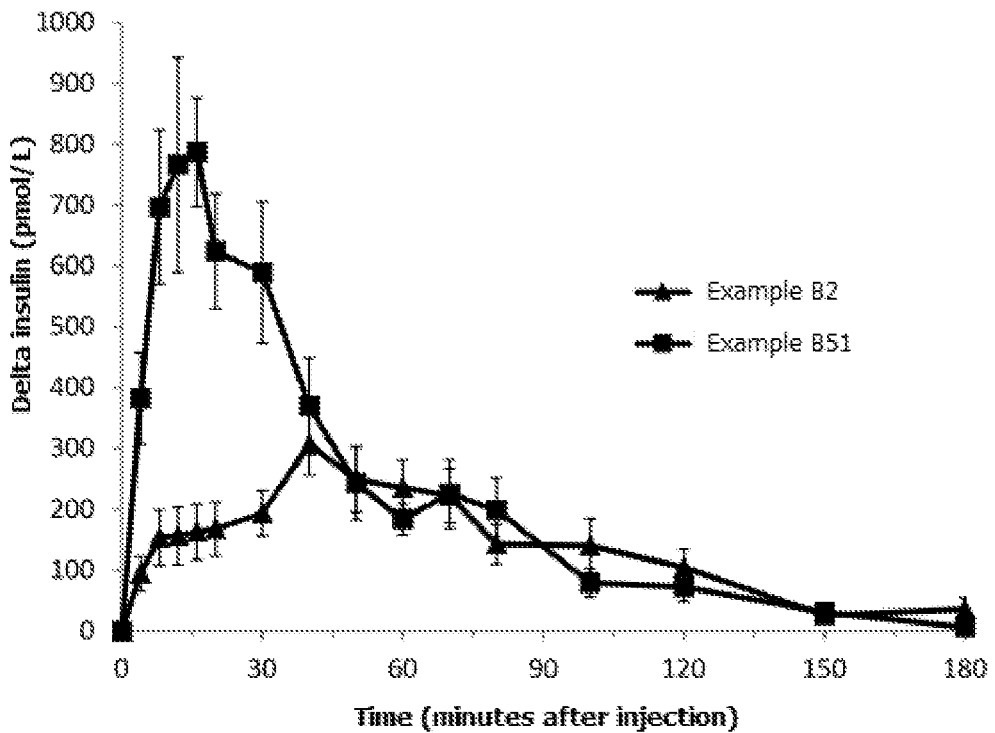
FIG. 8: Delta insulin (pmol/L) as a function of time (minutes after injection). The analysis of these curves shows that the composition of Example B51 comprising the substituted citrate A3 and citrate as excipient (curve plotted with squares corresponding to Example B51, Tmax insulin=17±9 min and T50% Cmax insulin=6±3 min) induces a more rapid absorption of the insulin lispro than the commercial composition Humalog® of Example B2 (curve plotted with triangles corresponding to Example B2, Tmax insulin=43±24 min and T50% Cmax insulin=20±19 min).

The pharmacokinetics results obtained with the compositions described in Examples B2 and B51 are presented in FIG. 8. The analysis of these curves shows that the composition of Example B51 comprising the substituted citrate A3 and citrate as excipient (curve plotted with squares corresponding to Example B51, Tmax insulin=17±9 min and T50% Cmax insulin=6±3 min) induces a more rapid absorption of the insulin lispro than the commercial composition Humalog® of Example B2 (curve plotted with triangles corresponding to Example B2, Tmax insulin=43±24 min and T50% Cmax insulin=20±19 min).

C6. Pharmacodynamics and Pharmacokinetics Results of the Solutions of Insulin of Examples B2 and B62 (Injection in the Flank)

| Example | Insulin | Substituted citrate | Excipient | Number of pigs |
|---------|---------|---------------------|-----------|----------------|
| B2      | Lispro  | —                   | —         | 11             |
| B62     | Lispro  | A3                  | —         | 11             |

Figure 11:
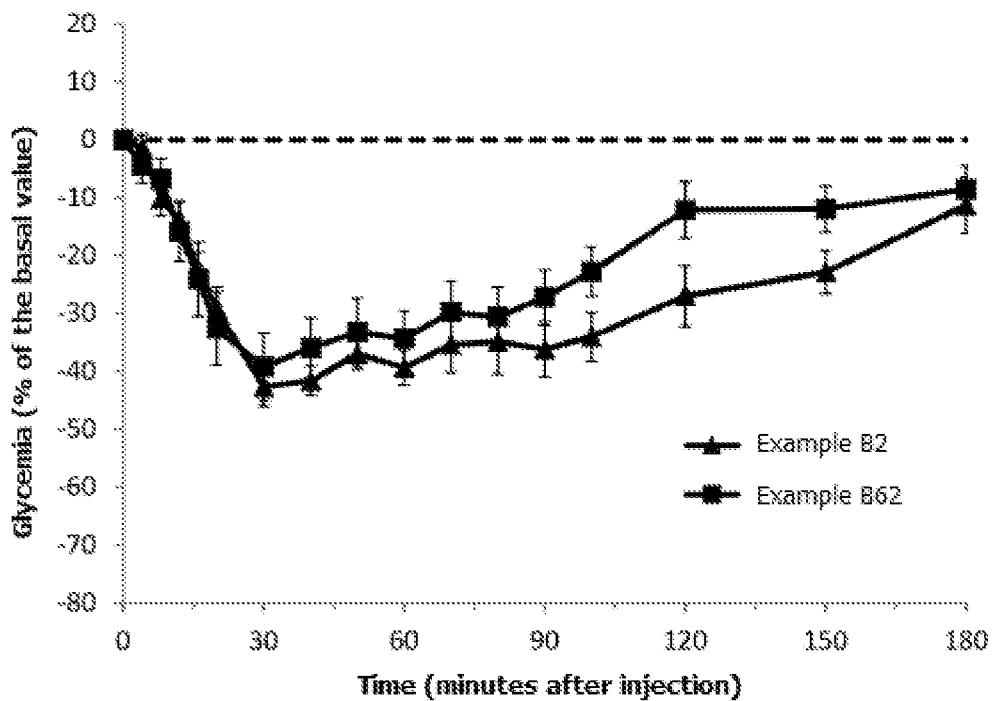
FIG. 11: Glycemia (% of the basal value) as a function of time (minutes after injection). The analysis of these curves shows that the composition of Example B62 comprising the substituted citrate A3 (curve plotted with squares corresponding to Example B62, Tmin glucose=46±24 min and T50% Rmin glucose=16±6 min) makes it possible to obtain a more rapid action than that of the commercial composition Humalog® of Example B2 (curve plotted with triangles corresponding to Example B2, Tmin glucose=63±35 min and T50% Rmin glucose=19±6 min).

The pharmacodynamics results obtained with the compositions described in Examples B2 and B62 are presented in FIG. 11. The analysis of these curves shows that the composition of Example B62 comprising the substituted citrate A3 (curve plotted with squares corresponding to Example B62, Tmin glucose=46±24 min and T50% Rmin glucose=16±6 min) makes it possible to obtain a more rapid action than that of the commercial composition Humalog® of Example B2 (curve plotted with triangles corresponding to Example B2, Tmin glucose=63±35 min and T50% Rmin glucose=19±6 min).

Figure 12:
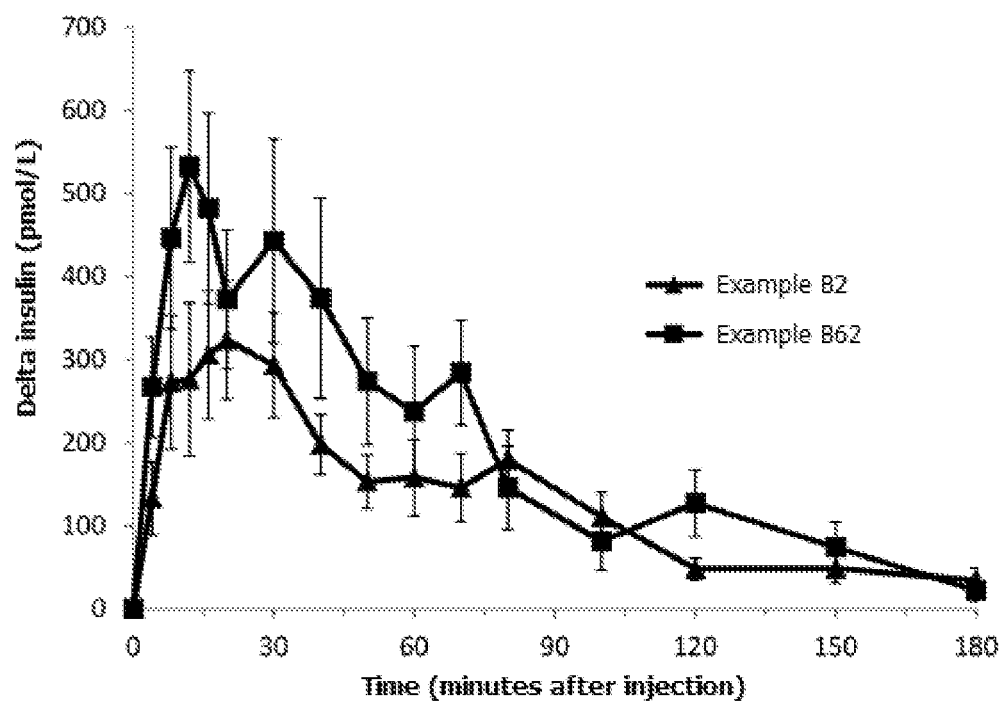
FIG. 12: Delta insulin (pmol/L) as a function of time (minutes after injection). The analysis of these curves shows that the composition of Example B62 comprising the substituted citrate A3 (curve plotted with squares corresponding to Example B62, Tmax insulin=24±20 min and T50% Cmax insulin=7±4 min) induces a more rapid absorption of the insulin lispro than the commercial composition Humalog® of Example B2 (curve plotted with triangles corresponding to Example B2. Tmax insulin=26±19 min and T50% Cmax insulin=9±7 min).

The pharmacokinetics results obtained with the compositions described in Examples B2 and B62 are presented in FIG. 12. The analysis of these curves shows that the composition of Example B62 comprising the substituted citrate A3 (curve plotted with squares corresponding to Example B62, Tmax insulin=24±20 min and T50% Cmax insulin=7±4 min) induces a more rapid absorption of the insulin lispro than the commercial composition Humalog® of Example B2 (curve plotted with triangles corresponding to Example B2, Tmax insulin=26±19 min and T50% Cmax insulin=9±7 min).

D Circular dichroism

D1 Association State of the Insulin Lispro Evaluated by Circular Dichroism in the Presence of Different Substituted Citrates and of Citrate Circular dichroism makes it possible to study the secondary and quaternary structure of the insulin. The monomers of insulin self-organize to form dimers and hexamers. The hexamer is the most stable form of insulin physically and chemically. There are two hexameric forms, R6 form and T6 form. The insulin lispro has a strong signal at 240 nm characteristic of the hexameric R6 form (the most stable form). The loss of the signal at 240 nm is connected with a destabilization of the hexamer and the conversion from R6 to T6.

Preparation of a Solution of Sodium Citrate at 1.010 M

A solution of sodium citrate is obtained by dissolving 14.90 g of sodium citrate (50.69 mmol) in 50 mL of water in a graduated flask. The pH is adjusted to 7.4 by adding 0.21 mL of 1M HCl.

Preparation of the Solutions of Insulin Lispro at 100 IU/mL in the Presence of Substituted Citrate and of Citrate For a final volume of 100 mL of formulation, with a concentration of substituted citrate at 7.3 mg/mL and a concentration of 9.3 mM of citrate, the different reagents are added in the quantities specified below and in the following order:

| Lyophilized substituted citrate         | 730 mg  |
| Commercial solution Humalog® 100 IU/mL  | 100 mL  |
| Solution of sodium citrate at 1.010M    | 921 µL  |

For the citrate, one can use the acid form or the base form of the salt of sodium, potassium, or of another salt compatible with an injectable formulation.

The final pH is adjusted to 7.4±0.4

The clear solution is filtered through a 0.22 µm membrane and stored at 4° C.

Preparation of the Solution of Insulin Lispro at 100 IU/mL in the Presence of Substituted Citrate at 14.6 mg/mL For a final volume of 100 mL of formulation, with a concentration of substituted citrate at 7.3 mg/mL, the different reagents are added in the quantities specified below and in the following order:

| Lyophilized substituted citrate         | 1460 mg |
| Commercial solution Humalog® 100 IU/mL  | 100 mL  |

The final pH is adjusted to 7.4±0.4. The clear solution is filtered through a 0.22 µm membrane and stored at 4° C.

Preparation of the Solution of Insulin Lispro at 100 IU/mL in the Presence of EDTA For a final volume of 100 mL of formulation, with a concentration of 300 µM of EDTA, the different reagents are added in the quantities specified below and in the following order:

| Commercial solution Humalog® 100 IU/mL | 100 mL |
| Commercial solution of EDTA at 0.5M    | 60 µL  |

The final pH is adjusted to 7.4±0.4. The clear solution is filtered through a 0.22 µm membrane and stored at 4° C.

Two measurement series were carried out. The results obtained are presented in FIG. 9 and in FIG. 10.

Figure 9:
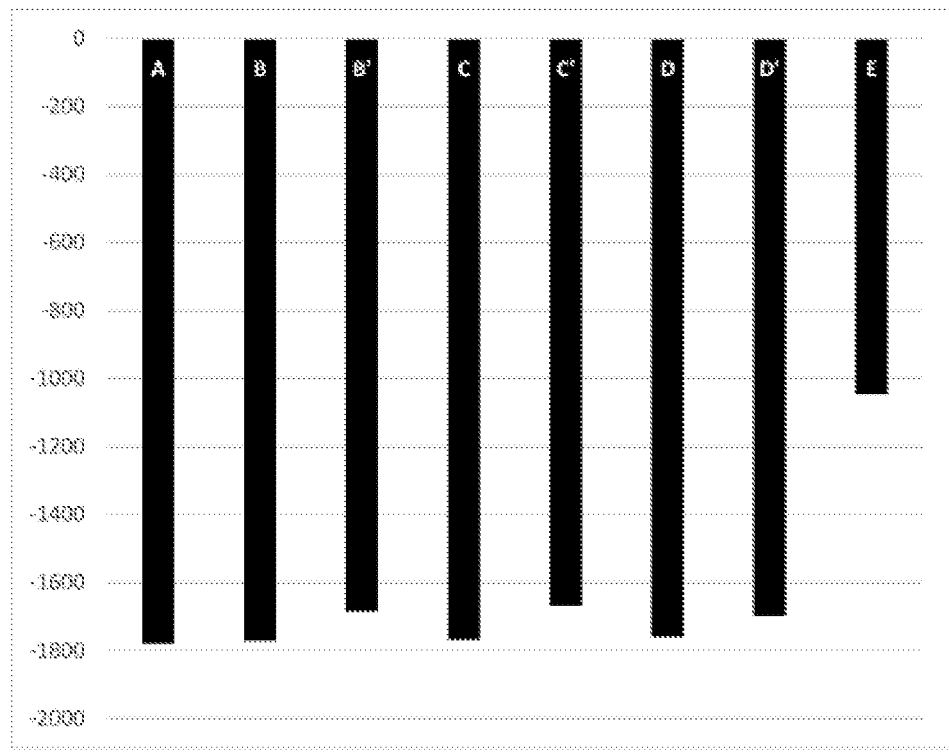
FIG. 9.

FIG. 9 describes, on the ordinate, the CD signal at 240 nm ($deg \cdot cm^2 \cdot dmol^{-1}$) and, on the abscissa:

A: insulin lispro 100 IU/mL

B: insulin lispro 100 IU/mL+7.3 mg of substituted citrate A1

B': insulin lispro 100 IU/mL+7.3 mg of substituted citrate A1 and citrate at 9.3 mM C: insulin lispro 100 IU/mL+7.3 mg of substituted citrate A2

C': insulin lispro 100 IU/mL+7.3 mg of substituted citrate A2 and citrate at 9.3 mM D: insulin lispro 100 IU/mL+7.3 mg of substituted citrate A3

Figure 10:
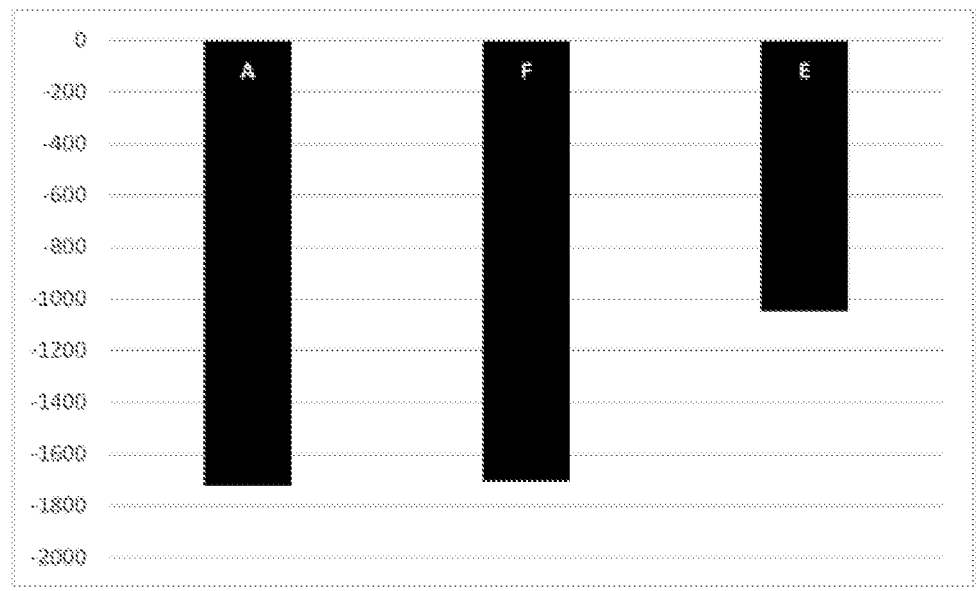
FIG. 10.

D': insulin lispro 100 IU/mL+7.3 mg of substituted citrate A3 and citrate at 9.3 mM E: insulin lispro+EDTA at 300 µM FIG. 10 describes, on the ordinate, the CD signal at 240 nm (deg·cm$^2$·dmol$^{-1}$) and, on the abscissa:
A: insulin lispro 100 IU/mL
F: insulin lispro 100 IU/mL+14.6 mg of substituted citrate A1
E: insulin lispro+EDTA at 300 M The EDTA completely destructures the R6 form of the insulin Lispro. The EDTA thus has a pronounced effect on the hexamer.

On the other hand, the mixtures of substituted anionic compound and citrate have only very little impact on the CD signal at 240 nm. Therefore, these compounds have little or no impact on the R6 structure of the hexamer, and, a fortiori, on the hexameric structure of the insulin lispro. In the compositions according to the invention, the insulin is thus considered to be in hexameric form.

D2 Association State of the Insulin Lispro Evaluated by Circular Dichroism in the Presence of the Substituted Citrate A3

Circular dichroism makes it possible to study the secondary and quaternary structures of insulin. The monomers of insulin self-organize to form dimers and hexamers. The hexamer is the most stable form of insulin physically and chemically. There are two hexameric forms, the R6 form and the T6 form. The insulin Lispro has a strong signal at 240 nm, characteristic of the hexameric R6 form (the most stable form). The loss of the signal at 240 nm is connected with a destabilization of the hexamer and the conversion from R6 to T6.

Preparation of a Solution of Sodium Citrate at 1.010 M

A solution of sodium citrate is obtained by dissolving 14.90 g of sodium citrate (50.69 mmol) in 50 mL of water in a graduated flask. The pH is adjusted to 7.4 by adding 0.21 mL of 1M HCl.

Preparation of the Solutions of Insulin Lispro at 100 IU/mL in the Presence of Substituted Citrate and of Citrate For a final volume of 100 mL of formulation, with a concentration of substituted citrate at 7.3 mg/mL and a concentration of 9.3 mM of citrate, the different reagents are added in the quantities specified below and in the following order:

| Lyophilized substituted citrate | 730 mg |
| Commercial solution Humalog ® 100 IU/mL | 100 mL |
| Solution of sodium citrate at 1.010M | 921 µL |

For the citrate, one can use the acid form or the base form of the salt of sodium, potassium, or of another salt compatible with an injectable formulation.

The final pH is adjusted to 7.4±0.4
The clear solution is filtered through a 0.22 µm membrane and stored at 4° C.

Preparation of the Solution of Insulin Lispro at 100 IU/mL in the Presence of Substituted Citrate at 7.3 mg/mL or at 14.6 mg/mL For a final volume of 100 mL of formulation, with a concentration of substituted citrate at 7.3 mg/mL or 14.6 mg/mL, the different reagents are added in the quantities specified below and in the following order:

| Lyophilized substituted citrate | 730 mg or 1460 mg |
| Commercial solution Humalog ® 100 IU/mL | 100 mL |

The final pH is adjusted to 7.4±0.4. The clear solution is filtered through a 0.22 µm membrane and stored at 4° C.

Preparation of the Solution of Insulin Lispro at 100 IU/mL in the Presence of EDTA For a final volume of 100 mL of formulation, with a concentration of 300 µM of EDTA, the different reagents are added in the quantities specified below and in the following order:

| Commercial solution Humalog ® 100 IU/mL | 100 mL |
| Commercial solution of EDTA at 0.5M | 60 µL |

The final pH is adjusted to 7.4±0.4. The clear solution is filtered through a 0.22 µm membrane and stored at 4° C.

Two measurement series were carried out. The results obtained are presented in FIG. 13 and in FIG. 14.

Figure 13:
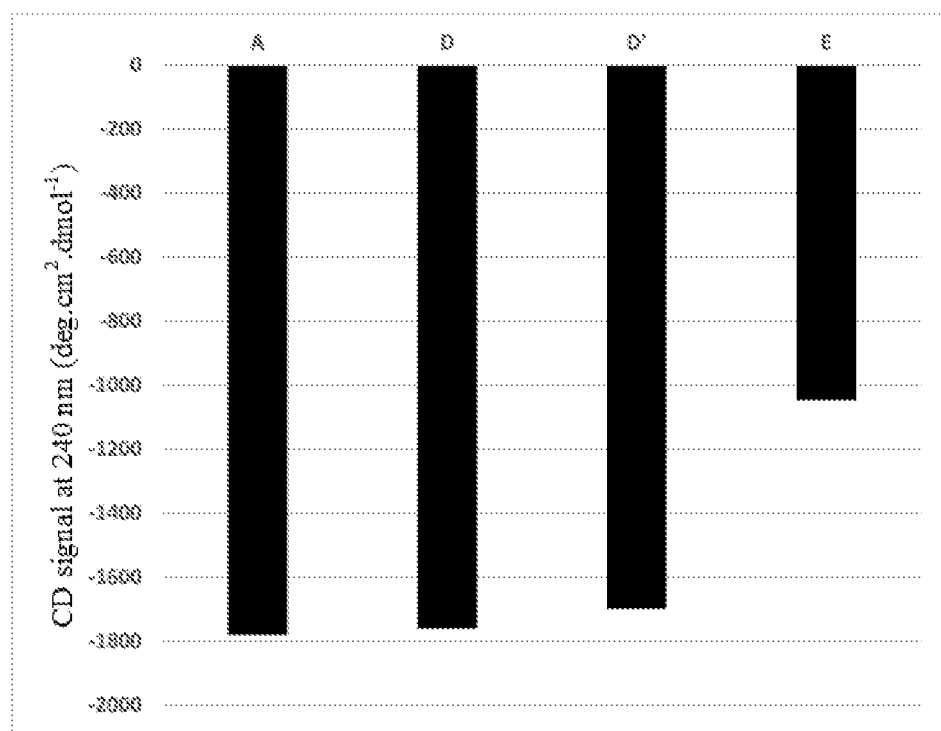
FIG. 13.
Figure 14:
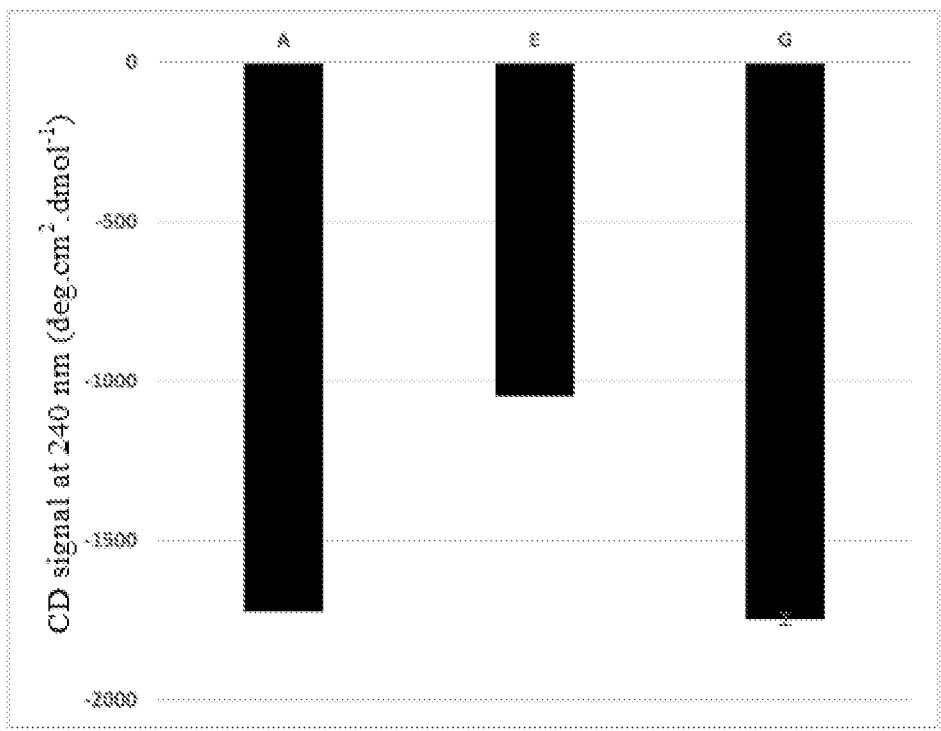
FIG. 14.

FIG. 13 describes, on the ordinate, the CD signal at 240 nm (deg·cm$^2$·dmol$^{-1}$) and, on the abscissa:
A: insulin lispro 100 IU/mL
D: insulin lispro 100 IU/mL+7.3 mg/ml of substituted citrate A3
D': insulin lispro 100 IU/mL+7.3 mg/ml of substituted citrate A3 and citrate at 9.3 mM
E: insulin lispro+EDTA at 300 µM FIG. 14 describes, on the ordinate, the CD signal at 240 nm (deg·cm$^2$·dmol$^{-1}$) and, on the abscissa:
A: insulin lispro 100 IU/mL
E: Insulin lispro+EDTA at 300 µM
G: insulin lispro 100 IU/mL+14.6 mg/mL of substituted citrate A3

The EDTA completely destructures the R6 form of the insulin lispro. The EDTA thus has a pronounced effect on the hexamer.

On the other hand, the substituted citrate A3 alone and the substituted citrate A3 in the presence of citrate have only very little impact on the CD signal at 240 nm. These compounds thus have little or no impact on the R6 structure of the hexamer, and, a fortiori, on the hexameric structure of the insulin lispro. In the compositions according to the invention, the insulin is thus considered to be in hexameric form.

D3 Association State of Human Insulin Evaluated by Circular Dichroism in the Presence of Substituted Citrate A3

Circular dichroism makes it possible to study the secondary and quaternary structures of insulin. The monomers of insulin self-organize to form dimers and hexamers. The hexamer is the most stable form of insulin physically and chemically. There are two hexameric forms, the R6 form and the T6 form. The human insulin has a strong signal at 240 nm, characteristic of the hexameric R6 form (the most stable form). The loss of the signal at 240 nm is connected with a destabilization of the hexamer and the conversion from R6 to T6.

Preparation of the Solutions of Human Insulin at 100 IU/mL in the Presence of Substituted Citrate and of Citrate For a final volume of 100 mL of formulation, with a concentration of substituted citrate at 7.3 mg/mL and a concentration of 9.3 mM of citrate, the different reagents are added in quantities specified below and in the following order:

| Lyophilized substituted citrate | 730 mg |
| Commercial solution Humulin ® R 100 IU/mL | 100 mL |
| Solution of sodium citrate at 1.010M | 921 µL |

For the citrate, one can use the acid form or the base form of the salt of sodium, potassium, or of another salt compatible with an injectable formulation.

The final pH is adjusted to 7.4±0.4

The clear solution is filtered through a 0.22 μm membrane and stored at 4° C.

Preparation of the Solution of Human Insulin at 100 IU/mL in the Presence of Substituted Citrate at 7.3 mg/mL or at 14.6 mg/mL For a final volume of 100 mL of formulation, with a concentration of substituted citrate at 7.3 mg/mL or 14.6 mg/mL, the different reagents are added in the quantities specified below and in the following order:

| | |
|---|---|
| Lyophilized substituted citrate | 730 mg or 1460 mg |
| Commercial solution Humulin® R 100 IU/mL | 100 mL |

The final pH is adjusted to 7.4±0.4. The clear solution is filtered through a 0.22 μm membrane and stored at 4° C.

Preparation of the Solution of Human Insulin at 100 IU/mL in the Presence of EDTA For a final volume of 100 mL of formulation, with a concentration of 300 μM or 6 mM of EDTA, the different reagents are added in the quantities specified below and in the following order:

| | |
|---|---|
| Commercial solution Humulin® R 100 IU/mL | 100 mL |
| Sodium EDTA (powder) | 11 mg (300 μM) or 221 mg (6 mM) |

The final pH is adjusted to 7.4±0.4. The clear solution is filtered through a 0.22 μm membrane and stored at 4° C.

Two measurement series were carried out. The results obtained are presented in FIG. 15 and in FIG. 16.

Figure 15:
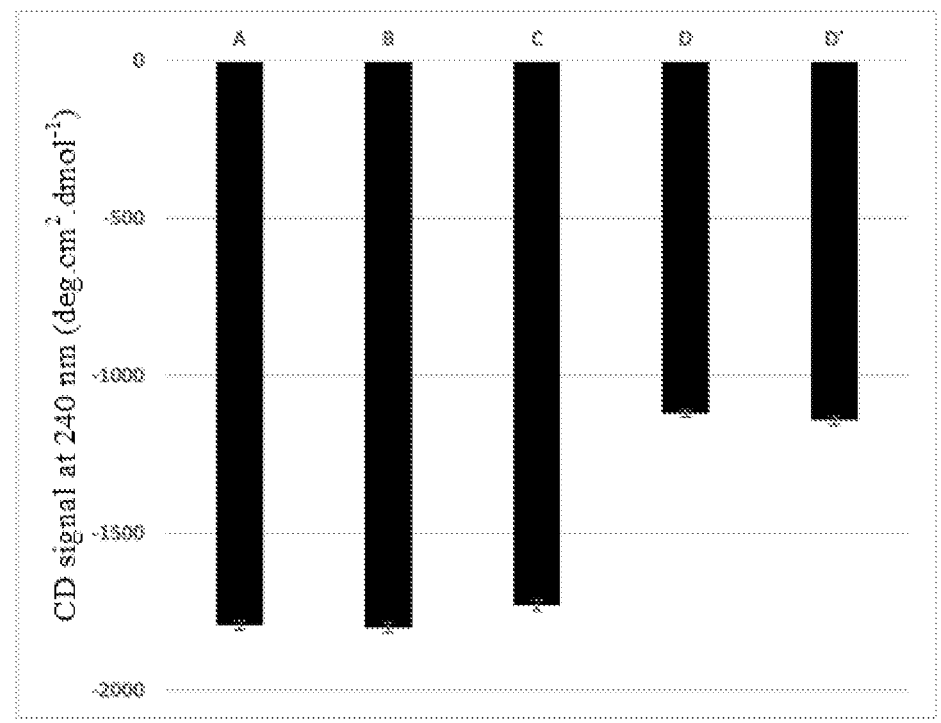
FIG. 15.

FIG. 15 describes, on the ordinate, the CD signal at 240 nm (deg·cm$^2$·dmol$^-$) and, on the abscissa:

A: human insulin 100 IU/mL

B: human insulin 100 IU/mL+7.3 mg/mL of substituted citrate A3

Figure 16:
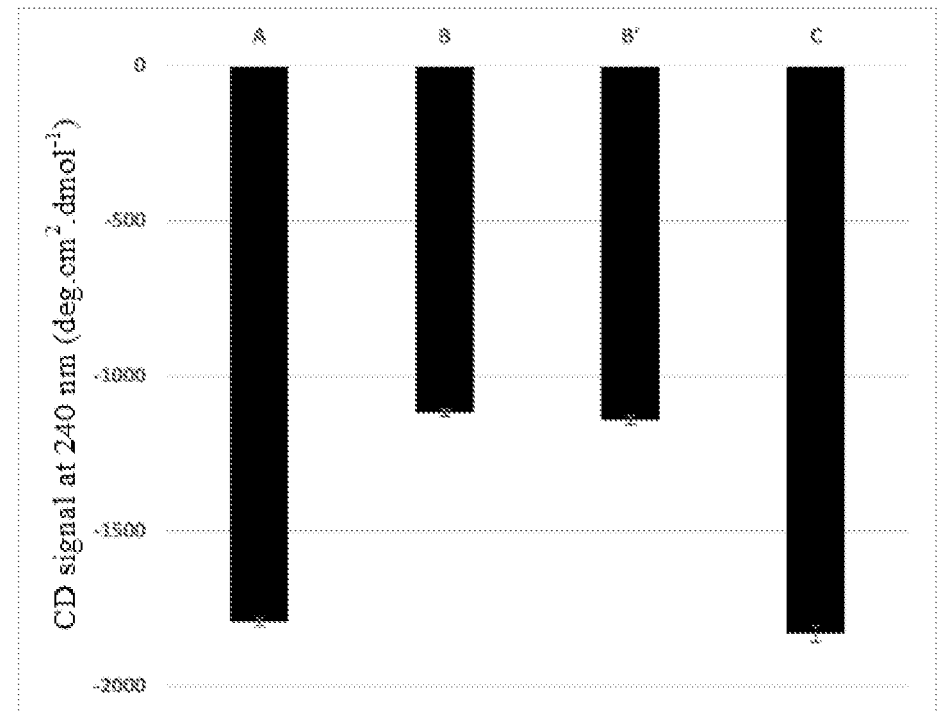
FIG. 16.

C: human insulin 100 IU/mL+7.3 mg/mL of substituted citrate A3 and citrate at 9.3 mM D: human insulin 100 IU/mL+EDTA at 300 M D': human insulin 100 IU/mL+EDTA at 6 mM FIG. 16 describes, on the ordinate, the CD signal at 240 nm (deg·cm$^2$·dmol$^{-1}$) and, on the abscissa:

A: human insulin 100 IU/mL (Humulin® R)

B: human insulin 100 IU/mL+EDTA at 300 μM

B': human insulin 100 IU/mL+EDTA at 6 mM

C: human insulin 100 IU/mL+14.6 mg/mL of substituted citrate A3.

The EDTA completely destructures the R6 form of human insulin. The EDTA thus has a pronounced effect on the hexamer.

On the other hand, the substituted citrate A3 alone and the substituted citrate A3 with citrate have only very little impact on the CD signal at 240 nm. These compounds thus have little or no impact on the R6 structure of the hexamer, and, a fortiori, on the hexameric structure of the human insulin. In the compositions according to the invention, the insulin is thus considered to be in hexameric form.

E Solubility of the Compounds

E1 Solubility of the Substituted Citrates (A1. A2, A3 and A4)

The solubility of the substituted citrates (A1, A2, A3 and A4) was measured in a buffer solution.

In a buffer solution at 50 mM of Tris/HCl, pH 7.4 (1 mL), the substituted citrate in powder form (20 mg) is introduced. The tubes are stirred (rolling shaker) for 30 minutes at ambient temperature, then inspected visually. The pH is adjusted to 7.4±0.4.

No trace of insoluble matter is observed. The substituted citrates A1, A2, A3 and A4 are thus soluble at the concentration of 20 mg/mL in a buffer solution at 50 mM Tris/HCl at pH 7.4.

The limit of solubility of each of the substituted citrates A1, A2, A3 and A4 is thus greater than 20 mg/mL in a buffer solution at 50 mM Tris/HCl at pH 7.4.

The solubility of the substituted citrates (A1, A2, A3 and A4) is measured in the presence of insulin lispro 100 U/mL. In a commercial solution of insulin lispro (Humalog®) (1 mL), the substituted citrate in powder form (20 mg) is introduced. The tube was stirred (rolling shaker) for 30 minutes at ambient temperature, then inspected visually. The pH is adjusted to 7.4±0.4.

No trace of insoluble matter is observed. The substituted citrates A1, A2, A3 and A4 are thus soluble at the concentration of 20 mg/mL in the presence of insulin lispro 100 IU/mL.

The limit of solubility of each of the substituted citrates A1, A2, A3 and A4 is thus greater than 20 mg/mL in the presence of insulin lispro 100 IU/mL.

E2 Solubility of the Compounds of the Prior Art (CE1 and CE2)

The solubility of the compounds of the prior art (CE1 and CE2) was measured.

4 mL of a buffer solution at 50 mM of Tris/HCl at pH 7.4 were introduced into a glass tube, at ambient temperature. The compounds in powder form were added successively in the amount of 8 mg per addition. After each addition of compound, the tubes were stirred (rolling shaker) for 30 minutes at ambient temperature, then inspected visually. The pH is adjusted to 7.4±0.4.

The concentrations at which insoluble matter was observed are defined as being greater than the limit of solubility of the compound.

TABLE 3 solubility of the counter-examples in a Tris/HCl buffer solution

| Compound | Solubility (mg/mL) |
|---|---|
| CE1 | <2 |
| CE2 | <2 |

The solubility of the compounds of the prior art was also measured in the presence of insulin lispro 100 U/mL. 1 mL of a commercial solution of Humalog was introduced into a glass tube, at ambient temperature. The compounds in powder form were added successively in the amount of 2 mg per addition. After each addition of compound, the tubes were stirred (rolling shaker) for 30 minutes at ambient temperature, then inspected visually. The pH is adjusted to 7.4±0.4.

The concentrations at which insoluble matter was observed are defined as being greater than the limit of solubility of the compound in the presence of insulin lispro 100 IU/mL.

TABLE 4

| solubility of the counter-examples in the presence of insulin lispro 100 IU/mL ||
| Compound | Solubility (mg/mL) |
| --- | --- |
| CE1 | <2 |
| CE2 | <2 |

The compounds of the prior art cannot be used in aqueous solutions according to the invention. A limit of solubility of less than 2 mg/mL is observed for the compounds CE1 and CE2, which is at least 10 times lower than that of the substituted citrates of the invention.

The invention claimed is:

1. A composition, in the form of an aqueous solution, comprising an insulin in hexameric form and at least one substituted citrate of formula I:

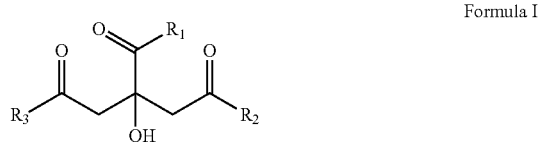

Formula I in which:
  $R_1$, $R_2$, $R_3$, identical or different, represent OH or AA,
  at least one of the $R_1$, $R_2$, $R_3$ is an AA radical,
  AA is a radical resulting from a natural or synthetic aromatic amino acid comprising at least one phenyl group or indole group, substituted or not substituted, said AA radical having at least one free carboxylic acid group,
  the carboxylic acid groups are in the form of a salt of an alkali metal selected from $Na^+$ and $K^+$, and
  wherein the composition is free of EDTA.

2. The composition according to claim 1, wherein the composition comprises, in addition, at least one polyanionic compound different from the substituted citrate.

3. The composition according to claim 1, wherein the substituted citrate is selected from the compounds of formula I in which the AA radical results from a natural aromatic amino acid.

4. The composition according to claim 1, wherein the substituted citrate is selected from the compounds of formula I in which at least $R_1$ is an AA radical.

5. The composition according to claim 1, wherein the substituted citrate is selected from the compounds of formula I in which at least $R_2$ is an AA radical.

6. The composition according to claim 1, wherein the substituted citrate is selected from the compounds of formula I in which at least $R_1$ and $R_2$ are an AA radical.

7. The composition according to claim 1, wherein the substituted citrate is selected from the compounds of formula I in which at least $R_2$ and $R_3$ are an AA radical.

8. The composition according to claim 1, wherein the substituted citrate has the formula I in which $R_1$, $R_2$ and $R_3$ are an AA radical.

9. The composition according to claim 1, wherein the substituted citrate has the formula I in which $R_1$ is an AA radical, $R_2$ and $R_3$ are OH, and the AA radical results from phenylalanine.

10. The composition according to claim 1, wherein the substituted citrate has the formula I in which $R_2$ is an AA radical, $R_1$ and $R_3$ are OH, and the AA radical results from phenylalanine.

11. The composition according to claim 1, wherein the substituted citrate has the formula I in which $R_1$ is OH, $R_2$ and $R_3$ are an AA radical, and the AA radical results from phenylalanine.

12. The composition according to claim 1, wherein the substituted citrate has the formula I in which $R_1$, $R_2$ and $R_3$ are an AA radical, and the AA radical results from phenylalanine.

13. The composition according to claim 1, wherein the substituted citrate/insulin molar ratios are between 3 and 400.

14. The composition according to claim 1, wherein the substituted citrate/insulin mass ratios are between 0.5 and 30.

15. The composition according to claim 1, wherein a concentration of the substituted citrate is between 1.8 and 100 mg/mL.

16. The composition according to claim 1, wherein the insulin is human insulin selected from recombinant human insulins.

17. The composition according to claim 1, wherein the insulin is an insulin analog selected from the group consisting of insulin lispro, insulin aspart, and insulin glulisine.

18. A pharmaceutical composition comprising the ft composition according to claim 1, wherein a concentration of the insulin is between 240 and 3000 µM (40 to 500 IU/mL).

19. The composition according to claim 2, wherein the polyanionic compound different from said substituted citrate is selected from the group consisting of carboxylic polyacids and their salts of $Na^+$, $K^+$, $Ca^{2+}$ or $Mg^{2+}$.

20. The composition according to claim 2, wherein a concentration of the polyanionic compound different from said substituted citrate is between 2 and 150 mM.

21. A pharmaceutical formulation comprising the ft composition according to claim 1.

* * * * *